(12) United States Patent
Leadlay et al.

(10) Patent No.: US 7,148,045 B1
(45) Date of Patent: Dec. 12, 2006

(54) HYBRID POLYKETIDE SYNTHASES AND NOVEL LOADING DOMAINS

(75) Inventors: Peter Francis Leadlay, Cambridge (GB); James Staunton, Cambridge (GB); Jesus Cortes, Cambridge (GB); Hamish Alastair Irvine McArthur, Mystic, CT (US)

(73) Assignee: Biotica Technology Limited, Cambridge (GB)

( * ) Notice: Subject to any disclaimer, the term of this patent is extended or adjusted under 35 U.S.C. 154(b) by 0 days.

(21) Appl. No.: 09/720,840

(22) PCT Filed: Jun. 29, 1999

(86) PCT No.: PCT/GB99/02044

§ 371 (c)(1),
(2), (4) Date: Sep. 5, 2001

(87) PCT Pub. No.: WO00/00618

PCT Pub. Date: Jan. 6, 2000

(30) Foreign Application Priority Data

Jun. 29, 1998 (GB) ................................. 9814006.4

(51) Int. Cl.
*C12N 9/00* (2006.01)

(52) U.S. Cl. ...................................... 435/183; 536/23.2

(58) Field of Classification Search ................ 435/183
See application file for complete search history.

(56) References Cited

U.S. PATENT DOCUMENTS 5,672,491 A * 9/1997 Khosla et al. .............. 435/148
5,712,146 A * 1/1998 Khosla et al.

OTHER PUBLICATIONS

Kuhstoss et al. Production of a novel polyketide through the construction of a hybrid polyketide synthase. Gene (1996) 183:231-236.*
Khosia C. Harnessing the Biosynthetic Potential of Modular Polyketide Synthases. Chemical Reviews (1997) 97:2577-2590.*
Marsden et al. Engineering Broader Specificity into an Antibiotic-Producing Polyketide Synthase. Science (Jan., 1998) 279: 199-202.*
Oliynyk et al. A hybrid modular polyketide synthase obtained by domain swapping. Chem. Biol. (1996) 10: 833-839.*

* cited by examiner

*Primary Examiner*—Nashaat T. Nashed
(74) *Attorney, Agent, or Firm*—Dann, Dorfman, Herre & Skillman, P.C.

(57) ABSTRACT

A polyketide synthase ("PKS") of Type I is a complex multienzyme including a loading domain linked to a multiplicity of extension domains. The first extension module receives an acyl starter unit from the loading domain and each extension module adds a further ketide unit which may undergo processing (e.g. reduction). We have found that the Ksq domain possessed by some PKS's has decarboxylating activity, e.g. generating (substituted) acyl from (substituted) malonyl. The CLF domain of type II PKS's has similar activity. By inserting loading modules including such domains into PKS's not normally possessing them it is possible to control the starter units used.

14 Claims, 13 Drawing Sheets

```
KCLFDAU     ------------------------MVTGLGIVAPNGLGVGAIWDAVLNGRNGIGPLR
KCLFPEU     MTGTAARTASSQLHASPAGRRGLRGRAVVTGLGIVAPNGLGVGAYWDAVLNGRNGIGPLR
KCLFACT     ------------------------MSVLITGVGVVAPNGLGLAPYWSAVLDGRHGLGPVT
KCLFHIR     ------------------------MSTWVTGMGVVAPNGLGADDHWAATLKGRHGISRLS
KCLFGRA     ------------------------MSTPDRRRAVVTGLSVAAPGGLGTERYWKSLLTGENGIAELS
KCLFNOG     ------------------------MTAAVVVTGLGVVAPTGLGVREHWSSTVRGASAIGPVT
KCLFTCM     ------------------------MSAPAPVVVTGLGIVAPNGTGTEEYWAATLAGKSGIDVIQ
KCLFCIN     ------------------------MTP-VAVTGMGIAAPNGLGRPTTGRPPWAPRAASAAST
KCLFVNZ     ------------------------MSASVVVTGLGVAAPNGLGREDFWASTLGGKSGIGPLT
KCLFWHIE    ---------MSGPQRTGTGGGSRRAVVTGLGVLSPHGTGVEAHWKAVADGTSSLGPVT
KSGRA       ------------------------MTRRVVITGVGVRAPGGSGTKEFWDLLTAGRTATRPIS
KSHIR       ------------------------MTRRVVITGVGVRAPGGLGAKNFWELLTSGRTATRRIS
KSACT       ------------------------MKRRVVITGVGVRAPGGNGTRQFWELLTSGRTATRRIS
KSCIN       ------------------------MTQRRVAITGIEVLAPGGLGRKEFWQLLSEGRTATRGIT
KSVNZ       ------------------------MTARRVVITGIEVLAPGGTGSKAFWNLLSEGRTATRGIT
KSNOG       ------------------MKESINRRVVITGIGIVAPDATGVKPFWDLLTAGRTATRTIT
KSTCM       ---------------MTRHAEKRVVITGVGVRAPGGAGTAAFWDLLTAGRTATRTIS
KSDAU       ------------------------MNRRVVITGMGVVAPGAIGIKSFWELLLSGTTATRAIT
KSPEU       ------------------------MNRRIVITGIGVVAPGAVGTKPFWELLLSGTTATRAIS
KSWHI       ------------------------MTRRRVAVTGIGVVAPGGIGTPQFWRLLSEGRTATRRIS
                                     :**:  : :*   *                  .

KCLFDAU     RFADDGRLGRLAGEVSDFVP-EDHLPKRLLVQTDPMTQMTALAAAEWALREAGCAPSS--
KCLFPEU     RFTGDGRLGRLAGEVSDFVP-EDHLPKRLLAQTDPMTQY-ALAAAEWALRESGCSPSS--
KCLFACT     RFDVSRYPATLAGQIDDFHA-PDHIPGRLLPQTDPSTRL-ALTAADWALQDAKADPES-L
KCLFHIR     RFDPTGYPAELAGQVLDFDA-TEHLPKRLLPQTDVSTRF-ALAAAAWALADAEVDPAE-L
KCLFGRA     RFDASRYPSRLAGQIDDFEA-SEHLPSRLLPQTDVSTRY-ALAAADWALADAGVGPESGL
KCLFNOG     RFDAGRYPSKLAGEVPGFVP-EDHLPSRLMPQTDHMTRL-ALVAADWAFQDAAVDPSK-L
KCLFTCM     RFDPHGYPVRVGGEVLAFDA-AAHLPGRLLPQTDRMTQH-ALVAAEWALADAGLEPEK-Q
KCLFCIN     RFDPSGYPAQLAGEIPGFRA-AEHLPGRLVPQTDRVTRL-SLAAADWALADAGVEVAA-F
KCLFVNZ     RFDPTGYPARLAGEVPGFAA-EEHLPSRLLPQTDRMTRL-ALVAADWALADAGVRPEE-Q
KCLFWHIE    REGCAHLPLRVAGEVHGFDA-AETVEDRFLVQTDRFTHF-ALSATQHALADARFGRADVD
KSGRA       FFDASPFRSRIAGEI-DFDAVAEGFSPREVRRMDRATQF-AVACTRDALADSGLDTGA-L
KSHIR       FFDPTPNRSQIAAEC-DFDPEHEGLSPREIRRMDRAAQF-AVVCTRDAVADSGLEFEQ-V
KSACT       FFDPSPYRSQVAAEA-DFDPVAEGFGPRELDRMDRASQF-AVACAREAFAASGLDPDT-L
KSCIN       FFDPAPFRSKVAAEA-DFCGLENGLSPQEVRRMDRAAQF-AVVTAR-AVEDSGAELAA-H
KSVNZ       FFDPTPFRSRVAAEI-DFDPEAHGLSPQEIRRMDRAAQF-AVVAAR-AVADSGIDLAA-H
KSNOG       AFDPSPFRSRIAAEC-DFDPLAEGLTPQQIRRMDRATQF-AVVSARESLEDSGLDLGA-L
KSTCM       LFDAAPYRSRIAGEI-DFDPIGEGLSPRQASTYDRATQL-AVVCAREALKDSGLDPAA-V
KSDAU       TFDATPFRSRIAAEC-DFDPVAAGLSAEQARRLDRAGQF-ALVAGQEALTDSGLRIGE-D
KSPEU       TFDATPFRSRIAAEC-DFDPVAAGLSAEQARRLDRAGQF-ALVAGQEALADSGLRIDE-D
KSWHI       LFDPSGLRSQIAAEC-DFEPSDHGLGLATAQRCDRYVQF-ALVAASEAVRDANLDMNR-E
              :..:   *    .         *   :  ::    :. :
```

Fig. 2A

```
KCLFDAU    -PLEAGVITASASGGFASGQRELQNLWSKG-----PAHVSAYMSFAWFY-AVNTGQIAIR
KCLFPEU    -PLEAGVITASASGGFAFGQRELQNLWSKG-----PAHVSAYMSFAWFY-AVNTGQIAIR
KCLFACT    TDYDMGVVTANACGGFDFTHREFRKLWSEG-----PKSVSVYESFAWFY-AVNTGQISIR
KCLFHIR    PEYGTGVITSNATGGFEFTHREFRKLWAQG-----PEFVSVYESFAWFY-AVNTGQISIR
KCLFGRA    DDYDLGVVTSTAQGGFDFTHREFHKLWSQG-----PAYVSVYESFAWFY-AVNTGQISIR
KCLFNOG    PEYGVGVVTASSAGGFEFGHRELQNLWSLG-----PQYVSAYQSFAWFY-AVNTGQVSIR
KCLFTCM    DEYGLGVLTAAGAGGFEFGQREMQKLWGTG-----PERVSAYQSFAWFY-AVNTGQISIR
KCLFCIN    DPLDMGVVTASHAGGFEFGQDELQKLLGQG-----QPVLSAYQSFAWFY-AVNSGQISIR
KCLFVNZ    DDFDMGVVTASASGGFEFGQGELQKLWSQG-----SQYVSAYQSFAWFY-AVNSGQISIR
KCLFWHIE   SPYSVGVVTAAGSGGGEFGQRELQNLWGHG-----SRHVGPYQSIAWFY-AASTGQVSIR
KSGRA      DPSRIGVALGSAVASATSLENEYLVMSDSGREWLVDPAHLSPMMFDYLSPGVMPAEVAWA
KSHIR      PPERIGVSLGSAVAAATSLEQEYLVLSDGGREWQVDPAYLSAHMFDYLSPGVMPAEVAWT
KSACT      DPARVGVSLGSAVAAATSLEREYLLLSDSGRDWEVDAAWLSRHMFDYLVPSVMPAEVAWA
KSCIN      PPHRIGVVVGSAVGATMGLDNEYRVVSDGGRLDLVDHRYAVPHLYNYLVPSSFAAEVAWA
KSVNZ      DPYRVGVTVGSAVGATMGLDEEYRVVSDGGRLDLVDHAYAVPHLYDYMVPSSFSAEVAWA
KSNOG      DASRTGVVVGSAVGCTTSLEEEYAVVSDSGRNWLVDDGYAVPHLFDYFVPSSIAAEVAHD
KSTCM      NPERIGVSIGTAVGCTTGLDREYARVSEGGSRWLVDHTLAVEQLFDYFVPTSICREVAWE
KSDAU      SAHRVGVCVGTAVGCTQKLESEYVALSAGGANWVVDPHRGAPELYDYFVPSSLAAEVAWL
KSPEU      SAHRVGVCVGTAVGCTQKLESEYVALSAGGAHWVVDPGRGSPELYDYFVPSSLAAEVAWL
KSWHI      DPWRAGATLGTAVGGTTRLEHDYVLVSERGSRWDVDDRRSEPHLERAFTPATLSSAVAEE
            *.   .    ↓   .:  :    *                  :        ::

KCLFDAU    -HDLRGPVGVVVAEQAGGLDALAHAR-RKVRGGAE-LIVSGAMDSSLCP-YGMAAQVRSG
KCLFPEU    -HDLRGPVGVVVAEQAGGLDALAHAR-RKVRGGAE-LIVSGAVDSSLCP-YGMAAQVKSG
KCLFACT    -HGMRGPSSALVAEQAGGLDALGHAR-RTIRRGTP-LVVSGGVDSALDP-WGWVSQIASG
KCLFHIR    -HGLRGPGSVLVAEQAGGLDAVGHGG--AVRNGTP-MVVTGGVDSSFDP-WGWVSHVSSG
KCLFGRA    -NTMRGPSAALVGEQAGGLDAIGHAR-RTVRRGPG-WCSAVASTRRSTR-GASSSQLSGG
KCLFNOG    -HGLRGPGGVLVTEQAGGLDALGQAR-RQLRRGLP-MVVAGAVDGSPCP-WGWVAQLSSG
KCLFTCM    -HGMRGHSSVFVTEQAGGLDAAAHAA-RLLRKGTLNTALTGGCEASLCP-WGLVAQIPSG
KCLFCIN    -HGMKGPSGVVVSDQAGGLDALAQAR-RLVRKGTP-LIVCGAVEPRSAPGAGSPSSPAGG
KCLFVNZ    -NGMKGPSGVVVSDQAGGLDAVAQAR-RQIRKGTR-LIVSGGVDASLCP-WGWVAHVASD
KCLFWHIE   -NDFKGPCGVVAADEAGGLDALAHAA-LAVRNGTD-TVVCGATEAPLAP-YSIVCQLGYP
KSGRA      -AGAEGPVTMVSDGCTSGLDSVGYAV-QGTREGSADVVVAGAADTPVSPIVVACFDAIKA
KSHIR      -VGAEGPVAMVSDGCTSGLDSLSHAC-SLIAEGTTDVMVAGAADTPITPIVVSCFDAIKA
KSACT      -VGAEGPVTMVSTGCTSGLDSVGNAV-RAIEEGSADVMFAGAADTPITPIVVACFDAIRA
KSCIN      -VGAEGPSTVVSTGCTSGIDAVGIAV-ELVREGSVDVMVAGAVDAPISPIP-CVLDAIKA
KSVNZ      -VGAEGPNTVVSTGCTSGLDSVGYARGELIREGSADVMIAGSSDAPISPITMACFDAIKA
KSNOG      RIGAEGPVSLVSTGCTSGLDAVGYGT-DLIAEGAADVMLAGATEAPISPITVACFDAIKA
KSTCM      -AGAEGPVTVVSTGCTSGLDAVGYGT-ELIRDGRADVVVCGATDAPISPITVACFDAIKA
KSDAU      -AGAEGPVNIVSAGCTSGIDSIGYAC-ELIREGTVDVMLAGGVDAPIAPITVACFDAIRV
KSPEU      -AGAEGPVNIVSAGCTSGIDSIGYAC-ELIREGTVDAMVAGGVDAPIAPITVACFDAIRA
KSWHI      -FGVRGPVQTVSTGCTSGLDAVGYAY-HAVAEGRVDVCLAGAADSPISPITMACFDAIKA
            .*   .*:*: ..  ↑      *              .

KCLFDAU    RLSGSDDPTAGYLPFDRRAAGHVPGEG-GAILAVEDAERVAERG-GKVYGSIAGT-ASFD
KCLFPEU    RLSGSDNPTAGYLPFDRRAAGHVPGEG-GAILTVEDAERAAERG-AKVYGSIAGYGASFD
KCLFACT    RISTATDPDRAYLPFDERAAGYVPGEG-GAILVLEDSAAAEARGRHDAYGELAGCASTFD
KCLFHIR    RVSRATDPGRAYLPFDVAANGYVPGEG-GAILLLEDAESAKARG-ATGYGEIAGYAATFD
KCLFGRA    LVSTVADPERAYLPFDVDASGYVPGEG-GAVLIVEDADSARARG---AERIYVRSPLRRD
KCLFNOG    GLSTSDDPRRAYLPFDAAAGGHVPGEG-GALLVLESDESARARGVTRWYGRIDGYAATFD
KCLFTCM    FLSEATDPHDAYLPFDARAAGYVPGEG-GAMLVAERADSARERDAATVYGRIAGHASTFD
KCLFCIN    -MSDSDEPNRAYLPFDRDGRGYVPGGGRGVVPPLERAEAAPARG-AEVYGE-AGPLARL-
KCLFVNZ    RLSTSEEPARGYLPFDREAQGHVPGEG-GAILVMEAAEAARERG-ARIYGEIAGYGSTFD
KCLFWHIE   ELSRATEPDRAYRPFTEAACGFAPAEG-GAVLVVEEEAAARERG-ADVRATVAGHAATFT
```

Fig. 2B

```
KSGRA      TTPRNDDPAHASRPFDGTRNGFVLAEG-AAMFVLEEYEAAQRRG-AHIYAEVGGYATRSQ
KSHIR      TTPRNDDPEHASRPFDNSRNGFVLAEG-AALFVLEELEHARARG-AHVYAEISGCATRLN
KSACT      TTARNDDPEHASRPFDGTRDGFVLAEG-AAMFVLEDYDSALARG-ARIHAEISGYATRCN
KSCIN      TTPRHDAPATASRPFDSTRNGFVLGEG-AAFFVLEELHSARRRG-AHIYAEIAGYATRSN
KSVNZ      TTNRYDDPAHASRPFDGTRNGFVLGEG-AAVFVLEELESARARG-AHIYAEIAGYATRSN
KSNOG      TTPRNDTPAEASRPFDRTRNGFVLGEG-AAVFVLEEFEHARRRG-ALVYAEIAGFATRCN
KSTCM      TSANNDDPAHASRPFDRNRDGFVLGEG-SAVFVLEELSAARRRG-AHAYAEVRGFATRSN
KSDAU      TSDHNDTPETLA-PFSRSRNGFVLGEG-GAIVVLEEAEAAVRRG-ARIYAEIGGYASRGN
KSPEU      TSDHNDTPETASRPFSRSRNGFVLGEG-GAIVVLEEAEAAVRRG-ARIYAEIGGYASRGN
KSWHI      TSPNNDDPAHASRPFDADRNGFVMGEG-AAVLVLEDLEHARARG-ADVYCEVSGYATFGN
                *   **      *... *  ...    *        . *.

KCLFDAU    -PPPGSGRP---SALARAVETALADAGLDRSDIAVVFADGAA-VGELDVAEAEALASVFG
KCLFPEU    -PPPGSGRP---SALARAVETALADAGLDGSDIAVVFADGAA-VPELDAAEAEALASVFG
KCLFACT    -PAPGSGRP---AGLERAIRLALNDAGTGPEDVDVVFADGAG-VPELDAAEARAIGRVFG
KCLFHIR    -PAPGSERP---PALRRAIELALADAELRPEQVDVVFADAAG-VAELDAIEAAAIRELFG
KCLFGRA    -PAPGSGRP---PALGRAAELALAEAGLTPADISVVFADGAG-VPELDRAEADTLARLFG
KCLFNOG    -PPPGSGRP---PNLLRAAQAALDDAEVGPEAVDVVFADASG-TPDEDAAEADAVRRLFG
KCLFTCM    -ARPGTGRP---TGPARAIRLALEEARVAPEDVDVVYADAAG-VPALDRAEAEALAEVFG
KCLFCIN    -PAPHSGRG---STRAHAIRTALDDAGTAPGDIRRVFADGGGRYPN-DRAEAEAISEVFG
KCLFVNZ    -PRPGSGRE---PGLRKAIELALADAGAAPGDIDVVFADAAA-VPELDRVEAEALNAVFG
KCLFWHIE   GAGRWAESR---EGLARAIQGALAEAGCRPEEVDVVFADALG-VPEADRAEALALADALG
KSGRA      -AYHMTGLKKDGREMAESIRAALDEARLDRTAVDYVNAHGSG-TKQNDRHETAAFKRSLG
KSHIR      -AYHMTGLKTDGREMAEAIRVALDLARIDPTDIDYINAHGSG-TKQNDRHETAAFKRSLG
KSACT      -AYHMTGLKADGREMAETIRVALDESRTDATDIDYINAHGSG-TRQNDRHETAAYKRALG
KSCIN      -AYHMTGLR-DGAEMAEAIRLALDEARLNPEQVDYINAHGSG-TKQNDRHETAAFKKALG
KSVNZ      -AYHMTGLRPDGAEMAEAIRVALDEARMNPTEIDYINAHGSG-TKQNDRHETAAFKKSLG
KSNOG      -AFHMTGLRPDGREMAEAIGVALAQAGKAPADVDYVNAHGSG-TRQNDRHETAAFKRSLG
KSTCM      -AFHMTGLKPDGREMAEAITAALDQARRTGDDLHYINAHGSG-TRQNDRHETAAFKRSLG
KSDAU      -AYHMTGLRADGAEMAAAITAALDEARRDPSDVDYVNAHGTA-TRQNDRHETSAFKRSLG
KSPEU      -AYHMTGLRADGAEMAAAITAALDEARRDPSDVDYVNAHGTA-TKQNDRHETSAFKRSLG
KSWHI      -AYHMTGLTKEGLEMARAIDTALDMAELDGSAIDYVNAHGSG-TQQNDRHETAAVKRSLG
              .  :       :  **   :     :  :*. .     *   *: :      :*
```

Fig. 2C

```
KCLFDAU    P--HRVPVTVPKTLTGRLYSGAGPLDVATGLLALRDEVVPATGHVH-PDPDLPLDVVTGR
KCLFPEU    P--RRVPVTVPKTLTGRLYSGAGPLDVATALLALRDEVVPATAHVD-PDPDLPLDVVTGR
KCLFACT    R--EGVPVTVPKTTTGRLYSGGGPLDVVTALMSLREGVIAPTAGVTSVPREYGIDLVLGE
KCLFHIR    P--SGVPVTAPKTMTGRLYSGGGPLDLVAALLAIRDGVIPPTVHTAEPVPEHQLDLVTGD
KCLFGRA    P--RGVPVTAPKALTGRLCAGGGPADLAAALLALRDQVIPATGRHRAVPDAYALDLVTGR
KCLFNOG    P--YGVPVTAPKTMTGRLSAGGAALDVATALLALREGVVPPTVNVSRPRPEYELDLVLA-
KCLFTCM    P--GAVPVTAPKTMTGRLYAGGAALDVATALLSIRDCVVPPTVGTGAPAPGLGIDLVLHQ
KCLFCIN    P--GRVPVTCPRTMTGRLHSGAAPLDVACALLAMRAGVIPPTVHID-PCPEYDLDLVLYQ
KCLFVNZ    T--GAVPVTAPKTMTGRLYSGAAPLDLAAAFLAMDEGVIPPTVNVE-PDAAYGLDLVVGG
KCLFWHIE   PHAARVPVTAPKTGTGRAYCAAPVLDVATAVLAMEHGLIPPTPHVL--DVCHDLDLVTGR
KSGRA      EHAYAVPVSSIKSMGGHSLGAIGSIEIAASVLAIEHNVVPPTANLHTPDPECDLDYVPLT
KSHIR      EHAYRTPVSSIKSMVGHSLGAIGSIEVAACALAIEHGVVPPTANLHEPDPECDLDYVPLT
KSACT      EHARRTPVSSIKSMVGHSLGAIGSLEIAACVLALEHGVVPPTANLRTSDPECDLDYVPLE
KSCIN      EHAYRTPVSSIKSMVGHSLGAIGSIEIAASALAMEYDVVPPTANLHTPDPECDLDYVPLT
KSVNZ      DHAYRTPVSSIKSMVGHSLGAIGSIEIAASALAMEHNVVPPTGNLHTPDPECDLDYVR-S
KSNOG      DHAYRVPVSSIKSMIGHSLGAIGSLEIAASVLAITHDVVPPTANLHEPDPECDLDYVPLR
KSTCM      QRAYDVPVSSIKSMIGHSLGAIGSLELAACALAIEHGVIPPTANYEEPDPECDLDYVPNV
KSDAU      DHAYRVPISSVKSMIGHSLGAAGSLEVAATALAVEYGAIPPTANLHDPDPELDLDYVPLT
KSPEU      EHAYRVPISSIKSMIGHSLGAVGSLEVAATALAVEYGVIPPTANLHDPDPELDLDYVPLT
KSWHI      EHAYATPMSSIKSMVGHSLGAIGSIELAACVLAMAHQVVPPTANYTTPDPECDLDYVPRE
                   .*::   ::   *:    .      ::.     :::       :...*      :* *

KCLFDAU    PRAMADARAALVVARGHGGFNSALVVRGAA-------
KCLFPEU    PRSLADARAALLVARGYGGFNSALVVRGAA-------
KCLFACT    PRSTAPRTA-LVLARGRWGFNSAAVLRRFAPTP----
KCLFHIR    PRHQQLGTA-LVLARGKWGFNSAVVVRGVTG------
KCLFGRA    PREAALSAA-LVLARGRHGFNSAVVVTLRGSDHRRPT
KCLFNOG    PRRTPLARA-LVLARGRGGFNAAMVVAGPRAETR---
KCLFTCM    PRELRVDTA-LVVARGMGGFNSALVVRRHG-------
KCLFCIN    VRPAALRTA-LGGARGHGGFNSALVVRAGQ-------
KCLFVNZ    PRTAEVNTA-LVIARGHGGFNSAMVVRSAN-------
KCLFWHIE   ARPAEPRTA-LVLARGLMGSNSALVLRRGAVPPEGR-
KSGRA      AREQRVDTV-LTVGSGFGGFQSAMVLHRPEEAA----
KSHIR      AREQRVDTV-LSVGSGFGGFQSAMVLRRLGGANS---
KSACT      ARERKLRSV-LTVGSGFGGFQSAMVLRDAETAGAAA-
KSCIN      ARDQRVDSV-LTVGSGFGGFQSAMVLTSAQ---RSTV
KSVNZ      CREQLTDSV-LTVGSGFGGFQSAMVLARPE---RKIA
KSNOG      ARACPVDTV-LTVGSGFGGFQSAMVLCGPGSRGRSAA
KSTCM      AREQRVDTV-LSVGSGFGGFQSAAVLARPKETRS---
KSDAU      AREKRVRHA-LTVGSGFGGFQSAMLLSRPER------
KSPEU      AREKRVRHA-LTVGSGFGGFQSAMLLSRLER------
KSWHI      ARERTLRHV-LSVGSGFGGFQSAVVLSGSEGGLR---
             *        .  *    . *     *  ::*  ::

mole:~/ks2%
```

Fig. 2D

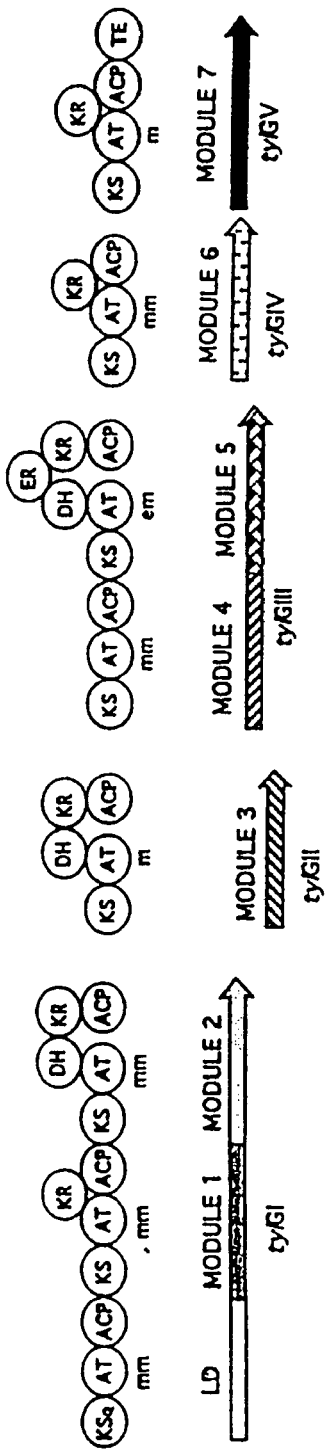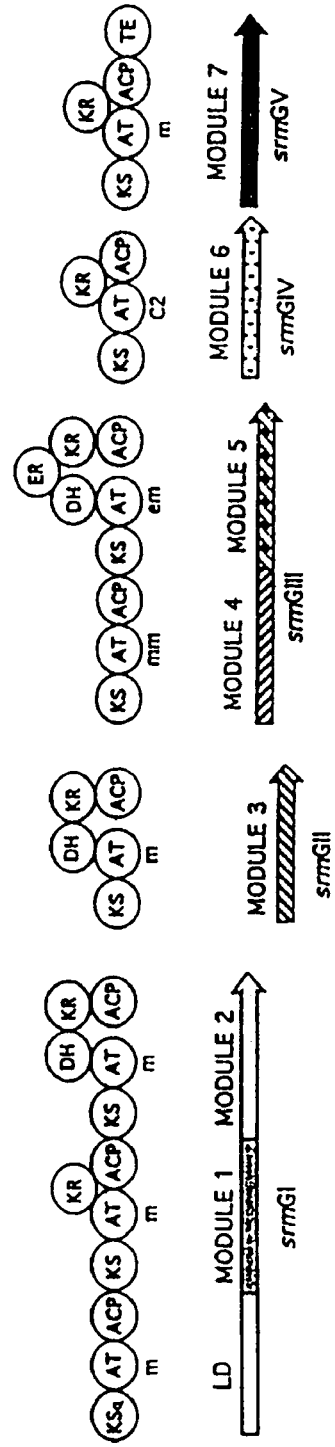
Fig. 3A

```
                        1                                                           50
niddamycin     --------- ---------- MAGHGDATAQ KAQDAEKSED GSDAIAVIGM
platenolide    --------- ---------- --------MS GELAISRSDD RSDAVAVVGM
monensin       --------- ---------- ------MAAS ASASPSGPSA GPDPIAVVGM
oleandomycin-- --------- ---------- ---------- ---MHVPGEE NGHSIAIVGI
tylosin        MSSALRRAVQ SNCGYGDLMT SNTAAQNTGD QEDVDGPDST HGGEIAVVGM 51                                                          100
niddam...      SCRFPGAPGT AEFWQLLSSG ADAVVTAADG RRR....... .....GTIDA
platenol.      ACRFPGAPGI AEFWKLLTDG RDAIGRDADG RRR....... .....GMIEA
monensin       ACRLPGAPDP DAFWRLLSEG RSAVSTAPPE RRRADSGLHG P...GGYLDR
oleandom       ACRLPGSATP QEFWRLLADS ADALDEPPAG RFPTGSLSSP PAPRGGFLDS
tylosin        SCRLPGAAGV EEFWELLRSG RGMPTRQDDG TWRAA..... .......LED 101                                                         150
niddam...      PADFDAAFFG MSPREAAATD PQQRLVLELG WEALEDAGIV PESLRGEAAS
platenol.      PGDFDAAFFG MSPREAAETD PQQRLMLELG WEALEDAGIV PGSLRGEAVG
monensin       IDGFDADFFH ISPREAVAMD PQQRLLLELS WEALEDAGIR PPTLARSRTG
oleandom       IDTFDADFFN ISPREAGVLD PQQRLALELG WEALEDAGIV PRHLRGTRTS
tylosin        HAGFDAGFFG MNARQAAATD PQHRLMLELG WEALEDAGIV PGDLTGTDTG 151                                                         200
niddam...      VFVGAMNDDY ATLLH.RAGA PTDTYTATGL QHSMIANRLS YFLGLRGPSL
platenol.      VFVGAMHDDY ATLLH.RAGA PVGPHTATGL QRAMLANRLS YVLGTRGPSL
monensin       VFVGAFWDDY TDVLNLRAPG AVTRHTMTGV HRSILANRIS YAYHLAGPSL
oleandom       VFMGAMWDDY AHLAHARGEA ALTRHSLTGT HRGMIANRLS YALGLQGPSL
tylosin        VFAGVASDDY A.VLTRRSAV SAGGYTATGL HRALAANRLS HFLGLRGPSL 201                                                         250
niddam...      VVDTGQSSSL VAVALAVESL RGGTSGIALA GGVNLVLAEE GS.AAMERVG
platenol.      AVDTAQSSSL VAVALAVESL RAGTSRVAVA GGVNLVLADE GT.AAMERLG
monensin       TVDTAQSSSL VAVHLACESI RSGDSDIAFA GGVNLICSPR TTELAAARFG
oleandom       TVDTGQSSSL AAVHMACESL ARGESDLALV GGVNLVLDPA GT.TGVERFG
tylosin        VVDSAQSASL VAVQLACESL RRGETSLAVA GGVNLILTEE ST.TVMERMG 251                                                         300
niddam...      ALSPDGRCHT FDARANGYVR GEGGAIVVLK PLADALADGD RVYCVVRGVA
platenol.      ALSPDGRCHT FDARANGYVR GEGGAAVVLK PLADALADGD PVYCVVRGVA
monensin       GLSAAGRCHT FDARADGFVR GEGGGLVVLK PLAAARRDGD TVYCVIRGSA
oleandom       ALSPDGRCYT FDSRANGYAR GEGGVVVVLK PTHRALADGD TVYCEILGSA
tylosin        ALSPDGRCHT FDARANGYVR GEGGGAVVLK PLDAALADGD RVYCVIKGGA 301                                                         350
niddam...      TGNDGGGPGL TVPDRAGQEA VLRAACDQAG VRPADVRFVE LHGTGTPAGD
platenol.      VGNDGGGPGL TAPDREGQEA VLRAACAQAR VDPAEVRFVE LHGTGTPVGD
monensin       VNSDGTTDGI TLPSGQAQQD VVRLACRRAR ITPDQVQYVE LHGTGTPVGD
oleandom       LNNDGATEGL TVPSARAQAD VLRQAWERAR VAPTDVQYVE LHGTGTPAGD
tylosin        VNNDGGGASL TTPDREAQEA VLRQAYRRAG VSTGAVRYVE LHGTGTRAGD
```

Fig. 4A

```
              351                                                        400
niddam...     PVEAEALGAV YGTGRP..AN EPLLVGSVKT NIGHLEGAAG IAGFVKAALC
platenol.     PVEAHALGAV HGSGRP..AD DPLLVGSVKT NIGHLEGAAG IAGLVKAALC
monensin      PIEAAALGAA LGQDAA..RA VPLAVGSAKT NVGHLEAAAG IVGLLKTALS
oleandom      PVEAEGLGTA LGTARP..AE APLLVGSVKT NIGHLEGAAG IAGLLKTVLS
tylosin       PVEAAALGAV LGAGADSGRS TPLAVGSVKT NVGHLEGAAG IVGLIKATLC 401                                                        450
niddam...     LHERALPASL NFETPNPAIP LERLRLKVQT AHAALQPGTG GGPLLAGVSA
platenol.     LRERTLPGSL NFATPSPAIP LDQLRLKVQT AAAELPLAPG GAPLLAGVSS
monensin      IHHRRLAPSL NFTTPNPAIP LADLGLTVQQ DLADWP..RP EQPLIAGVSS
oleandom      IKNRHLPASL NFTSPNPRID LDALRLRVHT AYGPWP..SP DRPLVAGVSS
tylosin       VRKGELVPSL NFSTPNPDIP LDDLRLRVQT ERQEW.NEED DRPRVAGVSS 451                                                        500
niddam...     FGMGGTNCHV VLEETPGG.. .......... .......... ...RQPAE.T
platenol.     FGIGGTNCHV VLEHLPSR.. .......... .......... ...PTPAV.S
monensin      FGMGGTNGHV VVA....AAP DSVAVPEPVG VPERVEVPEP VVVSEPVVVP
oleandom      FGMGGTNCHV VLSELRNAGG DGAGKGPYTG TEDRLGATEA EKRPDPATGN
tylosin       FGMGGTNVHL VIAEAPAAAG SSGAGGSGAG SGAGISAVSG VV........

501                                                        550
niddam...     GQADACLFSA SPMLLLSARS EQALRAQAAR LREHL..EDS GADPLDIAYS
platenol.     VAAS...LPD VPPLLLSARS EGALRAQAVR LGETV..ERV GADPRDVAYS
monensin      TPWP...... .....VSAHS ASALRAQAGR LRTHLAAHRP TPDAARVGHA
oleandom      GPDPAQDTHR YPALILSARS DAALRAQAER LRHHL.EHSP GQRLRDTAYS
tylosin       .......... ..PVVVSGRS RVVVREAAGR LAE..VVEAG GVGLADVAVT 551                                                        600
niddam...     LATTRTRFEH RAAVPCGDPD RLSSALAALA AGQTPRGVRI GS..TDADGR
platenol.     LASTRTLFEH RAVVPCGGRG ELVAALGGFA AGRVSGGVRS GR..A.VPGG
monensin      LATTRAPLAH RAVLLGGDTA ELLGSLDALA EGAETASIVR GEAYT..EGR
oleandom      LATRRQVFER HAVVTGHDRE DLLNGLRDLE NGLPAPQVLL GRTPTPEPGG
tylosin       MAD.RSRFGY RAVVLARGEA ELAGRLRALA GGDPDAGVVT G...AVLDGG 601                                                        650
niddam...     LALLFTGQGA QHPGHGQELY TTDPHFAAAL DEVCEELQRC GTQNLREVMF
platenol.     VGVLFTGQGA QWVGMGRGLY AGGGVPAEVL DEVLSMVGEV DGRSLRDVMF
monensin      TAFLFSGQGA QRLGMGRELY AVFPVFADAL DEAFAALDVH LDRPLREIVL
oleandom      LAFLFSGQGS QQPGMGKRLH QVFPGFRDAL DEVCAELDTH LGRLL.....
tylosin       VVVGAAPGGA GAAGGAGAAG GAGGGVVLV FPGQGTQWVG MGAGLLGSSE 651                                                        700
niddam...     TPDQPD.... .......... .......... LLDRTEYTQP ALFALQTALY
platenol.     GDVDVDAGAG ADAGAGAGAG VGSGSGSVGG LLGRTEFAQP ALFALEVALF
monensin      GETDSGGNVS GENVIGEGA. ......DHQA LLDQTAYTQP ALFAIETSLY
oleandom      .GPEAGPPLR DVMFAERGT. ......AHSA LLSETHYTQA ALFALETALF
tylosin       VFAASMRECA RALSVHVGWD LLEVVSGGAG .LERVDVVQP VTWAVMVSLA 701                                          ↓  750
niddam...     RTLTARGTQA HLVLGHSVGE ITAAHIAGVL DLPDAARLIT ARAHVMGQLP
platenol.     RALEARGVEV SVVLGHSVGE VAAATVAGVL SLGDAVRLVV ARGGLMGGLP
monensin      RLAASFGLKP DYVLGHSVGE IAAAHVAGVL SLPDASALVA TRGRLMQAVR
oleandom      RLLVQWGLKP DHLAGHSVGE IAAAHAAGIL DLSDAAELVA TRGALMRSLP
tylosin       RYWQAMGVDV AAVVGHSQGE IAAATVAGAL SLEDAAAVVA LRAGLIGRYL
                                                          ↑
```

Fig. 4B

```
              751                                                        800
niddam...     HG.GAMLSVQ  AAEHDLDQLA  HTHG..VEIA  AVNGPTHCVL  SGPRTALEET
platenol.     VG.GGMWSVG  ASESVVRGVV  EGLGEWVSVA  AVNGPRSVVL  SGDVGVLESV
monensin      AP.GAMAAWQ  ATADEAAEQL  AGHERHVTVA  AVNGPDSVVV  SGDRATVDEL
oleandom      GG.GVMLSVQ  APESEVAPLL  LGREAHVGLA  AVNGPDAVVV  SGERGHVAAI
tylosin       AGRGAMAAVP  LPAGEVEAGL  .AKWPGVEVA  AVNGPASTVV  SGDRRAVAGY 801                                                        850
niddam...     AQHLREQNVR  HTWLKVSHAF  HSALMDPMLG  AFRDTLNTLN  Y..QPPTIPL
platenol.     VASLMGDGVE  YRRLDVSHGF  HSVLMEPVLG  EFRGVVESLE  FGRVRPGVVV
monensin      TAAWRGRGRK  AHHLKVSHAF  HSPHMDPILD  ELRAVAAGLT  FHE..PVIPV
oleandom      EQILRDRGRK  SRYLRVSHAF  HSPLMEPVLE  EFAEAVAGLT  FRA..PTTPL
tylosin       VAVCQAEGVQ  ARLIPVDYAS  HSRHVEDLKG  ELERVLSGI.  .RPRSPRVPV 851                                                        900
niddam...     ISNLTGQIA.  .....DPNHL  CTPDYWIDHA  RHTVRFADAV  QTAHHQGTTT
platenol.     VSGVSGGVV.  .....GSGEL  GDPGYWVRHA  REAVRFADGV  GVVRGLGVGT
monensin      VSNVTGELVT  ATATGSGAGQ  ADPEYWARHA  REPVRFLSGV  RGLCERGVTT
oleandom      VSNLTG....  ..APVDDRTM  ATPAYWVRHV  REAVRFGDGI  RALGKLGTGS
tylosin       CSTVAGEQPG  EPVF......  .DAGYWFRNL  RNRVEFSAVV  GGLLEEGHRR 901                                                        950
niddam...     YLEIGPHPTL  TTLLHHTL..  .DNP......  ..........T  TIPTLHRERP
platenol.     LVEVGPHGVL  TGMAGECLGA  GDDV......  ..........V  VVPAMRRGRA
monensin      FVELGPDAPL  SAMARDCFPA  P.........  .ADRSRPRPA  AIATCRRGRD
oleandom      FLEVGPDGVL  TAMARACVTA  APEPGHRGEQ  GADADAHTAL  LLPALRRGRD
tylosin       FIEVSAHPVL  V.........  .....HAIEQ  TAEAADRSVH  ATGTLRRQDD 951
niddam...     EPETLTQAIA  AVGVRTDGID  WAVLCGASRP  RRVELPTYAF
platenol.     EREVFEAALA  TVFTRDAGLD  ATALHTGSTG  RRIDLPTTPF
monensin      EVATFLRSLA  QAYVRGADVD  FTRAYGATAT  RRFPLPTYPF
oleandom      EARSLTEAVA  RLHLHGVPMD  WTSVLGGDVS  .RVPLPTYAF
tylosin       SPHRLLTSTA  EAWAHGATLT  WDPAL..PPG  HLTTLPTYPF
``` niddam: niddamycin; platenol: platenolide I (spiramycin); oleandom: oleandomycin.

Fig. 4C forward (P1f):

5'-CTA GGC CGG GCC GGA CTG GTA GAT CTG CCT ACG TAT CCT TTC CAG GGC AAG CGG TTC TGG CTG CAG CCG GAC CGC ACT AGT CCT CGT GAC GAG

GGA GAT GCA TCG AGC CTG AGG GAC CGG TT-3' backward (P1b):

5'-AAC CGG TCC CTC AGG CTC GAT GCA TCT CCC TCG TCA CGA GGA CTA GTG CGG TCC GGC TGC AGC CAG AAC CGC TTG CCC TGG AAA GGA TAC GTA

GGC AGA TCT ACC AGT CCG GCC CGG C-3' oligos annealed:

CTAGGCCGGGCCGGACTGGTAGATCTGCCTACGTATCCTTTCCAGGGCAAGCGGTTCTGGCTGCAGCCGGACCGCACTAGTCCTCGTGACGAGGGAGATGCATCGAGCCTGAGGGACCGGTT
    CGGCCCGGCCTGACCATCTAGACGGATGCATAGGAAAGGTCCCGTTCGCCAAGACCGACGTCGGCCTGGCGTGATCAGGAGCACTGCTCCCTCTACGTAGCTCGGACTCCCTGGCCAA

-----    -----      -----      -----      -----      -----      -----
AvrII   BglII   SnaBI    PstI    SpeI    NsiI    Bsu36I   HpaI

Figure 7

HYBRID POLYKETIDE SYNTHASES AND NOVEL LOADING DOMAINS

The present invention relates to processes and materials (including enzyme systems, nucleic acids, vectors and cultures) for preparing novel polyketides, particularly 12-, 14- and 16-membered ring macrolides, by recombinant synthesis and to the novel polyketides so produced. Polyketide biosynthetic genes or portions of them, which may be derived from different polyketide biosynthetic gene clusters are manipulated to allow the production of specific novel polyketides, such as 12-, 14- and 16-membered macrolides, of predicted structure. The invention is particularly concerned with the replacement of genetic material encoding the natural starter unit with other genes in order to prepare macrolides with preferentially an acetate starter unit; or preferentially a propionate unit; or preferentially with an unusual starter unit, in each case minimising the formation of by-products containing a different starter unit.

Polyketides are a large and structurally diverse class of natural products that includes many compounds possessing antibiotic or other pharmacological properties, such as erythromycin, tetracyclines, rapamycin, avermectin, monensin, epothilones and FK506. In particular, polyketides are abundantly produced by *Streptomyces* and related actinomycete bacteria. They are synthesised by the repeated stepwise condensation of acylthioesters in a manner analogous to that of fatty acid biosynthesis. The greater structural diversity found among natural polyketides arises from the selection of (usually) acetate or propionate as "starter" or "extender" units; and from the differing degree of processing of the β-keto group observed after each condensation. Examples of processing steps include reduction to β-hydroxyacyl-, reduction followed by dehydration to 2-enoyl-, and complete reduction to the saturated acylthioester. The stereochemical outcome of these processing steps is also specified for each cycle of chain extension.

The biosynthesis of polyketides is initiated by a group of chain-forming enzymes known as polyketide synthases. Two classes of polyketide synthase (PKS) have been described in actinomycetes. One class, named Type I PKSs, represented by the PKSs for the macrolides erythromycin, oleandomycin, avermectin and rapamycin, consists of a different set or "module" of enzymes for each cycle of polyketide chain extension. For an example see FIG. 1 (Cortés, J. et al. Nature (1990) 348:176–178; Donadio, S. et al. Science (1991) 2523:675–679; Swan, D. G. et al. Mol. Gen. Genet. (1994) 242:358–362; MacNeil, D. J. et al. Gene (1992) 115:119–125; Schwecke, T. et al. Proc. Natl. Acad. Sci. USA (1995) 92:7839–7843).

The term "extension module" as used herein refers to the set of contiguous domains, from a β-ketoacyl-ACP synthase ("KS") domain to the next acyl carrier protein ("ACP") domain, which accomplishes one cycle of polyketide chain extension. The term "loading module" is used to refer to any group of contiguous domains which accomplishes the loading of the starter unit onto the PKS and thus renders it available to the KS domain of the first extension module. The length of polyketide formed has been altered, in the case of erythromycin biosynthesis, by specific relocation using genetic engineering of the enzymatic domain of the erythromycin-producing PKS that contains the chain releasing thioesterase/cyclase activity (Cortés et al. Science (1995) 268:1487–1489; Kao, C. M. et al. J. Am. Chem. Soc. (1995) 117:9105–9106).

In-frame deletion of the DNA encoding part of the ketoreductase domain in module 5 of the erythromycin-producing PKS (also known as 6-deoxyerythronolide B synthase, DEBS) has been shown to lead to the formation of erythromycin analogues 5,6-dideoxy-3-α-mycarosyl-5-oxoerythronolide B, 5,6-dideoxy-5-oxoerythronolide B and 5,6-dideoxy, 6 β-epoxy-5-oxoerythronolide B (Donadio, S. et al. Science (1991) 252:675–679). Likewise, alteration of active site residues in the enoylreductase domain of module 4 in DEBS, by genetic engineering of the corresponding PKS-encoding DNA and its introduction into *Saccharopolyspora erythraea*, led to the production of 6,7-anhydroerythromycin C (Donadio, S. et al. Proc Natl. Acad. Sci. USA (1993) 90:7119–7123).

International Patent Application number WO 93/13663 describes additional types of genetic manipulation of the DEBS genes that are capable of producing altered polyketides. However many such attempts are reported to have been unproductive (Hutchinson, C. R. and Fujii, I. Annu. Rev. Microbiol. (1995) 49:201–238, at p. 231). The complete DNA sequence of the genes from *Streptomyces hygroscopicus* that encode the modular Type I PKS governing the biosynthesis of the macrocyclic immunosuppressant polyketide rapamycin has been disclosed (Schwecke, T. et al. (1995) Proc. Natl. Acad. Sci. USA 92:7839–7843). The DNA sequence is deposited in the EMBL/Genbank Database under the accession number X86780.

The second class of PKS, named Type II PKSs, is represented by the synthases for aromatic compounds. Type II PKSs contain only a single set of enzymatic activities for chain extension and these are re-used as appropriate in successive cycles (Bibb, M. J. et al. EMBO J. (1989) 8:2727–2736; Sherman, D. H. et al. EMBO J. (1989) 8:2717–2725; Fernandez-Moreno, M. A. et al. J. Biol. Chem. (1992) 267:19278–19290). The "extender" units for the Type II pKSs are usually acetate units, and the presence of specific cyclases dictates the preferred pathway for cyclisation of the completed chain into an aromatic product (Hutchinson, C. R. and Fujii, I. Annu. Rev. Microbiol. (1995) 49:201–238). Hybrid polyketides have been obtained by the introduction of clones Type II PKS gene-containing DNA into another strain containing a different Type II PKS gene cluster, for example by introduction of DNA derived from the gene cluster for actinorhodin, a blue-pigmented polyketide from *Streptomyces coelicolor*, into an anthraquinone polyketide-producing strain of *Streptomyces galileus* (Bartel, P. L. et al. J. Bacteriol. (1990) 172:4816–4826).

The minimal number of domains required for polyketide chain extension on a Type II PKS when expressed in a *Streptomyces coelicolor* host cell (the "minimal PKS") has been defined for example in International Patent Application Number WO 95/08548 as containing the following three polypeptides which are products of the act I genes: first KS; secondly a polypeptide termed the CLF with end-to-end amino acid sequence similarity to the KS but in which the essential active site residue of the KS, namely a cysteine residue, is substituted either by a glutamine residue, or in the case of the PKS for a spore pigment such as the whiE gene product (Chater, K. F. and Davis, N. K. Mol. Microbiol. (1990) 4:1679–1691) by a glutamic acid residue (FIG. 2); and finally an ACP. The CLF has been stated for example in International Patent Application Number WO 95/08548 to be a factor that determines the chain length of the polyketide chain that is produced by the minimal PKS. However it has been found (Shen, B. et al. J. Am. Chem. Soc. (1995) 117:6811–6821) that when the CLF for the octaketide actinorhodin is used to replace the CLF for the decaketide tetracenomycin in host cells of *Streptomyces glaucescens*, the polyketide product is not found to be altered from a decaketide to an octaketide, so the exact role of the CLF remains unclear. An alternative nomenclature has been proposed in which KS is designated KSα and CLF is designated KSβ, to reflect this lack of knowledge (Meurer, G. et al. Chemistry and Biology (1997) 4:433–443). The mechanism by which acetate starter units and acetate extender units are loaded onto the Type II PKS is not known, but it is speculated that the malonyl-CoA: ACP acyltransferase of the fatty acid synthase of the host cell can fulfil the same function for the Type II PKS (Revill, W. P. et al. J. Bacteriol. (1995) 177:3946–3952).

International Patent Application Number WO 95/08548 describes the replacement of actinorhodin PKS genes by heterologous DNA from other Type II PKS gene clusters, to obtain hybrid polyketides. The same International Patent Application WO 95/08548 describes the construction of a strain of *Streptomyces coelicolor* which substantially lacks the native gene cluster for actinorhodin, and the use in that strain of a plasmid vector pRM5 derived from the low-copy number vector SCP2* isolated from *Streptomyces coelicolor* (Bibb, M. J. and Hopwood, D. A. J. Gen. Microbiol. (1981) 126:427) and in which heterologous PKS-encoding DNA may be expressed under the control of the divergent act I/act III promoter region of the actinorhodin gene cluster (Fernandez-Moreno, M. A. et al. J. Biol. Chem. (1992) 267:19278–19290). The plasmid pRM5 also contains DNA from the actinorhodin biosynthetic gene cluster encoding the gene for a specific activator protein, ActII-orf4. The Act II-orf4 protein is required for transcription of the genes placed under the control of the actI/act II bidirectional promoter and activates gene expression during the transition from growth to stationary phase in the vegetative mycelium (Hallam, S. E. et al. Gene (1988) 74:305–320).

Type II clusters in *Streptomyces* are known to be activated by pathway-specific activator genes (Narva, K. E. and Feitelson, J. S. J. Bacteriol. (1990) 172:326–333; Stutzman-Engwall, K. J. et al. J. Bacteriol. (1992) 174:144–154; Fernandez-Moreno, M. A. et al. Cell (1991) 66:769–780; Takano, E. et al. Mol. Microbiol. (1992) 6:2797–2804; Takano, E. et al. Mol. Microbiol. (1992) 7:837–845), The DnrI gene product complements a mutation in the actII-orf4 gene of *S. coelicolor*, implying that DnrI and ActII-orf4 proteins act on similar targets. A gene (srmR) has been described (EP 0 524 832 A2) that is located near the Type I PKS gene cluster for the macrolide polyketide spiramycin. This gene specifically activates the production of the macrolide antibiotic spiramycin, but no other examppples have been found of such a gene. Also, no homologues of the ActII-orf4/DnrI/RedD family of activators have been described that act on Type I PKS genes.

Although large numbers of therapeutically important polyketides have been identified, there remains a need to obtain novel polyketides that have enhanced properties or possess completely novel bioactivity. The complex polyketides produced by Type I PKSs are particularly valuable, in that they include compounds with known utility as anthelminthics, insecticides, immunosuppressants, antifungal or antibacterial agents. Because of their structural complexity, such novel polyketides are not readily obtainable by total chemical synthesis, or by chemical modifications of known polyketides.

There is also a need to develop reliable and specific ways of deploying individual modules in practice so that all, or a large fraction, of hybrid PKS genes that are constructed, are viable and produce the desired polyketide product.

Pending International Patent Application number PCT/GB97/01819 discloses that a PKS gene assembly (particularly of Type I) encodes a loading module which is followed by at least one extension module. Thus FIG. 1 shows the organisation of the DEBS genes. The first open reading frame encodes the first multi-enzyme or cassette (DEBS 1) which consists of three modules: the loading module (eryload) and two extension modules (modules 1 and 2). The loading module comprises an acyltransferase and an acyl carrier protein. This may be contrasted with FIG. 1 of WO 93/13663 (referred to above). This shows ORF1 to consist of only two modules, the first of which is in fact both the loading module and the first extension module.

PCT/GB97/01819 describes in general terms the production of a hybrid PKS gene assembly comprising a loading module and at least one extension module. PCT/GB97/01818 also describes (see also Marsden, A. F. A. et al. Science (1998) 279:199–202) construction of a hybrid PKS gene assembly by grafting the wide-specificity loading module for the avermectin-producing polyketide synthase onto the first multienzyme component (DEBS 1) for the erythromycin PKS in place of the normal loading module. Certain novel polyketides can be prepared using the hybrid PKS gene assembly, as described for example in pending International Patent Application number (PCT/GB97/01810). Patent Application PCT/GB97/01819 further describes the construction of a hybrid PKS gene assembly by grafting the loading module for the rapamycin-producing polyketide synthase onto the first multienzyme component (DEBS 1) for the erythromycin PKS in place of the normal loading module. The loading module of the rapamycin PKS differs from the loading modules of DEBS and the avermectin PKS in that it comprises a CoA ligase domain, an enoylreductase ("ER") domain and an ACP, so that suitable organic acids including the natural starter unit 3,4-dihydroxycyclohexane carboxylic acid may be activated in situ on the PKS loading domain, and with or without reduction by the ER domain transferred to the ACP for intramolecular loading of the KS of extension module 1 (Schwecke, T. et al. Proc. Natl. Acad. Sci. USA (1995) 92:7839–7843).

The DNA sequences have been disclosed for several Type I PKS gene clusters that govern the production of 16-membered macrolide polyketides, including the tylosin PKS from *Streptomyces fradiae* (EP 0 791 655 A2), the niddamycin PKS from *Streptomyces caelestis* (Kavakas, S. J. et al. J. Bacteriol. (1998) 179:7515–7522) and the spiramycin PKS from *Streptomyces ambofaciens* (EP 0791 655 A2). All of these gene sequences have in common that they show the loading module of the PKS to differ from the loading module of DEBS and of the avermectin PKS in that they consist of a domain resembling the KS domains of the extension modules, an AT domain and an ACP (FIG. 3). The additional N-terminal KS-like domain has been named KSq because it differs in each case from an extension KS by the specific replacement of the active site cysteine residue essential for β-ketoacyl-ACP synthase activity by a glutamine (Q in single letter notation) residue. The function of the KSq domain is unknown (Kavakas, S. J. et al. J. Bacteriol. (1998) 179:7515–7522), but its presence in these PKSs for 16-membered macrolides is surprising because the starter units of tylosin, niddamycin and spiramycin appear to be propionate, acetate and acetate respectively, that is, the same type of starter unit as in DEBS. The AT adjacent to the KSq domain is named here the ATq domain.

When the entire loading module of the tylosin PKS was used to replace the analogous loading module in the spiramycin PKS in *S. ambofaciens* (Kuhstoss et al. Gene (1996)

183:231–236), the nature of the starting unit was stated to be altered from acetate to propionate. Since the role of the KSq domain was not understood, no specific disclosure was made that revealed either the importance of the KSq domain, or the possible utility of these KSq-containing loading modules in ensuring the purity of the polyketide product in respect of the starter unit, even at high levels of macrolide production. The interpretation for their results was stated as: "Therefore we believe that the experiments described here provide strong experimental support for the hypothesis that the AT domains in Type I PKS systems select the appropriate substrate AT each step in synthesis" (Kuhstoss et al. Gene (1996) 183:231–236, at p. 235). These authors noted the analogy with the CLF protein in Type II PKS systems and that the latter protein is thought to be involved in determining the chain length. They state: "KSq may serve a similar function, although it is unclear why such a function would be necessary in the synthesis of these 16-membered polyketides when it is not needed for the synthesis of other complex polyketides such as 6-DEB or rapamycin. In any case the KSq is unlikely to be involved in substrate choice AT each step of synthesis." (Kuhstoss et al. Gene (1996) 183:231–236).

It has been shown that when genetic engineering is used to remove the loading module of DEBS, the resulting truncated DEBS in *S. erythraea* continues to produce low levels of erythromycins containing a propionate starter unit (Pereda, A. et al. Microbiology (1995) 144:543–553). The same publication shows that when in this truncated DEBS the methylmalonyl-CoA -specific AT of extension module 1 was replaced by a malonyl-CoA-specific AT from an extension module of the rapamycin PKS, the products were also low levels of erythromycins containing a propionate starter unit, demonstrating that the origin of the starter units is not decarboxylation of the (methyl)malonyl groups loaded onto the enzyme by the AT of module 1, but from direct acylation of the KS of extension module 1 by propionyl-CoA. This is in contrast to a previous report, using partially purified DEBS1+TE, a truncated bimodular PKS derived from DEBS (Kao, C. M. et al. J. Am. Chem. Soc. (1995) 117: 9105–9106) and functionally equivalent to DEBS1-TE (Brown, M. J. B. et al., J. Chem. Soc. Chem. Commun. (1995) 1517–1518; Cortés, J. et al. Science (1991) 2523: 675–679), which stated that the origins of the starter units for DEBS can include methylmalonate units which are loaded onto module 1 and are decarboxylated by the KS of module 1 (Pieper, R. et al. Biochemistry (1997) 36:1846–1851). It has now been found that when the DEBS1-TE protein is fully purified from extracts of recombinant *S. erythraea* it contains no such specific decarboxylase activity (Weissmann, K. et al. *Biochemistry*, (1998) 37, 11012–11017), further confirming that starter units do not in fact arise from decarboxylation of extension units mediated by the KS of extension module 1.

It is known that the DEBS loading module has a slightly broader specificity than propionate only, and in particular acetate starter units are used both in vitro and in vivo, when the PKS containing this loading module is part of a PKS that is expressed either in *S. erythraea* the natural host for erythromycin production (see for example Cortés, J. et al. Science (1995) 268:1487–1489), or in a heterologous host such as *S. coelicolor* (Kao, C. M. et al. J. Am. Chem. Soc. (1994) 116:11612–11613; Brown, M. J. B. et al. J. Chem. Soc. Chem. Commun. (1995) 1517–1519). In vitro experiments using purified DEBS1-TE have demonstrated that propionyl-CoA and acetyl-CoA are alternative substrates that efficiently supply propionate and acetate units respectively to the loading module (Wiessmann, K. E. H. et al. Chemistry and Biology (1995) 2:583–589; Pieper, R. et al. J. Am. Chem. Soc. (1995) 117:11373–11374). The outcome of the competition between acetate and propionate starter units is influenced by the respective intracellular concentrations of propionyl-CoA and acetyl-CoA prevailing in the host cell used (see for example Kao, C. M. et al. Science (1994) 265:509–512; Pereda, A. et al. Microbiology (1995) 144:543–553). It is also determined by the level of expression of the host PKS, so that as disclosed for example in Pending International Patent Application number PCT/GB97/01819, when recombinant DEBS or another hybrid PKS containing the DEBS loading module is over-expressed in *S. erythraea*, the products are generally mixtures whose components differ only in the presence of either an acetate or a propionate starter unit.

There is a need to develop reliable methods for avoiding the formation of mixtures of polyketides with both acetate and propionate starter units, and to allow the specific incorporation of unusual starter units. It has now been found, surprisingly, that the role of the loading domains in the PKSs for the 16-membered macrolides tylosin, niddamycin and spiramycin is different from that of the loading domains of the avermectin PKS and of DEBS. It has been realised that the KSq domain of the tylosin PKS and the associated AT domain, which is named here ATq, together are responsible for the highly specific production of propionate starter units because the ATq is specific for the loading of methylmalonyl-CoA and not propionyl-CoA as previously thought; and the KSq is responsible for the highly specific decarboxylation of the enzyme-bound methylmalonate unit to form propionate unit attached to the ACP domain of the loading module and appropriately placed to be transferred to the KS of extension module 1 for the initiation of chain extension. In a like manner the ATq of the spiramycin and niddamycin PKSs, and the adjacent KSq, are responsible for the specific loading of malonate units rather than acetate units as previously believed, and for their subsequent specific decarboxylation to provide acetate starter units for polyketide chain extension.

It has also now been found here that not only the PKSs for the above-mentioned 16-membered macrolides, but also the PKSs for certain 14-membered macrolides particularly the oleandomycin PKS from *Streptomyces antibioticus* (FIG. 4) and also the PKSs for certain polyether ionophore polyketides particularly the putative monensin PKS from *Streptomyces cinnamonensis* (FIG. 4), possess a loading domain comprising a KSq domain, an ATq domain, and an ACP. In FIG. 4 is shown a sequence alignment of the KSq domains and of the adjacent linked ATq domains that have been identified, showing the conserved active site glutamine (Q) residue in the KSq domains, and an arginine residue which is conserved in all extension AT domains and is also completely conserved in ATq domains. This residue is characteristically not arginine in the AT domains of either DEBS or of the avermectin PKS loading modules, where the substrate for the AT is a non-carboxylated acyl-CoA ester (Haydock, S. F. et al. FEBS Letters (1995) 374:246–248). The abbreviation ATq is used here to simply to distinguish the AT domains found immediately C-terminal of Ksq from extension ATs, and the label has no other significance.

In one aspect the invention provides a PKS multienzyme or part thereof, or nucleic acid (generally DNA) encoding it, said multienzyme or part comprising a loading module and a plurality of extension modules, wherein (a) the loading module is adapted to load a malonyl or substituted malonyl residue and then to effect decarboxylation of the loaded residue to provide an acetyl or substituted acetyl (which term encompasses propionyl) residue for transfer to an extension module; and (b) the extension modules, or at least one thereof (preferably at least the one adjacent the loading module), are not naturally associated with a loading module that effects decarboxylation of an optionally substituted malonyl residue.

Generally the loading module will also include an ACP (acyl carrier protein) domain.

Preferably the decarboxylating functionality of the loading module is provided by a KS (ketosynthase)-type domain. Suitably this differs from a KS of a conventional extension module by possessing a glutamine residue in place of the essential cysteine residue in the active site. It is termed Ksq. It may be "natural" or genetically engineered, e.g. resulting from site-directed mutagenesis of nucleic acid encoding a different KS such as a KS of an extension module.

Alternatively the decarboxylating functionality can be provided by a CLF-type domain of the general type occuring in Type II PKS systems.

Preferably the loading functionality is provided by an AT (acyltransferase)-type domain which resembles an AT domain of a conventional extension module in having an arginine residue in the active site, which is not the case with the AT domains of loader modules which load acetate or propionate, e.g. in DEBS or avermectin PKS systems. It may be termed Atq. Once again, it may be "natural" or genetically engineered, e.g. by mutagenesis of an AT of an extension module.

Usually the loading module will be of the form:
KSq-ATq-ACP where ACP is acyl carrier protein.

In another aspect the invention provides a method of synthesising a polyketide having substantially exclusively a desired starter unit by providing a PKS multienzyme incorporating a loading module as defined above which specifically provides the desired starter unit. This may comprise providing nucleic acid encoding the multienzyme and introducing it into an organism where it can be expressed.

In further aspects the invention provides vectors and transformant organisms and cultures containing nucleic acid encoding the multienzyme. A preferred embodiment is a culture which produces a polyketide having a desired starter unit characterised by the substantial absence of polyketides with different starter units. Thus, for example, erythromycin can be produced substantially free from analogues resulting from the incorporation of acetate starter units in place of propionate.

Preferably the hybrid PKS encodes a loading module and from 2 to 7 extension modules and a chain terminating enzyme (generally a thioesterase).

It is particularly useful to provide a loading module of the type KSq-ATq-ACP for a PKS gene assembly which produces a 12-, 14- or 16-membered macrolide in order to prepare a 12-, 14- or 16-membered macrolide which contains exclusively or almost exclusively an acetate starter unit, even when such PKS gene assembly is expressed at high levels in an actinomycete host cell. Particularly suitable PKSs for this purpose are the components of PKSs for the biosynthesis of erythromycin, methymycin, oleandomycin, tylosin, spiramycin, midecamycin, and niddamycin for all of which the gene and modular organisation is known at least in part. Particularly suitable sources of the genes encoding a loading module of the type KSq-ATq-ACP are the loading modules of oleandomycin, spiramycin, niddamycin, methymycin and monensin which are specific for the loading of malonate units which are then decarboxylated to acetate starter units.

Similarly it is particularly useful to provide a loading module of the type KSq-ATq-ACP for a PKS gene assembly which produces the macrolides rifamycin, avermectin, rapamycin, immunomycin and FK506 whose loading modules possess an unusual specificity (and for all of which the gene and modular organisation is known at least in part) in order to prepare such macrolides containing exclusively or almost exclusively an acetate starter unit, even when such PKS gene assembly is expressed at high levels in an actinomycete host cell. Particularly suitable sources of the genes encoding a loading module of the type KSq-ATq-ACP are the loading modules of oleandomycin, spiramycin, niddamycin, methymycin and monensin which are specific for the loading of malonate units which are decarboxylated to acetate starter units.

It is similarly useful to provide a loading module of the type KSq-ATq-ACP for a PKS gene assembly which produces a 12-, 14- or 16-membered macrolide in order to prepare a 12-, 14- or 16-membered macrolide which contains exclusively or almost exclusively a propionate starter unit, even when such PKS gene assembly is expressed at high levels in an actinomycete host cell. Particularly suitable PKSs for this purpose are the components of PKSs for the biosynthesis of erythromycin, methymycin, oleandomycin, tylosin, spiramycin, midecamycin, and niddamycin for all of which the gene and modular organisation is known at least in part. A particularly suitable source of the genes encoding a loading module of the type KSq-ATq-ACP is the loading module of tylosin which is specific for the loading of methylmalonate units which are decarboxylated to propionate starter units.

Similarly it is particularly useful to provide a loading module of the type KSq-ATq-ACP for a PKS gene assembly which produces the macrolides rifamycin, avermectin, rapamycin, immunomycin and FK506 whose loading modules possess an unusual specificity (and for all of which the gene and modular organisation is known at least in part) in order to prepare such macrolides containing exclusively or almost exclusively a propionate starter unit, even when such PKS gene assembly is expressed at high levels in an actinomycete host cell. A particularly suitable source of the genes encoding a loading module of the type KSq-ATq-ACP is the loading module of tylosin which is specific for the loading of methylmalonate units which are decarboxylated to propionate starter units.

In the loading module of the type KSq-ATq-ACP the domains or portions of them may be derived from the same or from different sources, and comprise either natural or engineered domains. For example the ATq domain can be replaced by an AT domain derived from any extension module of a Type I PKS, having specificity either for loading of malonate units or for loading of methylmalonate units respectively, so long as the KSq domain is chosen to have a matching specificity towards either methylmalonate or malonate units respectively.

Alternatively, the KSq domain in the loading module provided of the type KSq-ATq-ACP may be substituted by the CLF polypeptide of a Type II PKS. It is now apparent that in contrast to its previous identification as a factor uniquely determining chain length, the CLF, in addition to any other activities that it may possess, is the analogue of the KSq domain and can act as a decarboxylase towards bound malonate units.

The appreciation that the CLF domain of Type II PKS's has decarboxylating activity has led us to devise useful interventions in Type II systems, e.g. to enhance the yields obtainable in some fermentations. Many high-yielding industrial fermentations tend to give mixtures, owing to the incorporation of undesired starters. This is particularly the case in systems which have auxiliary genes for generating unusual starters. CLF genes may act to produce undesired acyl species, leading to products incorporating the undesired acyl units.

For example the production of oxytetracycline involves an unusual malonamido starter. However the undesired activity of a CLF domain causes some decarboxylation, leading to the incorporation of acetyl instead. Daunomycin synthesis likewise involves an unusual starter which is liable to the "parasitic" activity of a CLF domain.

The active site (for decarboxylation) of a CLF domain generally includes a glutamine residue. We find that the decarboxylating activity of the domain can be removed by a mutation by which the Gln residue is converted into (for example) Ala.

Thus in a further aspect the invention provides a system and process for synthesis of a type II (aromatic) polyketide, in which a gln residue of a CLF domain of the type II PKS is mutated to suppress decarboxylation activity. Techniques of site-specific mutagenesis by which this can be achieved are by now well known to those skilled in the art.

The loading module of the type KSq-ATq-ACP may be linked to a hybrid PKS produced for example as in PCT/GB97/01819 and PCT/GB97/01810. It is particularly useful to link such a loading module to gene assemblies that encode hybrid PKSs that produce novel derivatives of 14-membered macrolides as described for example in PCT/GB97/01819 and PCT/GB97/01810.

The invention further provides such PKS assemblies furnished with a loading module of the type KSq-ATq-ACP, vectors containing such assemblies, and transformant organisms that can express them. Transformant organisms may harbour recombinant plasmids, or the plasmids may integrate. A plasmid with an int sequence will integrate into a specific attachment site (att) of the host's chromosome. Transformant organisms may be capable of modifying the initial products, eg by carrying out all or some of the biosynthetic modifications normal in the production of erythromycins (as shown in FIG. 5) and for other polyketides. Use may be made of mutant organisms such that some of the normal pathways are blocked, e.g. to produce products withut one or more "natural" hydroxy-groups or sugar groups. The invention further provides novel polyketides as producible, directly or indirectly, by transformant organisms. This includes polyketides which have undergone enzymatic modification.

In a further aspect the invention provides both previously-obtained polyketides and novel polyketides in a purer form with respect to the nature of the starter unit, than was hitherto possible. These include 12-, 14- and 16-membered ring macrolides which are either "natural" or may differ from the corresponding "natural" compound:

a) in the oxidation state of one or more of the ketide units (ie selection of alternatives from the group: —CO—, —CH (OH)—, alkene —CH—, and —CH$_2$—) where the stereochemistry of any —CH(OH)— is also independently selectable;

b) in the absence of a "natural" methyl side-chain; or c) in the stereochemistry of "natural" methyl; and/or ring substituents other than methyl.

It is also possible to prepare derivatives of 12-, 14- and 16-membered ring macrolides having the differences from the natural product identified in two or more of items a) to c) above.

Derivatives of any of the afore-mentioned polyketides which have undergone further processing by non-PKS enzymes, eg one or more of hydroxylation, epoxidation, glycosylation and methylation may also be prepared The present invention provides a novel method of obtaining both known and novel complex polyketides without the formation of mixtures of products differing only in having either an acetate or a propionate starter unit. In addition the present invention provides a method to obtain novel polyketides in which the starter unit is an unusual starter unit which is derived by the action of a KSq domain on the enzyme-bound product of an AT of unusual specificity derived from an extension module of a natural Type I PKS. In particular the AT of extension module 4 of the FK506 PKS gene cluster preferentially incorporates an allyl side-chain; the AT of extension module 6 of the niddamycin PKS gene cluster preferentially incorporates a sidechain of structure HOCH$_2$—; and the ATs of extension module 5 of spiramycin and of extension module 5 of monensin incorporate an ethyl side chain. In each case the KSq domain is preferentially one that is naturally propionate-specific. Alternatively, any KS from an extension module of a Type I PKS may be converted into a KSq domain capable of decarboxylating a bound carboxylated acyl thioester, by site-directed mutagenesis of the active site cysteine residue to replace it by another residue, preferably glutamine. It is known that the animal fatty acid synthase, which shares many mechanistic features with Type I PKS, in the absence of acetyl-CoA, has a demonstrable malonyl-CoA decarboxylase activity (Kresze, G. B. et al. Eur. J. Biochem. (1977) 79:191–199). When treated with an alkylating agent such as iodoacetamide the fatty acid synthase is inactivated by specific modification of the active site cysteine of the KS, and the resulting protein has an enhanced malonyl-CoA decarboxylase activity. The conversion of a fatty acid KS domain into a decarboxylase mirrors the genetically-determined change between the KS domains and the KSq domain in Type I PKSs. Indeed, the size and polarity characteristics of a glutamine side chain very closely approximate those of carboxamido-cysteine. The KSq to be used for decarboxylation of an unusual alkylmalonate unit is preferably selected from the same extension module of the same Type I PKS that provides the unusual AT, in order to optimise the decarboxylation of the unusual alkylmalonate, and the ACP to be used is preferably also the ACP of the same extension module.

Suitable plasmid vectors and genetically engineered cells suitable for expression of PKS genes incorporating an altered loading module are those described in PCT/GB97/01819 as being suitable for expression of hybrid PKS genes of Type I. Examples of effective hosts are *Saccharopolyspora erythraea, Streptomyces coelicolor, Streptomyces avermitilis, Streptomyces griseofuscus, Streptomyces cinnamonensis, Streptomyces fradiae, Streptomyces longisporoflavus, Streptomyces hygroscopicus, Micromonospora griseorubida, Streptomyces lasaliensis, Streptomyces venezuelae, Streptomyces antibioticus, Streptomyces lividans, Streptomyces rimosus, Streptomyces albus, Amycolatopsis mediterranei,* and *Streptomyces tsukubaensis*. These include hosts in which SCP2*-derived plasmids are known to replicate autonomously, such as for example *S. coelicolor, S. avermitilis* and *S. griseofuscus*; and other hosts such as *Saccharopolyspora erythraea* in which SCP2*-derived plasmids become integrated into the chromosome through homologous recombination between sequences on the plasmid insert and on the chromosome; and all such vectors which are integratively transformed by suicide plasmid vectors.

BRIEF DESCRIPTION OF THE DRAWINGS

Some embodiments of the invention will now be described with reference to the accompanying drawings in which:

FIGS. 2A–2D give the amino acid sequence comparison of the KS domains and the CLF domains of representative Type II PKS gene clusters. The active site Cysteine (C) of the KS domains is arrowed in the Figure and aligns with the Glutamine (Q) or glutamic acid (E) of the CLF domains. The abbreviations used, and the relevant Genbank/EMBL accession numbers are: GRA: granaticin from *Streptomyces violaceoruber* (X63449); HIR: unknown polyketide from *Saccharopolyspora hirsuta* (M98258); ACT, actinorhodin from *Streptomyces coelicolor* (X63449); CIN: unknown polyketide from *Streptomyces cinnamonensis* (Z11511); VNZ: jadomycin from *Streptomyces venezuelae* (L33245); NOG: anthracyclines from *Streptomyces nogalater* (Z48262); TCM: tetracenomycin from *S. glaucescens* (M80674); DAU: daunomycin from *Streptomyces sp.* C5 (L34880); PEU, doxorubicin from *Streptomyces peucetius* (L35560); WHI: WhiE spore pigment from *Streptomyces coelicolor* (X55942). From top to bottom, the sequences are SEQ ID NOs: 1–20, respectively.

FIG. 3A shows the gene organization of the PKSs for the 16-membered ring macrolides tylosin and spiramycin.

FIGS. 4A–4C show the amino acid sequence alignment of KSq-ATq loading didomains of the PKSs for niddamycin (SEQ ID NO: 21), platenolide(spiramycin) (SEQ ID NO: 22), monensin (SEQ ID NO: 23), oleandomycin (SEQ ID NO: 24) and tylosin (SEQ ID NO: 25). The sequences for the monensin and oleandomycin loading didomains have not been previously disclosed. The arrow in FIG. 4B indicates the conserved arginine residue.

FIG. 7 shows the structures of two oligonucleotides. The forward and backward oligonucleotides are SEQ ID NOs: 26 and 27, respectively, and are shown as annealed with restriction enzyme sites.

Figure 1:
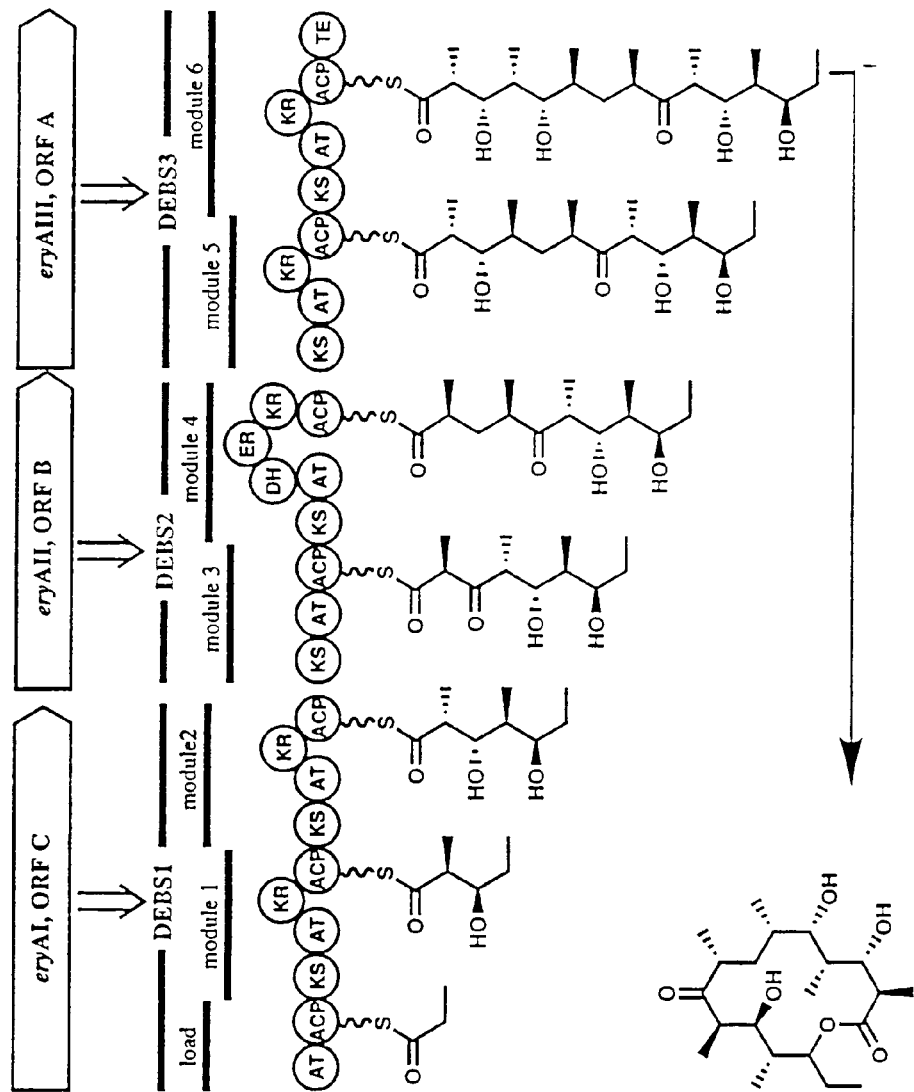
FIG. 1 is a diagram showing the functioning of 6-deoxyetythronolide B synthase (DEBS), a modular PKS producing 6-deoxyerythronolide B (6-DEB) a precursor of erythromycin A.
Figure 3B:
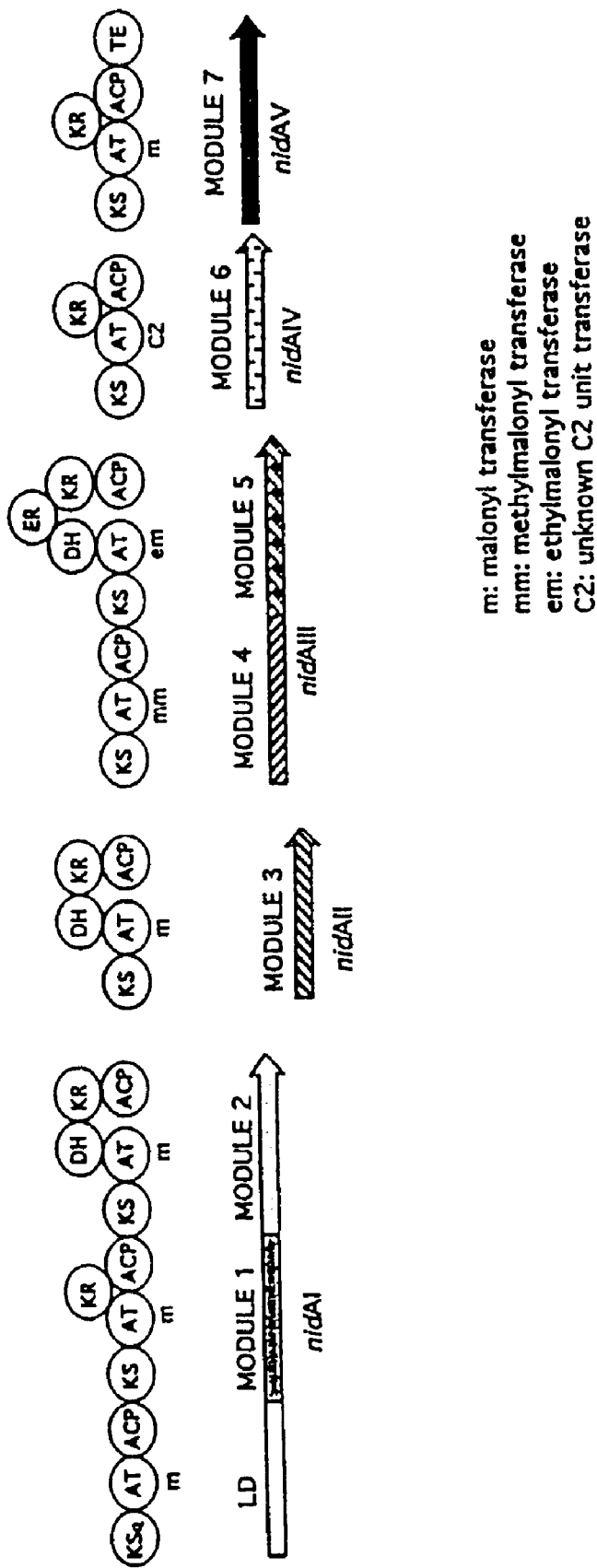
FIG. 3B shows the gene organization of the PKS for the 16-membered ring macrolide niddamycin.

The present invention will now be illustrated, but is not intended to be limited, by means of some examples. All NMR spectra were measured in $CDCl_3$ using a Bruker 500 mHz DMX spectrometer unless otherwise indicated and peak positions are expressed in parts per million (ppm) downfield from tetramethysilane. The atom number shown in the NMR structure is not representative of standard nomenclature, but correlates NMR data to that particular example.

HPLC Methods

| Method 1 | |
|---|---|
| Column | Waters Symmetry 5_C18 2.1 mm × 150 mm |
| Flow | 0.29 ml/mm |
| Mobile phase | Gradient: A:B (22.78) to A:B (38:62) over 12 minutes, then to A:B (80:20) by minute 15. Maintain for 1 minute. Re-equilibrate before next sample. Where A = acetonitrile and B = 0.01M ammonium acetate in 10% acetonitrile and 0.02% TFA |
| Method B | |
| Column | Waters Symmetry 5_C18 2.1 mm × 150 mm |
| Flow | 0.29 ml/mm |
| Mobile phase | Gradient:28:72 acetonitrile: 10 mM NH40Ac to 50:50 in 18 minutes. 50:50 until 25 minutes. back to 28:72, re-equilibrate for 7 minutes |
| Instrument | Acquired with Hewlett Packard 1100 LC/MS with APCI source |

| Tap Water medium | |
|---|---|
| glucose | 5 g/liter |
| tryptone | 5 g/liter |
| yeast extract | 2.5 g/liter |
| EDTA | 36 mg/liter |
| Tap water to 1 L total volume | |

| ERY - P medium | |
|---|---|
| dextrose | 50 g/liter |
| Nutrisoy ™ flour | 30 g/liter |
| $(NH_4)_2SO_4$ | 3 g/liter |
| NaCl | 5 g/liter |
| $CaCO_3$ | 6 g/liter |
| Tap water to 1 L total volume | |
| pH adjusted to 7.0 | |

EXAMPLE 1

Construction of the Recombinant Vector pPFL43

Plasmid pCJR24 was prepared as described in PCT/GB97/01819. pPFL43 is a pCJR24-based plasmid containing the gene encoding a hybrid polyketide synthase that contains the putative monensin PKS loading module (isolated from *S. cinnamonensis*) the DEBS extension modules 1 and 2 and the chain-terminating thioesterase. Plasmid pPFL43 was constructed as follows:

The following synthetic oligonucleotides: 5'-CCATATG-GCCGCATCCGCGTCAGCGT-3' (SEQ ID No. 28) and 5'-GGCTAGCGGGTCCTCGTCCGTGCCGAGGTCA-3' (SEQ ID No. 29) are used to amplify the DNA encoding the putative monensin-producing loading module using a cosmid that contains the 5' end of the putative monensin-producing PKS genes from *S. cinnamonensis* or chromosomal DNA of *S. cinnamonensis* as template. The PCR product of 3.3 kbp is purified by gel electrophoresis, treated with T4 polynucleotide kinase and ligated to plasmid pUC18, which has been linearised by digestion with Sma I and then treated with alkaline phosphatase. The ligation mixture was used to transform electrocompetent *E. coli* DH10B cells and individual clones were checked for the desired plasmid pPFL40. Plasmid pPFL40 was identified by restriction pattern and sequence analysis.

Plasmid pHD30His is a derivative of pNEWAVETE (PCT/GB97/01810) which contains the avermectin loading module, erythromycin extension modules 1 and 2 and the ery thioesterase domain. Plasmid pNEWAVETE was cut with is EcoRI and HinDIII and a synthetic oligonucleotide linker was inserted that encodes the addition of a C-terminal polyhistidine tail to the polypeptide. The following oligonucleotides: 5'-AATTCACATCACCATCACCATCAC-TAGTAGGAGGTCTGGCCATCTAGA-3, (SEQ ID No. 30) and 5'-AGCTTCTAGATGGCCAGACCTCCTAC-TAGTGATGGTGATGGTGATGTG-3' (SEQ ID No. 31) were annealed together and the duplex was ligated to EcoRI-and HinDIII-cut pNEWAVETE. The resulting plasmid was cut with NdeI and XbaI and ligated into plasmid pCJR24 that had been previously cut with same two enzymes, to produce plasmid pND30His.

Plasmid pPFL40 was digested with Nde I and Nhe I and the 3.3 kbp fragment was purified by gel electrophoresis and ligated to pND30-His previously digested with Nde I and Nhe I and treated with alkaline phosphatase. The ligation mixture was used to transform electrocompetent *E. coli* DH10B cells and individual clones were checked for the desired plasmid pPFL43. Plasmid pPFL43 was identified by restriction analysis.

EXAMPLE 2

Construction of *S. erythraea* JC2/pPFL43

Plasmid pPFL43 was used to transform *S. erythraea* JC2 protoplasts. The construction of strain JC2 from which the resident DEBS genes are substantially deleted is given in Pending Patent Application PCT/GB97/01819. Thiostrepton resistant colonies were selected in R2T20 medium containing 10 μg/ml of thiostrepton. Several clones were tested for the presence of pPFL43 integrated into the chromosome by Southern blot hybridisation of their genomic DNA with DIG-labelled DNA containing the mon PKS fragment encoding for the loading module.

EXAMPLE 3

Production of Polyketides Using *S. erythraea* JC2/PPFL43

A frozen suspension of strain *S. erythraea* JC2/pPFL43 was inoculated in eryP medium, containing 5 μg/ml of thiostrepton. The inoculated culture was allowed to grow for seven days at 28–30° C. After this time the broth was filtered to remove mycelia and the pH adjusted to pH=3.0. The broth was extracted twice with two volumes of ethyl acetate and the combined extracts were washed with an equal volume of saturated sodium chloride, dried over anhydrous sodium sulphate, and the ethyl acetate was removed under reduced pressure, to give crude product. The product was shown to have the structure shown below, and by MS, GC-MS and ¹H NMR was found to be identical to an authentic sample.

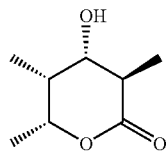

EXAMPLE 4

Construction of *S. erythraea* NRRL2338/pPFL43

Plasmid pPFL43 was used to transform *S. erythraea* NRRL2338 protoplasts. Thiostrepton resistant colonies were selected in R2T20 medium containing 10 μg/ml of thiostrepton. Several clones were tested for the presence of pPFL43 integrated into the chromosome by Southern blot hybridisation of their genomic DNA with DIG-labelled DNA containing the mon PKS fragment encoding for the loading module. A clone with an integrated copy of pPFL43 was selected in this way.

EXAMPLE 5a

Production of 13-methyl-erythromycin A and B using *Sacch. erythraea* NRRL 2338/pPFL43

The culture *Saccharopolyspora erythraea* NRRL2338 (pPFL43), constructed with the wild-type loading domain displaced by a monensin loader-D1TE DNA insert, produced as described in Example 2, was inoculated into 30 ml Tap Water medium with 50 ug/ml thiostrepton in a 300 ml Erlenmeyer flask. After three days incubation at 29° C., this flask was used to inoculate 300 ml of ERY-P medium in a 300 ml flask. The broth was incubated at 29° C. at 200 rpm for 6 days. After this time, the whole broth was adjusted to pH 8.5 with NaOH, then extracted with equal volume of ethyl acetate. The ethyl acetate extract was evaporated to dryness at 45° C. under a nitrogen stream using a Zymark TurboVap LV Evaporator, then reconstituted in 0.0625 volumes methanol to concentrate the extract 16-fold. The structures of the products were confirmed by LC/MS, Method A. A 4.0 min retention time peak was observed as the major component, with m/z value of 720 (M+H)⁺, required for 13-methyl-erythromycin A. A second peak was observed with a retention time of 6.4 min and with m/z value of 704 (M+H)⁺, required for 13-methyl-erythromycin B.

EXAMPLE 5b

Production and Recovery of 13-methyl-erythromycin A and B using *Sacch. erythraea* NRRL-2338 (pPFL43) at 8L Scale

*Saccharopolyspora erythraea* NRRL2338 (pPFL43) was inoculated into 1000 mls Tap Water medium with 50 ug/ml thiostrepton in a 2.8l Fernbach flask. After three days incubation at 29° C., this flask was used to inoculate 8l of ERY-P medium in a 14l Microferm fermentor jar (New Brunswick Scientific Co., Inc., Edison, N.J.). The broth was incubated at 28° C. with an aeration rate of 8l/min, stirring at 800 rpm and with pH maintained between 6.9 and 7.3 with NaOH or H₂SO₄ (15%). Water was added to maintain volume at the 24 hour volume level. The fermentation was continued for 167 hours. After this time, presence of 13-methyl- erythromycin A and B were confirmed by adjusting a broth sample from the fermentor to pH 8.5 with NaOH, then extracting with equal volume of ethyl acetate. The ethyl acetate extract was evaporated to dryness at 45° C. under a nitrogen stream using a Zymark TurboVap LV Evaporator, then reconstituted in 0.25 volumes methanol to concentrate the extract 4-fold. The structures of the products were confirmed by LC/MS, Method A. A 4.1 min retention time peak was observed as the major component, with m/z value of 720 (M+H)⁺, required for 13-methyl-erythromycin A. A second peak was observed with a retention time of 6.6 min and with m/z value of 704 (M+H)⁺, required for 13-methyl-erythromycin B.

About 35 liters of broth containing approximately 2.8 grams of 13-methyl- erythromycin A were processed for recovery of product. Broth was filtered through a pilot sized Ceraflo ceramic unit and loaded onto a 500 ml XAD-16 resin column. The product was eluted using 100% methanol. A 175 ml CG-161 adsorption column was prepared and equilibrated with 20% methanol/water. A portion of the product solution was adjusted to 20% methanol and loaded onto the column, no breakthrough of product was observed. Washing of the column with up to 40% methanol/water failed at removing any significant level of impurities. Elution with 50% methanol/water achieved chromatographic separation of the product from the two major impurities, 13-methyl-erythromycin B and a degradation product, 13-methyl-dehydroerythromycin A. The purest cuts were combined and reduced in volume by approximately 75% using evaporation to achieve <10% methanol concentration. To enhance 13-methyl-erythromycin A extraction, solid sodium bicarbonate was added until a total concentration of 250 mM was obtained. The aqueous product layer was extracted 2× with methylene chloride, using one-half the total volume each time. The volume was reduced to light yellow solids by evaporation. The 13-methyl-erythromycin A was purified by dissolving the crude crystals into methylene chloride at ambient temperature and diluting to 15% methylene chloride with hexane. The cloudy solution is placed at −10° C. for ~30 minutes when the liquid is decanted to a $2^{nd}$ flask, leaving the majority of impurities behind as an oil. The flask is left overnight at −10° C., followed by filtration of off-white 13-methyl-erythromycin A crystals the next day. Approximately 300 milligrams of 13-methyl-erythromycin A were isolated from the partial work-up of the 35l broth volume.

Approximately 100 grams of evaporated mother liquor were utilized further to isolate 13-methyl-erythromycin B. Residual 13-methyl-erythromycin A was removed with repetitive extraction of the initial sample with aqueous acetic acid (pH 5). The subsequent methylene chloride layer was chromatographed on 700 g of silica gel using 20% methanol in methylene chloride. The 13-methyl-erythromycin B enriched fractions, as determined by LC/MS, were combined and evaporated to yield ~11.0 grams of dark oil. The oil was dissolved in a minimal amount of methanol and loaded onto 500 ml of Amberchrom CG-161 resin. The 13-methyl-erythromycin B was eluted at 2 bed volumes per hour with 40% methanol in deionized water. One bed volume fractions were collected and assayed by LC/MS. Fractions 42 through 62 were combined, diluted to ~20% methanol with deionized water, and neutralized to pH 7.5 with sodium bicarbonate. The resulting solution was extracted once with 4l of methylene chloride, concentrated to ~500 ml, and dried over anhydrous magnesium sulfate. After removal of the MgSO4 by filtration the filtrate was evaporated to give ~110 mg of light brown solids. The 110 mg of crude 13-methyl-erythromycin B was dissolved in ~3.0 milliliters of HPLC grade acetonitrile and loaded onto a 20 cm×20 cm, 2 mm thick, silica gel preparative thin layer chromatography (PTLC) plate. The plate was developed with 60:40 methanol:acetonitrile. The desired portion of silica from the PTLC plate (iodine visualisation) was removed and extracted with HPLC grade acetone. The acetone extract was evaporated to give 12.1 mg of clear solid.

Identification of the 13-methyl-erythromycin A and 13-methyl-erythromycin B samples were confirmed by mass spectroscopy (LC/MS Method B) and NMR spectroscopy. The 13-methyl-erythromycin A sample peak had a 4.7 min retention time, with m/z value of 720 $(M+H)^+$, required for 13-methyl-erythromycin A. The 13-methyl-erythromycin B sample peak had a 7.6 min retention time, with m/z value of 704 $(M+H)^+$, required for 13-methyl-erythromycin B.

NMR, 13-methyl-erythromycin A:

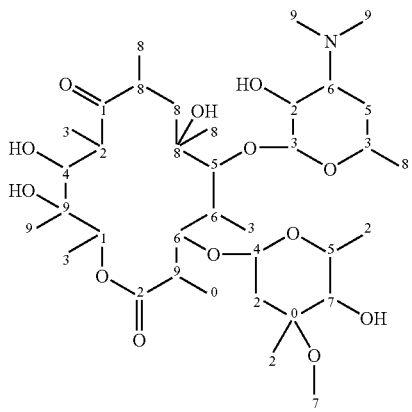

| # | 13C-ppm | #H | 1H-ppm |
|---|---------|----|--------|
| 1 | 221.91 | 0 | |
| 2 | 175.99 | 0 | |
| 3 | 103.63 | 1 | 4.45 |
| 4 | 96.81 | 1 | 4.88 |
| 5 | 83.76 | 1 | 3.60 |
| 6 | 79.86 | 1 | 4.10 |
| 7 | 78.36 | 1 | 3.05 |
| 8 | 75.50 | 0 | |
| 9 | 74.87 | 0 | |
| 10 | 73.07 | 0 | |
| 11 | 72.25 | 1 | 5.19 |
| 12 | 71.25 | 1 | 3.26 |
| 13 | 69.53 | 1 | 3.53 |
| 14 | 69.24 | 1 | 3.97 |
| 15 | 66.16 | 1 | 4.06 |
| 16 | 65.96 | 1 | 2.48 |
| 17 | 49.96 | 3 | 3.36 |
| 18 | 45.36 | 1 | 2.79 |
| 19 | 45.07 | 1 | 2.81 |
| 20 | 40.73 | 3 | 2.32 |
| 21 | 39.00 | 1 | 3.15 |
| 22 | 35.30 | 2 | 2.42/1.61 |
| 24 | 27.20 | 3 | 1.50 |
| 25 | 21.92 | 3 | 1.28 |
| 26 | 21.82 | 3 | 1.27 |
| 27 | 18.99 | 3 | 1.32 |
| 28 | 18.60 | 3 | 1.22 |
| 29 | 16.07 | 3 | 1.19 |
| 30 | 15.08 | 3 | 1.19 |
| 31 | 14.23 | 3 | 1.26 |
| 32 | 12.12 | 3 | 1.19 |
| 33 | 9.60 | 3 | 1.15 |
| 34 | 39.00 | 2 | 1.98/1.75 |
| 35 | 28.90 | 2 | 1.72/1.27 |
| 36 | 40.94 | 1 | 2.05 |

17

NMR, 13-methyl-erythromycin B:

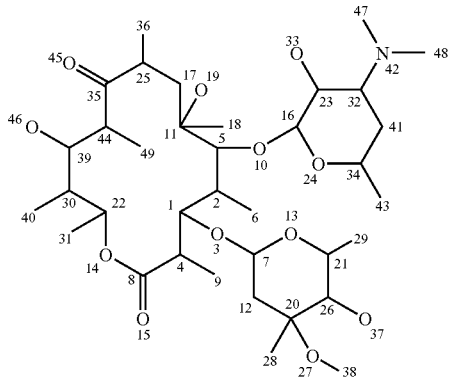

| # | 13C-PPM | #H attached | 1H-PPM |
|---|---------|-------------|--------|
| 1 | 80.50 | 1 | 4.15 |
| 2 | 40.62 | 1 | 2.15 |
| 4 | 45.17 | 1 | 2.84 |
| 5 | 84.08 | 1 | 3.62 |
| 6 | 9.86 | 3 | 1.18 |
| 7 | 97.26 | 1 | 4.88 |
| 8 | 176.48 | 0 | |
| 9 | 15.25 | 3 | 1.22 |
| 11 | 75.98 | 0 | |
| 12 | 35.43 | 2 | 2.42/1.61 |
| 16 | 103.75 | 1 | 4.46 |
| 17 | 38.77 | 2 | 2.09/1.72 |
| 18 | 27.67 | 3 | 1.51 |
| 20 | 73.09 | 0 | |
| 21 | 66.20 | 1 | 4.06 |
| 22 | 70.27 | 1 | 5.58 |
| 23 | 71.24 | 1 | 3.28 |
| 25 | 45.49 | 1 | 2.81 |
| 26 | 78.29 | 1 | 3.06 |
| 28 | 21.91 | 3 | 1.28 |
| 29 | 19.03 | 3 | 1.33 |
| 30 | 41.61 | 1 | 1.65 |
| 31 | 18.73 | 3 | 1.29 |
| 32 | 65.94 | 1 | 2.53 |
| 34 | 69.52 | 1 | 3.55 |
| 35 | 219.92 | 0 | |
| 36 | 19.03 | 3 | 1.21 |
| 38 | 49.97 | 3 | 3.36 |
| 39 | 70.17 | 1 | 3.88 |
| 40 | 9.27 | 3 | 0.95 |
| 41 | 29.12 | 2 | 1.73/1.28 |
| 43 | 21.80 | 3 | 1.27 |
| 44 | 39.87 | 1 | 3.07 |
| 47 | 40.74 | 3 | 2.35 |
| 48 | 40.74 | 3 | 2.35 |
| 49 | 9.62 | 3 | 1.04 |

EXAMPLE 6

Construction of the Recombinant Vector pPFL42

Plasmid pPFL42 is a pCJR24-based plasmid containing the gene encoding a hybrid polyketide synthase that contains the tylosin-producing PKS loading module, the erythromycin extension modules 1 and 2 and the chain-terminating thioesterase. Plasmid pPFL42 was constructed as follows:

The following synthetic oligonucleotides: 5'-CCATAT-GACCTCGAACACCGCTGCACAGAA-3' (SEQ ID No. 54) and 5'-GGCTAGCGGCTCCTGGGCTTC-GAAGCTCTTCT-3' (SEQ ID No. 55) were used to amplify the DNA encoding the tylosin-producing loading module using either cos6T (a cosmid that contains the tylosin-producing PKS genes from *S. fradiae*) or chromosoml DNA from *S. fradiae* as template. The PCR product of 3.3 kbp was purified by gel electrophoresis, treated with T4 polynucleotide kinase and ligated to plasmid pUC18, which had been linearised by digestion with Sma I and then treated with alkaline phosphatase. The ligation mixture was used to transform electrocompetent *E. coli* DH10B cells and individual clones were checked for the desired plasmid PpPFL39. Plasmid pPFL39 was identified by restriction and sequence analysis.

Plasmid pPFL39 was digested with Nde I and Nhe I and the 3.3 kbp fragment was purified by gel electrophoresis and ligated to pND30 previously digested with Nde I and Nhe I and treated with alkaline phosphatase. The ligation mixture was used to transform electrocompetent *E. coli* DH10B cells and individual clones were checked for the desired plasmid pPFL42. Plasmid pPFL42 was identified by restriction analysis.

EXAMPLE 7

Construction of *S. erythraea* JC2/pPFL42

Plasmid pPFL42 was used to transform *S. erythraea* JC2 protoplasts. Thiostrepton resistant colonies were selected in R2T20 medium containing 10 µg/ml of thiostrepton. Several clones were tested for the presence of pPFL42 integrated into the chromosome by Southern blot hybridisation of their genomic DNA with DIG-labelled DNA containing the tyl PKS fragment encoding for the loading module. A clone with an integrated copy of pPFL42 was identified in this way,

EXAMPLE 8

Production of Polyketides Using *S. erythraea* JC2/pPFL42

A frozen suspension of strain *S. erythraea* JC2/pPFL42 was used to inoculate eryP medium containing 5 µg/ml of thiostrepton and allowed to grow for seven days at 28–30° C. After this time the broth was filtered to remove mycelia and the pH adjusted to pH=3. The broth was extracted twice with two volumes of ethyl acetate and the combined extracts were washed with an equal volume of saturated sodium chloride, dried over anhydrous sodium sulphate, and the ethyl acetate was removed under reduced pressure, to give crude product. The product was shown to have the structure shown below, and was identical, as judged by MS, GC-MS, and $^1$H NMR with an authentic sample:

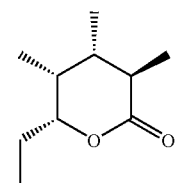

EXAMPLE 9

Construction of *S. erythraea* NRRL2338/pPFL42

Plasmid pPFL42 was used to transform *S. erythraea* NRRL2338 protoplasts. Thiostrepton resistant colonies were selected in R2T20 medium containing 10 µg/ml of thiostrepton. Several clones were tested for the presence of pPFL42 integrated into the chromosome by Southern blot hybridisation of their genomic DNA with DIG-labelled DNA containing the tyl PKS fragment encoding for the loading module. A clone with an integrated copy of pPFL42 was identified in this way.

EXAMPLE 10

Production of polyketides using *S. erythraea* NRR2338/pPFL42

A frozen suspension of strain *S. erythraea* NRRL2338/pPFL42 was used to inoculate eryP medium containing 5 µg/ml of thiostrepton and allowed to grow for seven days at 28–30° C. After this time the broth was filtered to remove mycelia and the pH adjusted to pH=9. The supernatant was then extracted three times with an equal volume of ethyl acetate and the solvent was removed by evaporation. Products were analysed by HPLC/MS and a macrolide was identified with the following structure, identical with that of authentic erythromycin A (together with other products, which were identified as the corresponding erythromycins B and D, the result of incomplete post-PKS processing):

EXAMPLE 11

Construction of Plasmid pPFL35

Plasmid pPFL35 is a pCJR24-based plasmid containing a PKS gene comprising a loading module, the first and second extension modules of DEBS and the chain terminating thioesterase. The loading module comprises the KSq domain DNA from the loading module of the oleandomycin PKS fused to the malonyl-CoA-specific AT of module 2 of the rapamycin PKS, in turn linked to the DEBS loading domain ACP. Plasmid pPFL35 was constructed via several intermediate plasmids as follows:

A 411 bp DNA segment of the eryAI gene from *S. erythraea* extending from nucleotide 1279 to nucleotide is 1690 (Donadio, S. et al., Science (1991) 2523:675–679) was amplified by PCR using the following synthetic oligonucleotide primers: 5'-TGGACCGCCGCCAATTGCCTAG-GCGGGCCGAACCCGGCT-3' (SEQ ID No. 32) and 5'-CCTGCAGGCCATCGCGACGACCGCGAC-CGGTTCGCC-3' (SEQ ID No. 33).

The DNA from a plasmid designated pKSW, derived from pT7-7 and DEBS1-TE in which new Pst I and HindIII sites had been introduced to flank the KS1 of the first extension module, was used as a template. The 441 bp PCR product was treated with T4 polynucleotide kinase and ligated to plasmid pUC18, which had been linearised by digestion with Sma I and then treated with alkaline phosphatase. The ligation mixture was used to transform electrocompetent *E. coli* DH10B cells and individual clones were checked for the desired plasmid, pPFL26. The new Mfe I/Avr II sites bordering the insert are adjacent to the Eco RI site in the polylinker of pUC18. Plasmid pPFL26 was identified by restriction pattern and sequence analysis.

An Mfe I restriction site is located 112 bp from the 5' end of the DNA encoding the propionyl-CoA:ACP transferase of the loading module of DEBS. Plasmid pKSW was digested with Mfe I and Pst I and ligated with the 411 bp insert obtained by digesting plasmid pPFL26 with Mfe I and Pst I. The ligation mixture was used to transform electrocompetent *E. coli* DH10B cells and individual clones were checked for the desired plasmid, pPFL27. Plasmid pPFL27 contains a PKS gene comprising the DEBS loading module, the first and second extension modules of DEBS and the DEBS chain terminating thioesterase. Plasmid pPFL27 was identified by its restriction pattern.

Plasmid pPFL27 was digested with Nde I and Avr II and ligated to a 4.6 kbp insert derived from digesting plasmid pMO6 (PCT/GB97/01819) with Nde I and Avr II. Plasmid pMO6 contains a PKS gene comprising the DEBS loading module, the first and second extension modules of DEBS and the DEBS chain terminating thioesterase, except that the DNA segment encoding the methylmalonate-specific AT within the first extension module has been specifically substituted by the DNA encoding the malonate-specific AT of module 2 of the rap PKS. The ligation mixture was used to transform electrocompetent *E. coli* DH10B cells and individual clones were checked for the desired plasmid, pPFL28. Plasmid pPFL28 contains a hybrid PKS gene comprising the DEBS loading module, the malonate-specific AT of module 2 of the rap PKS, the ACP of the DEBS loading module, followed by the first and second extension modules of DEBS and the DEBS chain terminating thioesterase. Plasmid pPFL28 was identified by restriction analysis.

A DNA segment encoding the KSq domain from the oleAI gene of *S. antibioticus* extending from nucleotide 1671 to nucleotide 3385 was amplified by PCR using the following synthetic oligonucleotide primers: 5'-CCA-CATATGCATGTCCCCGGCGAGGAA-3' (SEQ ID No. 34) and 5'-CCCTGTCCGGAGAAGAGGAAGGCGAGGCCG-3' (SEQ ID No. 35) and chromosomal DNA from *Streptomyces antibioticus* as a template. The PCR product was treated with T4 polynucleotide kinase and ligated to plasmid pUC18, which had been linearised by digestion with Sma I and then treated with alkaline phosphatase. The ligation mixture was used to transform electrocompetent *E. coli* DH10B cells and individual clones were checked for the desired plasmid, pPFL31. The new Nde I site bordering the insert is adjacent to the Eco RI site of the pUC18 polylinker while the new Bsp EI site borders the Hin dIII site of the linker region. Plasmid pPFL31 was identified by restriction and sequence analysis.

Plasmid pPFL31 was digested with Nde I and Avr II and the insert was ligated with plasmid pPFL28 that had been digested with Nde I and Avr II. The ligation mixture was used to transform electrocompetent *E. coli* DH10B cells and individual clones were checked for the desired plasmid, pPFL32. Plasmid pPFL32 was identified by restriction analysis.

Plasmid pPFL32 was digested with Nde I and Xba I and the insert was ligated to plasmid pCJR24, which had been digested with Nde I and Xba I and purified by gel electrophoresis. The ligation mixture was used to transform electrocompetent *E. coli* DH10B cells and individual clones were checked for the desired plasmid, pPFL35. Plasmid pPFL35 was identified by restriction analysis.

EXAMPLE 12

Construction of *S. erythraea* JC2/PPFL35

Plasmid pPFL35 was used to transform *S. erythraea* JC2 protoplasts. Thiostrepton resistant colonies were selected in R2T20 medium containing 10 µg/ml of thiostrepton. Several clones were tested for the presence of pPFL35 integrated into the chromosome by Southern blot hybridisation of their genomic DNA with DIG-labelled DNA containing the rap PKS fragment encoding for module 2 acyltransferase. A clone with an integrated copy of pPFL35 was identified in this way.

EXAMPLE 13

Production of polyketides using *S. erythraea* JC2/pPFL35

A frozen suspension of strain *S. erythraea* JC2/pPFL35 was used to inoculate eryP medium containing 5 μg/ml of thiostrepton and allowed to grow for seven days at 28–30° C. After this time the broth was filtered to remove mycelia and the pH adjusted to pH=3. The broth was extracted twice with two volumes of ethyl acetate and the combined extracts were washed with an equal volume of saturated sodium chloride, dried over anhydrous sodium sulphate, and the ethyl acetate was removed under reduced pressure, to give crude product. The product was shown to have the following structure, and was found by MS, GC-MS and $^1$H NMR to be identical to authentic material:

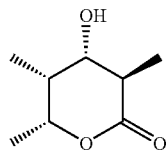

EXAMPLE 14

Construction of *S. erythraea* NRRL2338/pPFL35

Plasmid pPFL35 was used to transform *S. erythraea* NRRL2338 protoplasts. Thiostrepton resistant colonies were selected in R2T20 medium (Yamamoto et al.) containing 10 μg/ml of thiostrepton. Several clones were tested for the presence of pPFL35 integrated into the chromosome by Southern blot hybridisation of their genomic DNA with DIG-labelled DNA containing the rap PKS fragment encoding for module 2 AT. A clone with an integrated copy of pPFL35 was identified in this way.

EXAMPLE 15

Production of 13-methyl-erythromycin A and B using *Sacch. erythraea* NRRL-2338 (pPFL35)

The culture *Saccharopolyspora erythraea* NRRL2338 (pPFL35), constructed with the wild-type loading domain displaced by an oleandomycin KSQ-rapamycin AT2- D1TE DNA insert, prepared as described in Example 14, was inoculated into 30 ml Tap Water medium with 50 μg/ml thiostrepton in a 300 ml Erlenmeyer flask. After two days incubation at 29° C., this flask was used to inoculate 300 ml of ERY-P medium in a 300 ml flask. The broth was incubated at 29° C. at 200 rpm for 6 days. After this time, the whole broth was adjusted to pH 8.5 with NaOH, then extracted with an equal volume of ethyl acetate. The ethyl acetate extract was evaporated to dryness at 45° C. under a nitrogen stream using a Zymark TurboVap LV Evaporator, then reconstituted in 0.25 volumes methanol to concentrate the extract 4-fold. The structure of the products were confirmed by LC/MS, Method A. A peak was observed with a retention time of 4.0 min and with an m/z value of 720 (M+H)$^+$, required for 13-methyl-erythromycin A ($C_{36}H_{65}NO_{13}$). A second peak was observed with a retention time of 6.4 min and with m/z value of 704 (M+H)$^+$, required for 13-methyl-erythromycin B ($C_{36}H_{65}NO_{12}$).

EXAMPLE 16

Construction of Recombinant Vector pPFL44

Plasmid pPFL44 is a pCJR24- based plasmid containing the gene encoding a hybrid polyketide synthase that contains the spiramycin PKS loading module, the erythromycin extension modules 1 and 2 and the chain-terminating thioesterase. Plasmid pPFL44 was constructed as follows:

The following synthetic oligonucleotides: 5'-CCATAT-GTCTGGAGAACTCGCGATTTCCCGCAGT-3' (SEQ ID No. 36) and 5'-GGCTAGCGGGTCGTCGTCGTCCCG-GCTG-3' (SEQ ID No. 37) were used to amplify the DNA encoding the spiramycin producing loading module using chromosomal DNA from the spiramycin producer *S. ambofaciens* prepared according to the method described by Hopwood et al. (1985). The PCR product of 3.3 kbp was purified by gel electrophoresis, treated with T4 polynucleotide kinase and ligated to plasmid pUC18, which had been linearised by digestion with Sma I and then treated with alkaline phosphatase. The ligation mixture was used to transform electrocompetent *E. coli* DH10B cells and individual clones were checked for the desired plasmid pPFL41. Plasmid pPFL41 was identified by restriction patten and sequence analysis.

Plasmid pPFL41 was digested with Nde I and Nhe I and the 3.3 kbp fragment was purified by gel electrophoresis and ligated to pND30 (a plasmid derived from plasmid pCJR24 having as insert the ave PKS loading module and extension modules 1 and 2 or DEBS and the DEBS thioesterase) (PCTGB97/01810) previously digested with Nde I and Nhe I and treated with alkaline phosphatase. The ligation mixture was used to transform electrocompetent *E. coli* DH10B cells and individual clones checked for the desired plasmid pPFL44. Plasmid pPFL44 was identified by restriction analysis.

EXAMPLE 17

Construction of *S. erythraea* JC2/pPFL44

Plasmid pPFL44 was used to transform *S. erythraea* JC2 protoplasts. Thiostrepton resistant colonies were selected in R2T20 medium containing 10 μg/ml of thiostrepton. Several clones were tested for the presence of pPFL44 integrated into the chromosome by Southern blot hybridisation of their genomic DNA with DIG-labelled DNA containing the srm PKS fragment encoding for the loading module. A clone with an integrated copy of pPFL44 was identified in this way.

EXAMPLE 18

Production of polyketides using *S. erythraea* JC2/pPFL44

A frozen suspension of strain *S. erythraea* JC2/pPFL44 was used to inoculate eryP medium containing 5 μg/ml of thiostrepton and allowed to grow for seven days at 28–30° C. After this time the broth was filtered to remove mycelia and the pH adjusted to pH=3. The broth was extracted twice with two volumes of ethyl acetate and the combined extracts were washed with an equal volume of saturated sodium chloride, dried over anhydrous sodium sulphate, and the ethyl acetate was removed under reduced pressure, to give crude product. The product was shown to have the structure shown below and by GC-MS and $^1$H NMR analysis was identical to authentic material:

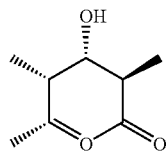

EXAMPLE 19

Construction of *S. erythraea* NRRL2338/pPFL44

Plasmid pPFL44 was used to transform *S. erythraea* NRRL2338 protoplasts. Thiostrepton resistant colonies were selected in R2T20 medium containing 10 μg/ml of thiostrepton. Several clones were tested for the presence of pPFL44 integrated into the chromosome by Southern blot hybridisation of their genomic DNA with DIG-labelled DNA containing the spiramycin PKS fragment encoding for the loading module. A clone with an integrated copy of pPFL44 was identified in this way.

EXAMPLE 20

Production of 13 methyl-erythromycin A and B using *Sacch. erythraea* NRRL-2338 (pPFL44)

The culture *Saccharopolyspora etythraea* NRRL2338 (pPFL44), constructed with the wild-type loading domain displaced by spiramycin loader-D1TE DNA insert, was inoculated into 30 ml Tap Water medium with 50 μg/ml thiostrepton in a 300 ml Erlenmeyer flask. After three days incubation at 29° C., this flask was used to inoculate 300 ml of ERY-P medium in a 300 ml flask. The broth was incubated at 29° C. at 200 rpm for 6 days. After this time, the whole broth was adjusted to pH 8.5 with NaOH, then extracted with equal volume of ethyl acetate. The ethyl acetate extract was evaporated to dryness at 45° C. under a nitrogen stream using Zymark TurboVap LV Evaporator, then reconstituted in 0.0625 volumes methanol to concentrate the extract 16-fold. The structures of the products were confirmed by LC/MS, Method A. A 4.0 min retention time peak was observed as the major component, with m/z value of 720 (M+H)$^+$, required for 13-methyl-erythromycin A ($C_3H_{65}NO_{13}$). A second peak was observed with a retention time of 6.4 min and with m/z value of 704 (M+H)$^+$, required for 13-methyl-erythromycin B ($C_{36}H_{65}NO_{12}$).

EXAMPLE 21

Construction of Plasmid pJLK114

Figure 6:
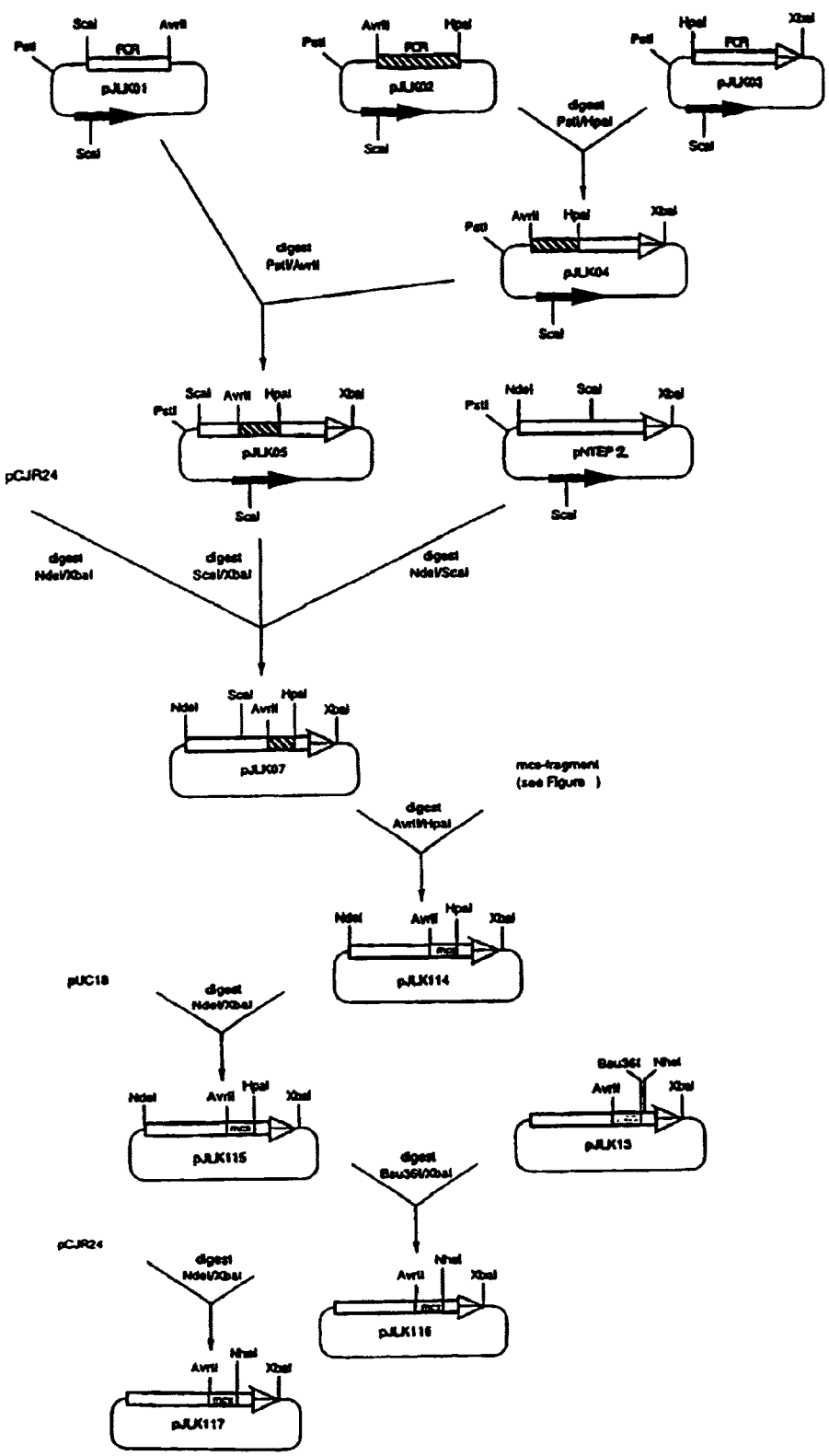
FIG. 6 is a diagram showing the construction of plasmid pJLK117.

Plasmid pJLK114 is a pCJR24 based plasmid containing a PKS gene comprising the ery loading module, the first and the second extension modules of the ery PKS and the ery chain-terminating thioesterase except that the DNA segment between the end of the acyltransferase and the beginning of the ACP of the second ery extension module has been substituted by a synthetic oligonucleotide linker containing the recognition sites of the following restriction enzymes: AvrII, BglII, SnaBI, PstI, SpeI, NsiI, Bsu36I and HpaI. It was constructed via several intermediate plasmids as follows (FIG. 6).

Construction of Plasmid pJLK02

The approximately 1.47 kbp DNA fragment of the eryAI gene of *S. erythraea* was amplified by PCR using as primers the synthetic oligonucleotides: 5'-TACCTAGGCCGGGC-CGGACTGGTCGACCTGCCGGGTT-3' (SEQ ID No. 38) and 5'-ATGTTAACCGGTCGCGCAGGCTCTCCGTCT-3' (SEQ ID No. 39) and plasmid pNTEP2 (Oliynyk, M. et al., *Chemistry and Biology* (1996) 3:833–839; WO98/01546) as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK02 was identified by its restriction pattern and DNA sequencing.

Construction of Plasmid pJLK03

The approximately 1.12 kbp DNA fragment of the eryAI gene of *S. erythraea* was amplified by PCR using as primers the synthetic oligonucleotides: 5'-ATGTTAACGGGTCT-GCCGCGTGCCGAGCGGAC-3' (SEQ ID No. 40) and 5'-CTTCTAGACTATGAATTCCCTCCGCCCAGC-3' (SEQ ID No. 41) and plasmid pNTEPH as template. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid, pJLK03 was identified by its restriction pattern and DNA sequencing.

Construction of Plasmid pJLK04

Plasmid pJLK02 was digested with PstI and HpaI and the 1.47 kbp insert was ligated with plasmid pJLK03 which had been digested with PstI and HpaI. The ligation mixture was used to transform electrocompetent *E. coli* DH10B cells and individual colonies were checked for their plasmid content. The desired plasmid pJLK04 was identified by its restriction pattern.

Construction of Plasmid pJLK05

Plasmid pJLK01 (PCT/GB97/01819) was digested with PstI and AvrII and the 460 bp insert was ligated with plasmid pJLK04 which had been digested with PstI and AvrII. The ligation mixture was used to transform electrocompetent *E. coli* DH10B cells and individual colonies were checked for their plasmid content. The desired plasmid pJLKOS was identified by its restriction pattern.

Construction of Plasmid PJLK07

Plasmid pJLKOS was digested with ScaI and XbaI and plasmid pNTEPH was digested with NdeI and ScaI and these two fragments were ligated with plasmid pCJR24 which had been digested with NdeI and XbaI. The ligation mixture was used to transform electrocompetent *E. coli* DH10B cells and individual colonies were checked for their plasmid content. The desired plasmid pJLK07 was identified by its restriction pattern.

Construction of Plasmid pJLK114

The two synthetic oligonucleotides Plf and Plb (FIG. 7) were each dissolved in TE-buffer. 10 μl of each solution (0.5 nmol/μl) were mixed and heated for 2 minutes to 65C and then slowly cooled down to room temperature. Plasmid pJLK07 was digested with AvrII and HpaI and ligated with the annealed oligonucleotides. The ligation mixture was used to transform electrocompetent *E. coli* DH10B cells and individual colonies were checked for their plasmid content. The desired plasmid pJLK114 was identified by its restriction pattern.

Plasmid pJLK117 is a pCJR24 based plasmid containing a PKS gene comprising the ery loading module, the first and the second extension modules of the ery PKS and the ery chain-terminating thioesterase except that the DNA segment between the end of the acyltransferase and the beginning of the ACP of the second ery extension module has been substituted by a synthetic oligonucleotide linker containing the recognition sites of the following restriction enzymes. AvrII, BglII, SnaBI, PstI, SpeI, NsiI, Bsu36I and NheI.

It was constructed via several intermediate plasmids as follows (FIG. 6).

Construction of Plasmid pJLK115

Plasmid pJLK114 was digested with NdeI and XbaI and the approximately 9.9 kbp insert was ligated with plasmid pUC18 which had been digested with NdeI and XbaI. The ligation mixture was used to transform electrocompetent *E. coli* DH10B cells and individual colonies were checked for their plasmid content. The desired plasmid pJLK115 was identified by its restriction pattern.

Construction of Plasmid pJLK116

Plasmid pJLK13 (PCT/GB97/01819) was digested with Bsu36I and XbaI and the 1.1 kbp fragment was ligated with plasmid pJLK115 which had been digested with Bsu36I and XbaI. The ligation mixture was used to transform electrocompetent *E. coli* DH10B cells and individual colonies were checked for their plasmid content. The desired plasmid pJLK116 was identified by its restriction pattern.

Construction of Plasmid pJLK117

Plasmid pJLK116 was digested with NdeI and XbaI and the 9.9 kbp fragment was ligated with plasmid pCJR24 which had been digested with NdeI and XbaI. The ligation mixture was used to transform electrocompetent *E. coli* DH10B cells and individual colonies were checked for their plasmid content. The desired plasmid pJLK117 was identified by its restriction pattern.

EXAMPLE 11

Construction of Plasmid pJLK29

Figure 5:
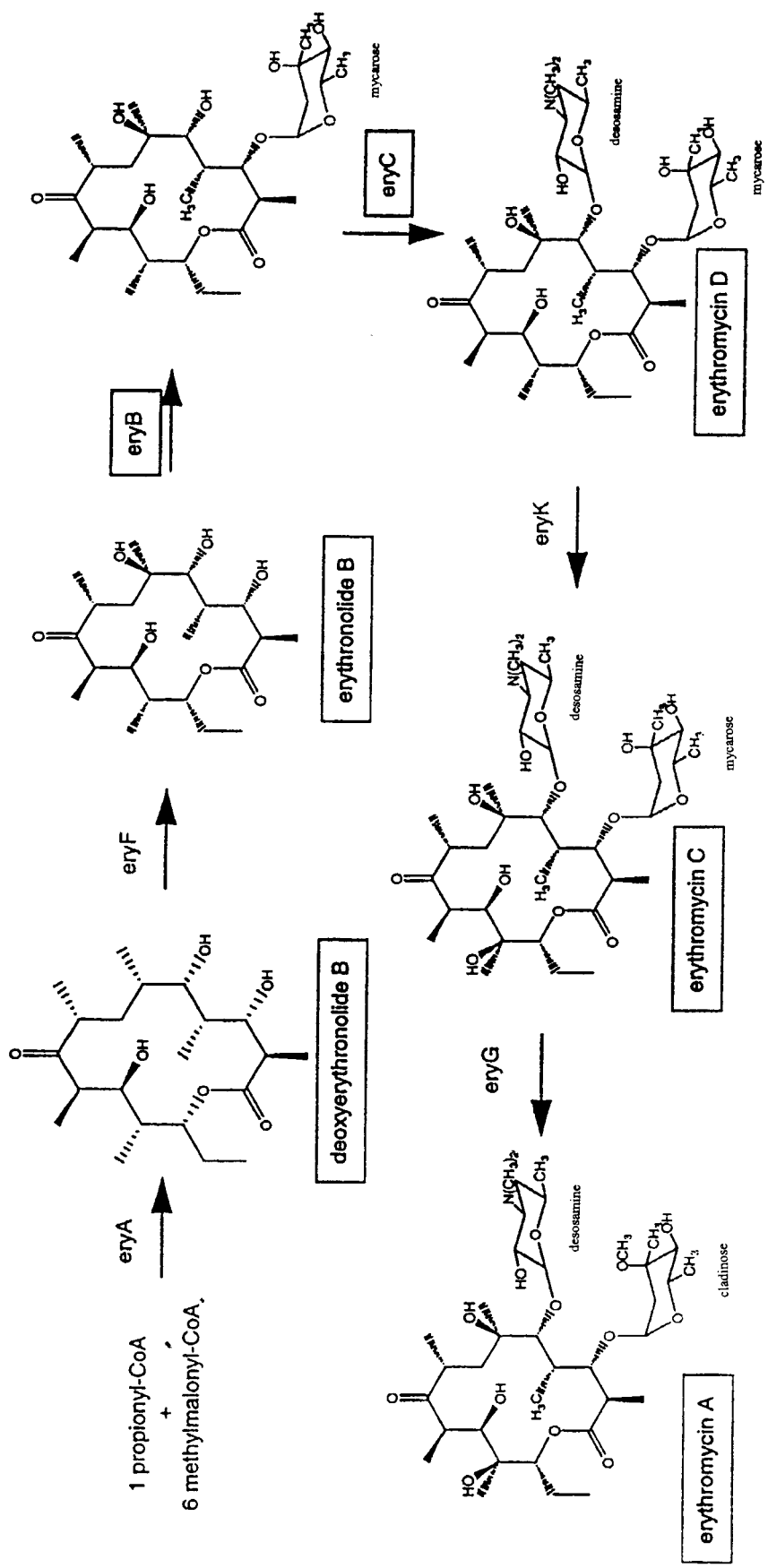
FIG. 5 The enzymatic steps that convert 6-deoxyerythronolide B into erythromycin A in *Saccharopolyspora erythraea*.

Plasmid pJLK29 is a pJLK117 based plasmid except that the DNA fragment encoding the reductive loop of module 10 of the rap PKS has been inserted into the mcs. It was constructed via several intermediate plasmids as follows. (FIG. 5)

Construction of Plasmid pJLK121.1

The approximately 2.2 kbp DNA segment of the rapB gene of *S. hygroscopicus* encoding the reductive loop of module 10 was amplified by PCR using as primers the synthetic oligonucleotides: 5'-TAAGATCTTCCGACG-TACGCGTTCCAGC-3' (SEQ ID No. 42) and 5'-AT-GCTAGCCACTGCGCCGACGAATCACCGGTGG-3' (SEQ ID No. 43) and as template an approximately 7 kbp fragment, which has been obtained by digestion of cosmid cos 26 (Schwecke, T. et al. (1995) Proc. Natl. Acad. Sci. USA 92:7839–7843) with ScaI and SphI. The PCR product was treated with T4 polynucleotide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK121.1 was identified by its restriction pattern and DNA sequencing.

Construction of Plasmid pJLK29

Plasmid pJLK121.1 was digested with BglII and NheI and the 2.2 kbp fragment was ligated with plasmid pJLK117 which had been digested with BglII and NheI. The ligation mixture was used to transform electrocompetent *E. coli* DH10B cells and individual colonies were checked for their plasmid content. The desired plasmid pJLK29 was identified by its restriction pattern.

EXAMPLE 24

Construction of Plasmid pJLK50

The approximately 6.1 kbp DNA segment of the erythromycin PKS gene cluster of *S. erythraea* encoding the DNA fragment from the beginning of the ACP of module 2 to the beginning of the ACP of module 3 was amplified by PCR using as primers the synthetic oligonucleotides: 5'-TACCT-GAGGGACCGGCTAGCGGGTCTGCCGCGTG-3' (SEQ ID No. 44) and 5'-ATGCTAGCCGTTGTGCCGGCTCGC-CGGTCGGTCC-3' (SEQ ID No. 45) and plasmid pBAM25 (published pBK25 by Best, D J et al. Eur J Biochem (1992) 204: 39–49) as template. The PCR product was treated with T4 polynuclectide kinase and then ligated with plasmid pUC18, which had been linearised by digestion with SmaI and then treated with alkaline phosphatase. The ligation mixture was used to transform electrocompetent *E. coli* DH10B cells and individual colonies were checked for their plasmid content. The desired plasmid pJLK50 was identified by its restriction pattern and DNA sequencing.

EXAMPLE 25

Construction of *S. erythraea* Strain JLK10

Strain JLK10 is a variant of strain NRRL2338 in which the reductive loop of ery module 2 (i.e. the KR domain) is replaced by the reductive loop of the rapamycin module 10. It was constructed using plasmid pJLK54 which was constructed as follows.

Construction of Plasmid pJLK54

Plasmid pJLK54 is a pJLK29 based plasmid containing a PKS gene comprising the ery loading module, the first, the second and the third extension modules of the ery cluster and the ery chain-terminating thioesterase except that the DNA segment between the end of the acyltransferase and the beginning of the ACP of the second ery extension module has been substituted by the equivalent segment of module 10 of the rapamycin PKS.

It was constructed as follows.

Plasmid pJLK50 was digested with NheI and the 6.1 kbp insert was ligated with plasmid pJLK29 which had been digested with NheI. The ligation mixture was used to transform electrocompetent *E. coli* DH10B cells and individual colonies were checked for their plasmid content. The desired plasmid pJLK54 was identified by its restriction pattern.

Use of plasmid pJLK54 for construction of *S. erythraea* NRRL2338/pJLK54 and the production of TKL derivatives Approximately 5 µg plasmid pJLK54 were used to transform protoplasts of *S. erythraea* NRRL2338 and stable thiostrepton resistant colonies were isolated. From several colonies total DNA is obtained and analysed by Southern blot hybridisation, to confirm that the plasmid has integrated into the TE.

Construction of S. erythraea Strain JLK10 and its use in Production of 13-methyl-10,11-dehydro-erythromycin A S. erythraea strain JLK10 is a mutant of S. erythraea NRRL2338 in which the 'reductive loop' of ery module 2 i.e. the ketoreductase domain is substituted by the 'reductive loop' of rapamycin module 10. It was constructed starting from S. erythraea NRRL2338 into which plasmid pJLK54 had been integrated. S. erythraea NRRL2338/pJLK54 was subjected to several rounds of non-selective growth which resulted in second crossover concomitant with the loss of the integrated plasmid. Clones in which replacement of the erythromycin gene coding for DEBS1 with the mutant version had occurred, were identified by Southern blot hybridisation. One of these was named S. erythraea strain JLK10 and was used to inoculate SM3 medium (eryP medium gave similar results), and allowed to grow for seven to ten days at 28–30° C. After this time the broth was centrifuged and the pH of the supernatant adjusted to pH 9. The supernatant was then extracted three times with an equal volume of ethyl acetate and the solvent was removed by evaporation. Products were analysed by HPLC/MS, MS/MS and $^1$H-NMR. The following macrolide C-13 methyl erythromycin A was identified (accompanied by products of incomplete processing by post-PKS enzymes).

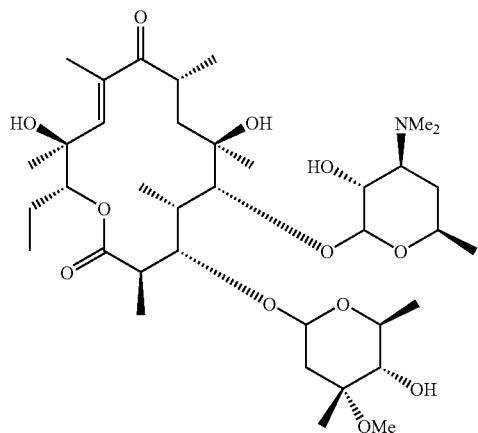

EXAMPLE 26

Construction of Plasmid pPFL50

Plasmid pPFL50 is a pPFL43-based plasmid from which a DNA fragment encoding KR1 (in part), ACP1 and module 2 of the erythromycin PKS and the erythromycin TE, has been removed. It was constructed as follows. Plasmid pPFL43 was digested with SfuI and XbaI to remove a 6.5 kb fragment. The 5' overhangs were filled in with Klenow fragment DNA Polymerase I and the plasmid was recircularised. The ligation mixture was used to transform electrocompetent E. coli DH10B cells and individual colonies were checked for their plasmid content. The desired plasmid pPFL50 was identified by its restriction pattern.

Construction of S. erythraea JLK10/pPFL50

Approximately 5 μg plasmid pPFL50 were used to transform protoplasts of S. erythraea strain JLK10 and stable thiostrepton resistant colonies were isolated. From several colonies total DNA was obtained and analysed by Southern blot hybridisation, to confirm that the plasmid had integrated into the homologous chromosomal DNA region. S. erythraea strain JLK10/pPFL50 was used to inoculate SM3 medium containing 5 μg/ml thiostrepton (eryP medium containing 5 μg/ml thiostrepton gave similar results) and allowed to grow for seven to ten days at 28–30° C. After this time the broth was centrifuged and the pH of the supernatant adjusted to pH 9. The supernatant was then extracted three times with an equal volume of ethyl acetate and the solvent was removed by evaporation. Products were analysed by HPLC/MS, MS/MS and 1H-NMR. The macrolide C-13 methyl 10,11-dehydro-erythromycin A was identified (accompanied by products of incomplete processing by post-PKS enzymes)

Construction of S. erythraea NRRL2338/pPFL50

Approximately 5 μg plasmid pPFL50 were used to transform protoplasts of S. erythraea NRRL2338 and stable thiostrepton resistant colonies were isolated. From several colonies total DNA was obtained and analysed by Southern blot hybridisation, to confirm that the plasmid had integrated into the homologous region of the chromosomal DNA. S. erythraea NRRL2338/pPFL50 was used to inoculate SM3 medium containing 5 μg/ml thiostrepton (eryP medium containing 5 μg/ml thiostrepton gives similar results) and allowed to grow for seven to ten days at 28–30° C. After this time the broth was centrifuged and the pH of the supernatant adjusted to pH 9.5. The supernatant was then extracted three times with an equal volume of ethyl acetate and the solvent was removed by evaporation. Products were analysed by HPLC/MS, MS/MS and 1H-NMR. The macrolide C-13 methyl erythromycin A was identified (accompanied by products of incomplete processing by post-PKS enzymes).

Construction of Plasmid pCB121

Plasmid pCB121 is a plasmid containing the monensin loading module and KS of monensin module 1 followed by the erythromycin module 1 AT and part of the erythromycin module1 KR. It was constructed via several intermediate plasmids as follows.

Construction of Plasmid pPFL45

The approximately 1.8 kbp DNA segment of the monensin PKS gene cluster of Streptomyces cinnamonensis encoding part of the ACP of the loading module 1 and KS of module 1 was amplified by PCR using as primers the synthetic oligonucleotides: 5'-CGTTCCTGAGGTCGCTG-GCCCAGGCGTA-3' (SEQ ID No. 46) and 5'-CGAAGCT-TGACACCGCGGCGCGGCGCGG-5' (SEQ ID No. 47) and a cosmid containing the 5' end of the monensin PKS genes from S. cinnamonensis or alternatively chromosomal DNA of S. cinnamonensis as template. The PCR product was treated with T4 polynucleotide kinase and then ligated with plasmid pUC18, which had been linearised by digestion with SmaI and then treated with alkaline phosphatase. The ligation mixture was used to transform electrocompetent E. coli DH10B cells and individual colonies were checked for their plasmid content. The desired plasmid pPFL45 was identified by its restriction pattern.

Construction of Plasmid pPFL47

Plasmid pPFL45 was digested with NdeI and Bsu36I and the approximately 2.6 kbp fragment was ligated into plasmid pPFL43 which had been digested with NdeI and Bsu36I. The ligation mixture was used to transform electrcompetent E. coli DH10B cells and individual colonies were checked for their plasmid content. The desired plasmid pPFL47 was identified by its restriction pattern.

Construction of Plasmid pCB135

Plasmid pCJR24 was digested with HindIII, the 5' overhang was filled in with Klenow fragment DNA Polymerase I and religated. The ligation mixture was used to transform electrocompetent E. coli DH10B cells and individual colonies were checked for their plasmid content. The desired plasmid pCB135 was identified by its restriction pattern, lacking the recognition site for HindIII.

Construction of Plasmid pKSW1

Plasmid pKS1W is a pNTEP2 (GB97/01810)-derived vector containing a DEBS1TE-derived triketide synthase with the unique restriction sites introduced at the limits of KS1. Plasmid pKS1W is obtained via several intermediate plasmids as follows.

Construction of Plasmids pMO09, pMO10 and pMO13

For the PCR amplification for plasmid pMO09, the following synthetic oligonucleotides were used as mutagenic primers, one containing a MunI site and the other a PstI site: 5'-GCGCGCCAATTGCGTGCACATCTCGAT-3' (SEQ ID No. 48) and 5'-CCTGCAGGCCATCGCGACGACCGC-GACCGGTTCGCCG-3' (SEQ ID No. 49).

For the PCR amplification for plasmid pMO010, the following synthetic oligonucleotides were used as mutagenic primers, one containing a HindIII site and the other an EcoRV site: 5'-GTCTCAAGCTTCGGCAT-CAGCGGCACCAA-3' (SEQ ID No. 50) and 5'-CGTGC-GATATCCCTGCTCGGCGAGCGCA-3' (SEQ ID No. 51).

For the PCR amplification for plasmid pMO13, the following synthetic oligonucleotides were used as mutagenic primers, one containing a PstI site and the other a HindIII site: 5'-GATGGCCTGCAGGCTGCCCGGCGGTGT-GAGCA-3' (SEQ ID No. 52) and 5'-GCCGAAGCT-TGAGACCCCCGCCCGGCGCGGTCGC-3' (SEQ ID No. 53) PCR was carried out on pNTEP2 (GB97/01810) as template using Pwo DNA polymerase and one cycle of: 96° C. (1 min); annealing at 50° C. (3 min); and extension at 72° C. (1 min), and 25 cycles of: 96° C. (1 min); annealing at 50° C. (1 min); and extension at 72° C. (1 min) in the presence of 10% (vol/vol) dimethylsulphoxide. The products were end-repaired and cloned into pUC18 digested with SmaI and the ligation mixture was transformed into E. coli DH 10B. Plasmid DNA was prepared from individual colonies. The desired plasmids for pMO09 (3.8 kbp), pMO10 (3.9 kbp) and pMO13 (4.3 kpb) were identified by their restriction pattern and DNA sequencing.

Construction of Plasmid pMO11

Plasmid pMO13 was digested with HindIII, and the 1.2 kbp insert was cloned into pMO10 which had been digested with HindIII. The ligation mixture was transformed into E. coli DH 10B. The desired plasmid (5.0 kbp) was identified by its restriction pattern and designated pMO11.

Construction of Plasmid pMO12

Plasmid pMO09 was digested with PstI, and the 1.6 kbp insert was cloned into pMO11 which had been digested with PstI. The ligation mixture was transformed into E. coli DH 10B. The desired plasmid (6.6 kbp) was identified by its restriction pattern and designated pMO12.

Construction of pKS1W

Plasmid pMO12 was digested with MunI and EcoRV, and the 3.9 kbp fragment was cloned into pNTEPH (see below) which had been digested with MunI and EcoRV. The ligation mixture was transformed into E. coli DH 10B. The desired plasmid (13. kbp) was identified by its restriction pattern and designated pKS1W.

Construction of pNTEPH

Plasmid pNTEPH was obtained from pNTEP2 by removing the HindIII site. pNTEP2 was digested with HindIII, the 5' overhang was filled in with Klenow Fragment DNA Polymerase I and religated. The desired plasmid (13.6 kbp) was identified by its restriction pattern.

Construction of Plasmid pCB136

Plasmid pKSW1 was digested with NdeI and XbaI and the approximately 11.2 kbp fragment was ligated with plasmid pCB135 which had been digested with NdeI and XbaI. The ligation mixture was used to transform electrocompetent E. coli DH10B cells and individual colonies were checked for their plasmid content. The desired plasmid pCB136 was identified by its restriction pattern.

Construction of Plasmid pCB137

Plasmid pCB136 was digested with SfuI and XbaI to remove a 6.5 kb fragment, the 5' overhangs were filled in with Klenow Fragment DNA Polymerase I and religated. The ligation mixture was used to transform electrocompetent E. coli DH10B cells and individual colonies were checked for their plasmid content. The desired plasmid pCB137 was identified by its restriction pattern.

Construction of Plasmid pCB121

Plasmid pPFL47 was digested with NdeI and HindIII and the approximately 4.4 kbp insert was ligated with plasmid pCB137 which had been digested with NdeI and HindIII. The ligation mixture was used to transform electrocompetent E. coli DH10B cells and individual colonies were checked for their plasmid content. The desired plasmid pCB121 was identified by its restriction pattern.

EXAMPLE

Construction of S. erythraea JLK10/pCB121

Approximately 5 µg plasmid pCB121 were used to transform protoplasts of S. erythraea JLK10 and stable thiostrepton resistant colonies were isolated. From several colonies total DNA was obtained and analysed by Southern blot hybridisation, to confirm that the plasmid had integrated into the homologous chromosomal DNA region. S. erythraea strain JLK10/pCB121 was used to inoculate SM3 medium containing 5 µg/ml thiostrepton (eryP medium containing 5 µg/ml thiostrepton gave similar results) and allowed to grow for seven to ten days at 28–30° C. After this time the broth was centrifuged and the pH of the supernatant adjusted to pH 9. The supernatant was then extracted three times with an equal volume of ethyl acetate and the solvent was removed by evaporation. Products were analysed by HPLC/MS, MS/MS and 1H-NMR. The macrolide C13-methyl-10,11-dehydro-erythromycin A was identified (accompanied by products of incomplete processing by post-PKS enzymes):

EXAMPLE

Construction of S. erythraea NRRL2338/pCB121

Approximately 5 µg plasmid pCB121 were used to transform protoplasts of S. erythraea NRRL2338 and stable thiostrepton resistant colonies were isolated. From several colonies total DNA was obtained and analysed by Southern blot hybridisation, to confirm that the plasmid had integrated into the homologous chromosomal DNA region. S. erythraea NRRL2338/pPFL50 was used to inoculate SM3 medium containing 5 µg/ml thiostrepton (eryP medium containing 5 μg/ml thiostrepton gave similar results) and allowed to grow for seven to ten days at 28–30° C. After this time the broth was centrifuged and the pH of the supernatant adjusted to pH=9. The supernatant was then extracted three times with an equal volume of ethyl acetate and the solvent was removed by evaporation. Products were analysed by HPLC/MS, MS/MS and 1H-NMR. The macrolide C13-erythromycin A was identified (accompanied by products of incomplete processing by post-PKS enzymes):

Although the present invention is illustrated by the examples listed above, they should not be regarded as limiting the scope of the invention. The above descriptions illustrate for the first time the construction of a Type I PKS gene assembly containing a wholly or partly heterologous Ksq-containing loading module and its use to obtain polyketide products of utility as synthetic intermediates or as bioactive materials such as antibiotics. It will readily occur to the person skilled in the art that a wholly or partly heterologous Ksq-containing loading module from other PKS gene sets could be used to replace the loading module of DEBS, or indeed into a quite different PKS gene assembly. It will also readily occur to the person skilled in the art that that the additional specificity provided by the more efficient discrimination made between methylmalonyl-CoA and malonyl-CoA by an Atq, followed by specific decarboxylation by a Ksq, is preferable to the imperfect discrimination between propionyl-CoA and acetyl-CoA that is a feature of the DEBS loading module and of many other PKS loading modules, in that it maximises the production of a single product rather than a mixture differing from each other in the nature of the starter unit. The avoidance of such mixtures increases yields and avoids the need for tedious and difficult separation procedures.

Although the present invention is illustrated by the examples listed above, they should not be regarded as limiting the scope of the invention. The above descriptions illustrate for the first time the construction of a Type I PKS gene assembly containing a wholly or partly heterologous KSq-containing loading module and its use to obtain polyketide products of utility as synthetic intermediates or as bioactive materials such as antibiotics. It will readily occur to the person skilled in the art that a wholly or partly heterologous KSq-containing loading module from other PKS gene sets could be used to replace the loading module of DEBS, or indeed into a quite different PKS gene assembly. It will also readily occur to the person skilled in the art that that the additional specificity provided by the more efficient discrimination made between methylmalonyl-CoA and malonyl-CoA by an ATq, followed by specific decarboxylation by a KSq, is preferable to the imperfect discrimination between propionyl-CoA and acetyl-CoA that is a feature of the DEBS loading module and of many other PKS loading modules, in that it maximises the production of a single product rather than a mixture differing from each other in the nature of the starter unit. The avoidance of such mixtures increases yields and avoids the need for tedious and difficult separation procedures.

What is claimed is:

1. A type I polyketide synthase which produces a polyketide and which comprises a loading module and a plurality of extension modules, wherein:
   a) said loading module loads an optionally substituted malonyl and then effects decarboxylation of the loaded moiety to provide a corresponding optionally substituted acetyl moiety for transfer to the first of said extension modules; and
   b) said loading module is of the form:
      (engineered-KSq)-(AT)-(ACP), wherein:
      i) ACP is an acyl carrier protein domain;
      ii) AT is an acyltransferase domain which loads an optionally substituted malonyl; and
      iii) engineered-KSq is a ketosynthase (KS) domain which effects decarboxylation of a loaded optionally substituted malonyl, wherein said engineered-KSq domain is obtained by replacing the active site cysteine of a KS domain of an extension module with a glutamine;
   wherein the polyketide produced by the polyketide synthase is other than a 14-membered macrolide having a 13-methyl group due to incorporation of an unsubstituted acetate starter.

2. A type I polyketide synthase according to claim 1, wherein said acyltransferase domain has an arginine residue in the active site.

3. A type I polyketide synthase according to claim 2, wherein said acyltransferase domain is an extension module acyltransferase domain.

4. A type I polyketide synthase according to claim 1, wherein said ketosynthase domain which is the source of said engineered-KSq and said acyltransferase domain occur together in an extension module.

5. A type I polyketide synthase according to claim 2, wherein said acyltransferase domain is specific for loading with malonyl.

6. A type I polyketide synthase according to claim 2, wherein said acyltransferase domain is specific for loading with methylmalonyl.

7. A type I polyketide synthase according to claim 2, wherein said acyltransferase domain is the acyltransferase domain of extension module 5 of the spiramycin polyketide synthase.

8. A type I polyketide synthase according to claim 3, wherein said acyltransferase domain is the acyltransferase of module 6 of the niddamycin polyketide synthase.

9. A type I polyketide synthase according to claim 3, wherein said acyltransferase domain is the acyltransferase of module 4 of the FK506 polyketide synthase.

10. A type I polyketide synthase according to claim 1, wherein said polyketide synthase is effective to synthesize a polyketide selected from
    (a) 12- and 16-membered macrolides with acetate starter units;
    (b) 12, 14, and 16-membered macrolides with propionate starter units;
    (c) variants of rifamycin, avermectin, rapamycin, immunomycin and FK506 which differ from the natural compound in the incorporation of acetate starter units or propionate starter units;
    (d) a polyketide wherein the starter unit is derived by the action of said engineered-KSq domain on the enzyme-bound product of said AT domain, wherein said AT domain is from extension module 4 of the FK506 polyketide synthase; or
    (e) a polyketide wherein the starter unit is derived by the action of said engineered-KSq domain on the enzyme-bound product of said AT domain, wherein said AT domain is from extension module 6 of the niddamycin polyketide synthase.

11. A type I polyketide synthase which produces a polyketide and which comprises a loading module and a plurality of extension modules, wherein:
    a) said loading module loads an optionally substituted malonyl and then effects decarboxylation of the loaded moiety to provide a corresponding optionally substituted acetyl moiety for transfer to the first of said extension modules; and
    b) said loading module is of the form:
       (KSq)-(AT)-(ACP), wherein:
       i) ACP is an acyl carrier protein domain;
       ii) AT is an acyltransferase domain which loads an optionally substituted malonyl and is selected from the group consisting of the acyltransferase domain of module 6 of the niddamycin polyketide synthase, the acyltransferase domain of module 4 of the FK506 polyketide synthase, and the acyltransferase domain of module 5 of the spiramycin polyketide synthase; and
       iii) KSq is a domain which effects decarboxylation of a loaded optionally substituted malonyl and which differs from a ketosynthase domain of an extension module by having a glutamine residue in place of the cysteine residue in the active site;
    wherein the polyketide produced by the polyketide synthase is other than a 14-membered macrolide having a 13-methyl group due to incorporation of an unsubstituted acetate starter.

12. The type I polyketide synthase according to claim 11, wherein said AT is the acyltransferase domain of module 6 of the niddamycin polyketide synthase.

13. The type I polyketide synthase according to claim 11, wherein said AT is the acyltransferase domain of module 4 of the FK506 polyketide synthase.

14. The type I polyketide synthase according to claim 11, wherein said AT is the acyltransferase domain of module 5 of the spiramycin polyketide synthase.

* * * * *

SEQUENCE LISTING

<160> NUMBER OF SEQ ID NOS: 55

<210> SEQ ID NO 1
<211> LENGTH: 398
<212> TYPE: PRT
<213> ORGANISM: Streptomyces sp. C5

<400> SEQUENCE: 1

```
Met Val Thr Gly Leu Gly Ile Val Ala Pro Asn Gly Leu Gly Val Gly
 1               5                  10                  15

Ala Ile Trp Asp Ala Val Leu Asn Gly Arg Asn Gly Ile Gly Pro Leu
            20                  25                  30

Arg Arg Phe Ala Asp Asp Gly Arg Leu Gly Arg Leu Ala Gly Glu Val
        35                  40                  45

Ser Asp Phe Val Pro Glu Asp His Leu Pro Lys Arg Leu Leu Val Gln
    50                  55                  60

Thr Asp Pro Met Thr Gln Met Thr Ala Leu Ala Ala Glu Trp Ala
65                  70                  75                  80

Leu Arg Glu Ala Gly Cys Ala Pro Ser Ser Pro Leu Glu Ala Gly Val
                85                  90                  95

Ile Thr Ala Ser Ala Ser Gly Gly Phe Ala Ser Gly Gln Arg Glu Leu
            100                 105                 110

Gln Asn Leu Trp Ser Lys Gly Pro Ala His Val Ser Ala Tyr Met Ser
        115                 120                 125

Phe Ala Trp Phe Tyr Ala Val Asn Thr Gly Gln Ile Ala Ile Arg His
    130                 135                 140

Asp Leu Arg Gly Pro Val Gly Val Val Val Ala Glu Gln Ala Gly Gly
145                 150                 155                 160

Leu Asp Ala Leu Ala His Ala Arg Arg Lys Val Arg Gly Gly Ala Glu
```

```
                    165                 170                 175
Leu Ile Val Ser Gly Ala Met Asp Ser Ser Leu Cys Pro Tyr Gly Met
                180                 185                 190

Ala Ala Gln Val Arg Ser Gly Arg Leu Ser Gly Ser Asp Asp Pro Thr
            195                 200                 205

Ala Gly Tyr Leu Pro Phe Asp Arg Arg Ala Ala Gly His Val Pro Gly
        210                 215                 220

Glu Gly Gly Ala Ile Leu Ala Val Glu Asp Ala Glu Arg Val Ala Glu
225                 230                 235                 240

Arg Gly Gly Lys Val Tyr Gly Ser Ile Ala Gly Thr Ala Ser Phe Asp
                245                 250                 255

Pro Pro Pro Gly Ser Gly Arg Pro Ser Ala Leu Ala Arg Ala Val Glu
            260                 265                 270

Thr Ala Leu Ala Asp Ala Gly Leu Asp Arg Ser Asp Ile Ala Val Val
        275                 280                 285

Phe Ala Asp Gly Ala Ala Val Gly Glu Leu Asp Val Ala Glu Ala Glu
    290                 295                 300

Ala Leu Ala Ser Val Phe Gly Pro His Arg Val Pro Val Thr Val Pro
305                 310                 315                 320

Lys Thr Leu Thr Gly Arg Leu Tyr Ser Gly Ala Gly Pro Leu Asp Val
                325                 330                 335

Ala Thr Gly Leu Leu Ala Leu Arg Asp Glu Val Val Pro Ala Thr Gly
            340                 345                 350

His Val His Pro Asp Pro Asp Leu Pro Leu Asp Val Val Thr Gly Arg
        355                 360                 365

Pro Arg Ala Met Ala Asp Ala Arg Ala Ala Leu Val Val Ala Arg Gly
    370                 375                 380

His Gly Gly Phe Asn Ser Ala Leu Val Val Arg Gly Ala Ala
385                 390                 395

<210> SEQ ID NO 2
<211> LENGTH: 425
<212> TYPE: PRT
<213> ORGANISM: Streptomyces peucetius

<400> SEQUENCE: 2

Met Thr Gly Thr Ala Ala Arg Thr Ala Ser Ser Gln Leu His Ala Ser
  1               5                  10                  15

Pro Ala Gly Arg Arg Gly Leu Arg Gly Arg Ala Val Val Thr Gly Leu
             20                  25                  30

Gly Ile Val Ala Pro Asn Gly Leu Gly Val Gly Ala Tyr Trp Asp Ala
         35                  40                  45

Val Leu Asn Gly Arg Asn Gly Ile Gly Pro Leu Arg Arg Phe Thr Gly
     50                  55                  60

Asp Gly Arg Leu Gly Arg Leu Ala Gly Glu Val Ser Asp Phe Val Pro
 65                  70                  75                  80

Glu Asp His Leu Pro Lys Arg Leu Leu Ala Gln Thr Asp Pro Met Thr
                 85                  90                  95

Gln Tyr Ala Leu Ala Ala Ala Glu Trp Ala Leu Arg Glu Ser Gly Cys
            100                 105                 110

Ser Pro Ser Ser Pro Leu Glu Ala Gly Val Ile Thr Ala Ser Ala Ser
        115                 120                 125

Gly Gly Phe Ala Phe Gly Gln Arg Glu Leu Gln Asn Leu Trp Ser Lys
    130                 135                 140
```

```
Gly Pro Ala His Val Ser Ala Tyr Met Ser Phe Ala Trp Phe Tyr Ala
145                 150                 155                 160

Val Asn Thr Gly Gln Ile Ala Ile Arg His Asp Leu Arg Gly Pro Val
                165                 170                 175

Gly Val Val Val Ala Glu Gln Ala Gly Gly Leu Asp Ala Leu Ala His
            180                 185                 190

Ala Arg Arg Lys Val Arg Gly Gly Ala Glu Leu Ile Val Ser Gly Ala
        195                 200                 205

Val Asp Ser Ser Leu Cys Pro Tyr Gly Met Ala Ala Gln Val Lys Ser
    210                 215                 220

Gly Arg Leu Ser Gly Ser Asp Asn Pro Thr Ala Gly Tyr Leu Pro Phe
225                 230                 235                 240

Asp Arg Arg Ala Ala Gly His Val Pro Gly Glu Gly Ala Ile Leu
                245                 250                 255

Thr Val Glu Asp Ala Glu Arg Ala Ala Glu Arg Gly Ala Lys Val Tyr
            260                 265                 270

Gly Ser Ile Ala Gly Tyr Gly Ala Ser Phe Asp Pro Pro Gly Ser
        275                 280                 285

Gly Arg Pro Ser Ala Leu Ala Arg Ala Val Glu Thr Ala Leu Ala Asp
    290                 295                 300

Ala Gly Leu Asp Gly Ser Asp Ile Ala Val Val Phe Ala Asp Gly Ala
305                 310                 315                 320

Ala Val Pro Glu Leu Asp Ala Ala Glu Ala Glu Ala Leu Ala Ser Val
                325                 330                 335

Phe Gly Pro Arg Arg Val Pro Val Thr Val Pro Lys Thr Leu Thr Gly
            340                 345                 350

Arg Leu Tyr Ser Gly Ala Gly Pro Leu Asp Val Ala Thr Ala Leu Leu
        355                 360                 365

Ala Leu Arg Asp Glu Val Val Pro Ala Thr Ala His Val Asp Pro Asp
    370                 375                 380

Pro Asp Leu Pro Leu Asp Val Val Thr Gly Arg Pro Arg Ser Leu Ala
385                 390                 395                 400

Asp Ala Arg Ala Ala Leu Leu Val Ala Arg Gly Tyr Gly Gly Phe Asn
                405                 410                 415

Ser Ala Leu Val Val Arg Gly Ala Ala
            420                 425

<210> SEQ ID NO 3
<211> LENGTH: 407
<212> TYPE: PRT
<213> ORGANISM: Streptomyces coelicolor

<400> SEQUENCE: 3

Met Ser Val Leu Ile Thr Gly Val Gly Val Val Ala Pro Asn Gly Leu
1               5                   10                  15

Gly Leu Ala Pro Tyr Trp Ser Ala Val Leu Asp Gly Arg His Gly Leu
                20                  25                  30

Gly Pro Val Thr Arg Phe Asp Val Ser Arg Tyr Pro Ala Thr Leu Ala
            35                  40                  45

Gly Gln Ile Asp Asp Phe His Ala Pro Asp His Ile Pro Gly Arg Leu
        50                  55                  60

Leu Pro Gln Thr Asp Pro Ser Thr Arg Leu Ala Leu Thr Ala Ala Asp
65                  70                  75                  80

Trp Ala Leu Gln Asp Ala Lys Ala Asp Pro Glu Ser Leu Thr Asp Tyr
                85                  90                  95
```

```
Asp Met Gly Val Val Thr Ala Asn Ala Cys Gly Gly Phe Asp Phe Thr
            100                 105                 110

His Arg Glu Phe Arg Lys Leu Trp Ser Glu Gly Pro Lys Ser Val Ser
        115                 120                 125

Val Tyr Glu Ser Phe Ala Trp Phe Tyr Ala Val Asn Thr Gly Gln Ile
    130                 135                 140

Ser Ile Arg His Gly Met Arg Gly Pro Ser Ser Ala Leu Val Ala Glu
145                 150                 155                 160

Gln Ala Gly Gly Leu Asp Ala Leu Gly His Ala Arg Arg Thr Ile Arg
                165                 170                 175

Arg Gly Thr Pro Leu Val Val Ser Gly Gly Val Asp Ser Ala Leu Asp
            180                 185                 190

Pro Trp Gly Trp Val Ser Gln Ile Ala Ser Gly Arg Ile Ser Thr Ala
        195                 200                 205

Thr Asp Pro Asp Arg Ala Tyr Leu Pro Phe Asp Glu Arg Ala Ala Gly
    210                 215                 220

Tyr Val Pro Gly Glu Gly Gly Ala Ile Leu Val Leu Glu Asp Ser Ala
225                 230                 235                 240

Ala Ala Glu Ala Arg Gly Arg His Asp Ala Tyr Gly Glu Leu Ala Gly
                245                 250                 255

Cys Ala Ser Thr Phe Asp Pro Ala Pro Gly Ser Gly Arg Pro Ala Gly
            260                 265                 270

Leu Glu Arg Ala Ile Arg Leu Ala Leu Asn Asp Ala Gly Thr Gly Pro
        275                 280                 285

Glu Asp Val Asp Val Val Phe Ala Asp Gly Ala Gly Val Pro Glu Leu
    290                 295                 300

Asp Ala Ala Glu Ala Arg Ala Ile Gly Arg Val Phe Gly Arg Glu Gly
305                 310                 315                 320

Val Pro Val Thr Val Pro Lys Thr Thr Thr Gly Arg Leu Tyr Ser Gly
                325                 330                 335

Gly Gly Pro Leu Asp Val Val Thr Ala Leu Met Ser Leu Arg Glu Gly
            340                 345                 350

Val Ile Ala Pro Thr Ala Gly Val Thr Ser Val Pro Arg Glu Tyr Gly
        355                 360                 365

Ile Asp Leu Val Leu Gly Glu Pro Arg Ser Thr Ala Pro Arg Thr Ala
    370                 375                 380

Leu Val Leu Ala Arg Gly Arg Trp Gly Phe Asn Ser Ala Ala Val Leu
385                 390                 395                 400

Arg Arg Phe Ala Pro Thr Pro
                405

<210> SEQ ID NO 4
<211> LENGTH: 403
<212> TYPE: PRT
<213> ORGANISM: Saccharopolyspora hirsuta

<400> SEQUENCE: 4

Met Ser Thr Trp Val Thr Gly Met Gly Val Val Ala Pro Asn Gly Leu
  1               5                  10                  15

Gly Ala Asp Asp His Trp Ala Ala Thr Leu Lys Gly Arg His Gly Ile
                20                  25                  30

Ser Arg Leu Ser Arg Phe Asp Pro Thr Gly Tyr Pro Ala Glu Leu Ala
            35                  40                  45

Gly Gln Val Leu Asp Phe Asp Ala Thr Glu His Leu Pro Lys Arg Leu
```

```
            50                  55                  60
Leu Pro Gln Thr Asp Val Ser Thr Arg Phe Ala Leu Ala Ala Ala Ala
 65                  70                  75                  80

Trp Ala Leu Ala Asp Ala Glu Val Asp Pro Ala Glu Leu Pro Glu Tyr
                 85                  90                  95

Gly Thr Gly Val Ile Thr Ser Asn Ala Thr Gly Gly Phe Glu Phe Thr
                100                 105                 110

His Arg Glu Phe Arg Lys Leu Trp Ala Gln Gly Pro Glu Phe Val Ser
                115                 120                 125

Val Tyr Glu Ser Phe Ala Trp Phe Tyr Ala Val Asn Thr Gly Gln Ile
            130                 135                 140

Ser Ile Arg His Gly Leu Arg Gly Pro Gly Ser Val Leu Val Ala Glu
145                 150                 155                 160

Gln Ala Gly Gly Leu Asp Ala Val Gly His Gly Gly Ala Val Arg Asn
                165                 170                 175

Gly Thr Pro Met Val Val Thr Gly Gly Val Asp Ser Ser Phe Asp Pro
                180                 185                 190

Trp Gly Trp Val Ser His Val Ser Ser Gly Arg Val Ser Arg Ala Thr
            195                 200                 205

Asp Pro Gly Arg Ala Tyr Leu Pro Phe Asp Val Ala Ala Asn Gly Tyr
            210                 215                 220

Val Pro Gly Glu Gly Gly Ala Ile Leu Leu Leu Glu Asp Ala Glu Ser
225                 230                 235                 240

Ala Lys Ala Arg Gly Ala Thr Gly Tyr Gly Glu Ile Ala Gly Tyr Ala
                245                 250                 255

Ala Thr Phe Asp Pro Ala Pro Gly Ser Glu Arg Pro Pro Ala Leu Arg
                260                 265                 270

Arg Ala Ile Glu Leu Ala Leu Ala Asp Ala Glu Leu Arg Pro Glu Gln
            275                 280                 285

Val Asp Val Val Phe Ala Asp Ala Ala Gly Val Ala Glu Leu Asp Ala
            290                 295                 300

Ile Glu Ala Ala Ala Ile Arg Glu Leu Phe Gly Pro Ser Gly Val Pro
305                 310                 315                 320

Val Thr Ala Pro Lys Thr Met Thr Gly Arg Leu Tyr Ser Gly Gly Gly
                325                 330                 335

Pro Leu Asp Leu Val Ala Ala Leu Leu Ala Ile Arg Asp Gly Val Ile
                340                 345                 350

Pro Pro Thr Val His Thr Ala Glu Pro Val Pro Glu His Gln Leu Asp
            355                 360                 365

Leu Val Thr Gly Asp Pro Arg His Gln Gln Leu Gly Thr Ala Leu Val
            370                 375                 380

Leu Ala Arg Gly Lys Trp Gly Phe Asn Ser Ala Val Val Arg Gly
385                 390                 395                 400

Val Thr Gly

<210> SEQ ID NO 5
<211> LENGTH: 415
<212> TYPE: PRT
<213> ORGANISM: Streptomyces violaceoruber

<400> SEQUENCE: 5

Met Ser Thr Pro Asp Arg Arg Ala Val Val Thr Gly Leu Ser Val
 1               5                  10                  15

Ala Ala Pro Gly Gly Leu Gly Thr Glu Arg Tyr Trp Lys Ser Leu Leu
```

```
                  20                  25                  30
Thr Gly Glu Asn Gly Ile Ala Glu Leu Ser Arg Phe Asp Ala Ser Arg
             35                  40                  45
Tyr Pro Ser Arg Leu Ala Gly Gln Ile Asp Asp Phe Glu Ala Ser Glu
 50                  55                  60
His Leu Pro Ser Arg Leu Leu Pro Gln Thr Asp Val Ser Thr Arg Tyr
 65                  70                  75                  80
Ala Leu Ala Ala Ala Asp Trp Ala Leu Ala Asp Ala Gly Val Gly Pro
                 85                  90                  95
Glu Ser Gly Leu Asp Asp Tyr Asp Leu Gly Val Val Thr Ser Thr Ala
                100                 105                 110
Gln Gly Gly Phe Asp Phe Thr His Arg Glu Phe His Lys Leu Trp Ser
            115                 120                 125
Gln Gly Pro Ala Tyr Val Ser Val Tyr Glu Ser Phe Ala Trp Phe Tyr
130                 135                 140
Ala Val Asn Thr Gly Gln Ile Ser Ile Arg Asn Thr Met Arg Gly Pro
145                 150                 155                 160
Ser Ala Ala Leu Val Gly Glu Gln Ala Gly Gly Leu Asp Ala Ile Gly
                165                 170                 175
His Ala Arg Arg Thr Val Arg Arg Gly Pro Gly Trp Cys Ser Ala Val
            180                 185                 190
Ala Ser Thr Arg Arg Ser Thr Arg Gly Ala Ser Ser Ser Gln Leu Ser
        195                 200                 205
Gly Gly Leu Val Ser Thr Val Ala Asp Pro Glu Arg Ala Tyr Leu Pro
210                 215                 220
Phe Asp Val Asp Ala Ser Gly Tyr Val Pro Gly Glu Gly Gly Ala Val
225                 230                 235                 240
Leu Ile Val Glu Asp Ala Asp Ser Ala Arg Ala Arg Gly Ala Glu Arg
                245                 250                 255
Ile Tyr Val Arg Ser Pro Leu Arg Arg Asp Pro Ala Pro Gly Ser Gly
            260                 265                 270
Arg Pro Pro Ala Leu Gly Arg Ala Ala Glu Leu Ala Leu Ala Glu Ala
        275                 280                 285
Gly Leu Thr Pro Ala Asp Ile Ser Val Val Phe Ala Asp Gly Ala Gly
290                 295                 300
Val Pro Glu Leu Asp Arg Ala Glu Ala Asp Thr Leu Ala Arg Leu Phe
305                 310                 315                 320
Gly Pro Arg Gly Val Pro Val Thr Ala Pro Lys Ala Leu Thr Gly Arg
                325                 330                 335
Leu Cys Ala Gly Gly Pro Ala Asp Leu Ala Ala Ala Leu Leu Ala
            340                 345                 350
Leu Arg Asp Gln Val Ile Pro Ala Thr Gly Arg His Arg Ala Val Pro
        355                 360                 365
Asp Ala Tyr Ala Leu Asp Leu Val Thr Gly Arg Pro Arg Glu Ala Ala
    370                 375                 380
Leu Ser Ala Ala Leu Val Leu Ala Arg Gly Arg His Gly Phe Asn Ser
385                 390                 395                 400
Ala Val Val Val Thr Leu Arg Gly Ser Asp His Arg Arg Pro Thr
                405                 410                 415

<210> SEQ ID NO 6
<211> LENGTH: 409
<212> TYPE: PRT
<213> ORGANISM: Streptomyces nogalater
```

<400> SEQUENCE: 6

```
Met Thr Ala Ala Val Val Thr Gly Leu Gly Val Ala Pro Thr
  1               5                  10                  15
Gly Leu Gly Val Arg Glu His Trp Ser Ser Thr Val Arg Gly Ala Ser
             20                  25                  30
Ala Ile Gly Pro Val Thr Arg Phe Asp Ala Gly Arg Tyr Pro Ser Lys
         35                  40                  45
Leu Ala Gly Glu Val Pro Gly Phe Val Pro Glu Asp His Leu Pro Ser
     50                  55                  60
Arg Leu Met Pro Gln Thr Asp His Met Thr Arg Leu Ala Leu Val Ala
 65                  70                  75                  80
Ala Asp Trp Ala Phe Gln Asp Ala Ala Val Asp Pro Ser Lys Leu Pro
                 85                  90                  95
Glu Tyr Gly Val Gly Val Val Thr Ala Ser Ser Ala Gly Gly Phe Glu
            100                 105                 110
Phe Gly His Arg Glu Leu Gln Asn Leu Trp Ser Leu Gly Pro Gln Tyr
        115                 120                 125
Val Ser Ala Tyr Gln Ser Phe Ala Trp Phe Tyr Ala Val Asn Thr Gly
    130                 135                 140
Gln Val Ser Ile Arg His Gly Leu Arg Gly Pro Gly Val Leu Val
145                 150                 155                 160
Thr Glu Gln Ala Gly Gly Leu Asp Ala Leu Gly Gln Ala Arg Arg Gln
                165                 170                 175
Leu Arg Arg Gly Leu Pro Met Val Val Ala Gly Ala Val Asp Gly Ser
            180                 185                 190
Pro Cys Pro Trp Gly Trp Val Ala Gln Leu Ser Ser Gly Gly Leu Ser
        195                 200                 205
Thr Ser Asp Asp Pro Arg Arg Ala Tyr Leu Pro Phe Asp Ala Ala Ala
    210                 215                 220
Gly Gly His Val Pro Gly Glu Gly Gly Ala Leu Leu Val Leu Glu Ser
225                 230                 235                 240
Asp Glu Ser Ala Arg Ala Arg Gly Val Thr Arg Trp Tyr Gly Arg Ile
                245                 250                 255
Asp Gly Tyr Ala Ala Thr Phe Asp Pro Pro Gly Ser Gly Arg Pro
            260                 265                 270
Pro Asn Leu Leu Arg Ala Ala Gln Ala Ala Leu Asp Asp Ala Glu Val
        275                 280                 285
Gly Pro Glu Ala Val Asp Val Phe Ala Asp Ala Ser Gly Thr Pro
    290                 295                 300
Asp Glu Asp Ala Ala Glu Ala Asp Ala Val Arg Arg Leu Phe Gly Pro
305                 310                 315                 320
Tyr Gly Val Pro Val Thr Ala Pro Lys Thr Met Thr Gly Arg Leu Ser
                325                 330                 335
Ala Gly Gly Ala Ala Leu Asp Val Ala Thr Ala Leu Leu Ala Leu Arg
            340                 345                 350
Glu Gly Val Val Pro Pro Thr Val Asn Val Ser Arg Pro Arg Pro Glu
        355                 360                 365
Tyr Glu Leu Asp Leu Val Leu Ala Pro Arg Arg Thr Pro Leu Ala Arg
    370                 375                 380
Ala Leu Val Leu Ala Arg Gly Arg Gly Phe Asn Ala Ala Met Val
385                 390                 395                 400
Val Ala Gly Pro Arg Ala Glu Thr Arg
```

-continued

```
                405

<210> SEQ ID NO 7
<211> LENGTH: 409
<212> TYPE: PRT
<213> ORGANISM: Streptomyces glaucescens

<400> SEQUENCE: 7

Met Ser Ala Pro Ala Pro Val Val Thr Gly Leu Gly Ile Val Ala
 1               5                  10                  15

Pro Asn Gly Thr Gly Thr Glu Glu Tyr Trp Ala Ala Thr Leu Ala Gly
                20                  25                  30

Lys Ser Gly Ile Asp Val Ile Gln Arg Phe Asp Pro His Gly Tyr Pro
            35                  40                  45

Val Arg Val Gly Gly Glu Val Leu Ala Phe Asp Ala Ala His Leu
     50                  55                  60

Pro Gly Arg Leu Leu Pro Gln Thr Asp Arg Met Thr Gln His Ala Leu
 65                  70                  75                  80

Val Ala Ala Glu Trp Ala Leu Ala Asp Ala Gly Leu Glu Pro Glu Lys
                 85                  90                  95

Gln Asp Glu Tyr Gly Leu Gly Val Leu Thr Ala Ala Gly Ala Gly Gly
                100                 105                 110

Phe Glu Phe Gly Gln Arg Glu Met Gln Lys Leu Trp Gly Thr Gly Pro
            115                 120                 125

Glu Arg Val Ser Ala Tyr Gln Ser Phe Ala Trp Phe Tyr Ala Val Asn
    130                 135                 140

Thr Gly Gln Ile Ser Ile Arg His Gly Met Arg Gly His Ser Ser Val
145                 150                 155                 160

Phe Val Thr Glu Gln Ala Gly Gly Leu Asp Ala Ala His Ala Ala
                165                 170                 175

Arg Leu Leu Arg Lys Gly Thr Leu Asn Thr Ala Leu Thr Gly Gly Cys
            180                 185                 190

Glu Ala Ser Leu Cys Pro Trp Gly Leu Val Ala Gln Ile Pro Ser Gly
        195                 200                 205

Phe Leu Ser Glu Ala Thr Asp Pro His Asp Ala Tyr Leu Pro Phe Asp
    210                 215                 220

Ala Arg Ala Ala Gly Tyr Val Pro Gly Glu Gly Ala Met Leu Val
225                 230                 235                 240

Ala Glu Arg Ala Asp Ser Ala Arg Glu Arg Asp Ala Ala Thr Val Tyr
                245                 250                 255

Gly Arg Ile Ala Gly His Ala Ser Thr Phe Asp Ala Arg Pro Gly Thr
            260                 265                 270

Gly Arg Pro Thr Gly Pro Ala Arg Ala Ile Arg Leu Ala Leu Glu Glu
        275                 280                 285

Ala Arg Val Ala Pro Glu Asp Val Asp Val Val Tyr Ala Asp Ala Ala
    290                 295                 300

Gly Val Pro Ala Leu Asp Arg Ala Glu Ala Glu Ala Leu Ala Glu Val
305                 310                 315                 320

Phe Gly Pro Gly Ala Val Pro Val Thr Ala Pro Lys Thr Met Thr Gly
                325                 330                 335

Arg Leu Tyr Ala Gly Gly Ala Ala Asp Val Ala Thr Ala Leu Leu
            340                 345                 350

Ser Ile Arg Asp Cys Val Val Pro Pro Thr Val Gly Thr Gly Ala Pro
        355                 360                 365
```

```
Ala Pro Gly Leu Gly Ile Asp Leu Val Leu His Gln Pro Arg Glu Leu
    370                 375                 380
Arg Val Asp Thr Ala Leu Val Val Ala Arg Gly Met Gly Gly Phe Asn
385                 390                 395                 400
Ser Ala Leu Val Val Arg Arg His Gly
                405

<210> SEQ ID NO 8
<211> LENGTH: 402
<212> TYPE: PRT
<213> ORGANISM: Streptomyces cinnamonensis

<400> SEQUENCE: 8

Met Thr Pro Val Ala Val Thr Gly Met Gly Ile Ala Ala Pro Asn Gly
  1                 5                  10                  15
Leu Gly Arg Pro Thr Thr Gly Arg Pro Pro Trp Ala Pro Arg Ala Ala
                 20                  25                  30
Ser Ala Ala Ser Thr Arg Phe Asp Pro Ser Gly Tyr Pro Ala Gln Leu
             35                  40                  45
Ala Gly Glu Ile Pro Gly Phe Arg Ala Ala Glu His Leu Pro Gly Arg
         50                  55                  60
Leu Val Pro Gln Thr Asp Arg Val Thr Arg Leu Ser Leu Ala Ala Ala
 65                  70                  75                  80
Asp Trp Ala Leu Ala Asp Ala Gly Val Glu Val Ala Ala Phe Asp Pro
                 85                  90                  95
Leu Asp Met Gly Val Val Thr Ala Ser His Ala Gly Gly Phe Glu Phe
            100                 105                 110
Gly Gln Asp Glu Leu Gln Lys Leu Leu Gly Gln Gly Gln Pro Val Leu
        115                 120                 125
Ser Ala Tyr Gln Ser Phe Ala Trp Phe Tyr Ala Val Asn Ser Gly Gln
    130                 135                 140
Ile Ser Ile Arg His Gly Met Lys Gly Pro Ser Gly Val Val Val Ser
145                 150                 155                 160
Asp Gln Ala Gly Gly Leu Asp Ala Leu Ala Gln Ala Arg Arg Leu Val
                165                 170                 175
Arg Lys Gly Thr Pro Leu Ile Val Cys Gly Ala Val Glu Pro Arg Ser
            180                 185                 190
Ala Pro Gly Ala Gly Ser Pro Ser Ser Pro Ala Gly Gly Met Ser Asp
        195                 200                 205
Ser Asp Glu Pro Asn Arg Ala Tyr Leu Pro Phe Asp Arg Asp Gly Arg
    210                 215                 220
Gly Tyr Val Pro Gly Gly Gly Arg Gly Val Val Pro Pro Leu Glu Arg
225                 230                 235                 240
Ala Glu Ala Ala Pro Ala Arg Gly Ala Glu Val Tyr Gly Glu Ala Gly
                245                 250                 255
Pro Leu Ala Arg Leu Pro Ala Pro His Ser Gly Arg Gly Ser Thr Arg
            260                 265                 270
Ala His Ala Ile Arg Thr Ala Leu Asp Asp Ala Gly Thr Ala Pro Gly
        275                 280                 285
Asp Ile Arg Arg Val Phe Ala Asp Gly Gly Arg Tyr Pro Asn Asp
    290                 295                 300
Arg Ala Glu Ala Glu Ala Ile Ser Glu Val Phe Gly Pro Gly Arg Val
305                 310                 315                 320
Pro Val Thr Cys Pro Arg Thr Met Thr Gly Arg Leu His Ser Gly Ala
                325                 330                 335
```

```
Ala Pro Leu Asp Val Ala Cys Ala Leu Leu Ala Met Arg Ala Gly Val
            340                 345                 350

Ile Pro Pro Thr Val His Ile Asp Pro Cys Pro Glu Tyr Asp Leu Asp
            355                 360                 365

Leu Val Leu Tyr Gln Val Arg Pro Ala Ala Leu Arg Thr Ala Leu Gly
            370                 375                 380

Gly Ala Arg Gly His Gly Gly Phe Asn Ser Ala Leu Val Val Arg Ala
385                 390                 395                 400

Gly Gln

<210> SEQ ID NO 9
<211> LENGTH: 404
<212> TYPE: PRT
<213> ORGANISM: Streptomyces venezuelae

<400> SEQUENCE: 9

Met Ser Ala Ser Val Val Thr Gly Leu Gly Val Ala Ala Pro Asn
1               5                   10                  15

Gly Leu Gly Arg Glu Asp Phe Trp Ala Ser Thr Leu Gly Gly Lys Ser
            20                  25                  30

Gly Ile Gly Pro Leu Thr Arg Phe Asp Pro Thr Gly Tyr Pro Ala Arg
            35                  40                  45

Leu Ala Gly Glu Val Pro Gly Phe Ala Ala Glu His Leu Pro Ser
            50                  55                  60

Arg Leu Leu Pro Gln Thr Asp Arg Met Thr Arg Leu Ala Leu Val Ala
65                  70                  75                  80

Ala Asp Trp Ala Leu Ala Asp Ala Gly Val Arg Pro Glu Glu Gln Asp
                85                  90                  95

Asp Phe Asp Met Gly Val Val Thr Ala Ser Ala Ser Gly Gly Phe Glu
                100                 105                 110

Phe Gly Gln Gly Glu Leu Gln Lys Leu Trp Ser Gln Gly Ser Gln Tyr
            115                 120                 125

Val Ser Ala Tyr Gln Ser Phe Ala Trp Phe Tyr Ala Val Asn Ser Gly
130                 135                 140

Gln Ile Ser Ile Arg Asn Gly Met Lys Gly Pro Ser Gly Val Val Val
145                 150                 155                 160

Ser Asp Gln Ala Gly Gly Leu Asp Ala Val Ala Gln Ala Arg Arg Gln
                165                 170                 175

Ile Arg Lys Gly Thr Arg Leu Ile Val Ser Gly Gly Val Asp Ala Ser
            180                 185                 190

Leu Cys Pro Trp Gly Trp Val Ala His Val Ala Ser Asp Arg Leu Ser
            195                 200                 205

Thr Ser Glu Glu Pro Ala Arg Gly Tyr Leu Pro Phe Asp Arg Glu Ala
210                 215                 220

Gln Gly His Val Pro Gly Glu Gly Gly Ala Ile Leu Val Met Glu Ala
225                 230                 235                 240

Ala Glu Ala Ala Arg Glu Arg Gly Ala Arg Ile Tyr Gly Glu Ile Ala
                245                 250                 255

Gly Tyr Gly Ser Thr Phe Asp Pro Arg Pro Gly Ser Gly Arg Glu Pro
            260                 265                 270

Gly Leu Arg Lys Ala Ile Glu Leu Ala Leu Ala Asp Ala Gly Ala Ala
            275                 280                 285

Pro Gly Asp Ile Asp Val Val Phe Ala Asp Ala Ala Ala Val Pro Glu
290                 295                 300
```

-continued

Leu Asp Arg Val Glu Ala Glu Ala Leu Asn Ala Val Phe Gly Thr Gly
305                 310                 315                 320

Ala Val Pro Val Thr Ala Pro Lys Thr Met Thr Gly Arg Leu Tyr Ser
                325                 330                 335

Gly Ala Ala Pro Leu Asp Leu Ala Ala Ala Phe Leu Ala Met Asp Glu
                340                 345                 350

Gly Val Ile Pro Pro Thr Val Asn Val Glu Pro Asp Ala Ala Tyr Gly
            355                 360                 365

Leu Asp Leu Val Val Gly Gly Pro Arg Thr Ala Glu Val Asn Thr Ala
370                 375                 380

Leu Val Ile Ala Arg Gly His Gly Gly Phe Asn Ser Ala Met Val Val
385                 390                 395                 400

Arg Ser Ala Asn

<210> SEQ ID NO 10
<211> LENGTH: 424
<212> TYPE: PRT
<213> ORGANISM: Streptomyces coelicolor

<400> SEQUENCE: 10

Met Ser Gly Pro Gln Arg Thr Gly Thr Gly Gly Ser Arg Arg Ala
1               5                   10                  15

Val Val Thr Gly Leu Gly Val Leu Ser Pro His Gly Thr Gly Val Glu
                20                  25                  30

Ala His Trp Lys Ala Val Ala Asp Gly Thr Ser Ser Leu Gly Pro Val
            35                  40                  45

Thr Arg Glu Gly Cys Ala His Leu Pro Leu Arg Val Ala Gly Glu Val
        50                  55                  60

His Gly Phe Asp Ala Ala Glu Thr Val Glu Asp Arg Phe Leu Val Gln
65                  70                  75                  80

Thr Asp Arg Phe Thr His Phe Ala Leu Ser Ala Thr Gln His Ala Leu
                85                  90                  95

Ala Asp Ala Arg Phe Gly Arg Ala Asp Val Asp Ser Pro Tyr Ser Val
            100                 105                 110

Gly Val Val Thr Ala Ala Gly Ser Gly Gly Gly Glu Phe Gly Gln Arg
        115                 120                 125

Glu Leu Gln Asn Leu Trp Gly His Gly Ser Arg His Val Gly Pro Tyr
130                 135                 140

Gln Ser Ile Ala Trp Phe Tyr Ala Ala Ser Thr Gly Gln Val Ser Ile
145                 150                 155                 160

Arg Asn Asp Phe Lys Gly Pro Cys Gly Val Val Ala Ala Asp Glu Ala
                165                 170                 175

Gly Gly Leu Asp Ala Leu Ala His Ala Ala Leu Ala Val Arg Asn Gly
            180                 185                 190

Thr Asp Thr Val Val Cys Gly Ala Thr Glu Ala Pro Leu Ala Pro Tyr
        195                 200                 205

Ser Ile Val Cys Gln Leu Gly Tyr Pro Glu Leu Ser Arg Ala Thr Glu
    210                 215                 220

Pro Asp Arg Ala Tyr Arg Pro Phe Thr Glu Ala Ala Cys Gly Phe Ala
225                 230                 235                 240

Pro Ala Glu Gly Gly Ala Val Leu Val Glu Glu Ala Ala Ala
                245                 250                 255

Arg Glu Arg Gly Ala Asp Val Arg Ala Thr Val Ala Gly His Ala Ala
            260                 265                 270

-continued

```
Thr Phe Thr Gly Ala Gly Arg Trp Ala Glu Ser Arg Glu Gly Leu Ala
            275                 280                 285

Arg Ala Ile Gln Gly Ala Leu Ala Glu Ala Gly Cys Arg Pro Glu Glu
        290                 295                 300

Val Asp Val Val Phe Ala Asp Ala Leu Gly Val Pro Glu Ala Asp Arg
305                 310                 315                 320

Ala Glu Ala Leu Ala Leu Ala Asp Ala Leu Gly Pro His Ala Ala Arg
                325                 330                 335

Val Pro Val Thr Ala Pro Lys Thr Gly Thr Gly Arg Ala Tyr Cys Ala
            340                 345                 350

Ala Pro Val Leu Asp Val Ala Thr Ala Val Leu Ala Met Glu His Gly
        355                 360                 365

Leu Ile Pro Pro Thr Pro His Val Leu Asp Val Cys His Asp Leu Asp
    370                 375                 380

Leu Val Thr Gly Arg Ala Arg Pro Ala Glu Pro Arg Thr Ala Leu Val
385                 390                 395                 400

Leu Ala Arg Gly Leu Met Gly Ser Asn Ser Ala Leu Val Leu Arg Arg
                405                 410                 415

Gly Ala Val Pro Pro Glu Gly Arg
            420
```

<210> SEQ ID NO 11
<211> LENGTH: 421
<212> TYPE: PRT
<213> ORGANISM: Streptomyces violaceoruber

<400> SEQUENCE: 11

```
Met Thr Arg Arg Val Val Ile Thr Gly Val Gly Val Arg Ala Pro Gly
  1               5                  10                  15

Gly Ser Gly Thr Lys Glu Phe Trp Asp Leu Leu Thr Ala Gly Arg Thr
            20                  25                  30

Ala Thr Arg Pro Ile Ser Phe Phe Asp Ala Ser Pro Phe Arg Ser Arg
        35                  40                  45

Ile Ala Gly Glu Ile Asp Phe Asp Ala Val Ala Glu Gly Phe Ser Pro
    50                  55                  60

Arg Glu Val Arg Arg Met Asp Arg Ala Thr Gln Phe Ala Val Ala Cys
65                  70                  75                  80

Thr Arg Asp Ala Leu Ala Asp Ser Gly Leu Asp Thr Gly Ala Leu Asp
                85                  90                  95

Pro Ser Arg Ile Gly Val Ala Leu Gly Ser Ala Val Ala Ser Ala Thr
            100                 105                 110

Ser Leu Glu Asn Glu Tyr Leu Val Met Ser Asp Ser Gly Arg Glu Trp
        115                 120                 125

Leu Val Asp Pro Ala His Leu Ser Pro Met Met Phe Asp Tyr Leu Ser
    130                 135                 140

Pro Gly Val Met Pro Ala Glu Val Ala Trp Ala Ala Gly Ala Glu Gly
145                 150                 155                 160

Pro Val Thr Met Val Ser Asp Gly Cys Thr Ser Gly Leu Asp Ser Val
                165                 170                 175

Gly Tyr Ala Val Gln Gly Thr Arg Glu Gly Ser Ala Asp Val Val Val
            180                 185                 190

Ala Gly Ala Ala Asp Thr Pro Val Ser Pro Ile Val Val Ala Cys Phe
        195                 200                 205

Asp Ala Ile Lys Ala Thr Thr Pro Arg Asn Asp Asp Pro Ala His Ala
```

-continued

```
                210                 215                 220
Ser Arg Pro Phe Asp Gly Thr Arg Asn Gly Phe Val Leu Ala Glu Gly
225                 230                 235                 240

Ala Ala Met Phe Val Leu Glu Glu Tyr Glu Ala Ala Gln Arg Arg Gly
                245                 250                 255

Ala His Ile Tyr Ala Glu Val Gly Gly Tyr Ala Thr Arg Ser Gln Ala
                260                 265                 270

Tyr His Met Thr Gly Leu Lys Lys Asp Gly Arg Glu Met Ala Glu Ser
                275                 280                 285

Ile Arg Ala Ala Leu Asp Glu Ala Arg Leu Asp Arg Thr Ala Val Asp
290                 295                 300

Tyr Val Asn Ala His Gly Ser Gly Thr Lys Gln Asn Asp Arg His Glu
305                 310                 315                 320

Thr Ala Ala Phe Lys Arg Ser Leu Gly Glu His Ala Tyr Ala Val Pro
                325                 330                 335

Val Ser Ser Ile Lys Ser Met Gly Gly His Ser Leu Gly Ala Ile Gly
                340                 345                 350

Ser Ile Glu Ile Ala Ala Ser Val Leu Ala Ile Glu His Asn Val Val
                355                 360                 365

Pro Pro Thr Ala Asn Leu His Thr Pro Asp Pro Glu Cys Asp Leu Asp
370                 375                 380

Tyr Val Pro Leu Thr Ala Arg Glu Gln Arg Val Asp Thr Val Leu Thr
385                 390                 395                 400

Val Gly Ser Gly Phe Gly Gly Phe Gln Ser Ala Met Val Leu His Arg
                405                 410                 415

Pro Glu Glu Ala Ala
                420

<210> SEQ ID NO 12
<211> LENGTH: 422
<212> TYPE: PRT
<213> ORGANISM: Saccharopolyspora hirsuta

<400> SEQUENCE: 12

Met Thr Arg Arg Val Val Ile Thr Gly Val Gly Val Arg Ala Pro Gly
1               5                   10                  15

Gly Leu Gly Ala Lys Asn Phe Trp Glu Leu Leu Thr Ser Gly Arg Thr
                20                  25                  30

Ala Thr Arg Arg Ile Ser Phe Phe Asp Pro Thr Pro Asn Arg Ser Gln
                35                  40                  45

Ile Ala Ala Glu Cys Asp Phe Asp Pro Glu His Glu Gly Leu Ser Pro
            50                  55                  60

Arg Glu Ile Arg Arg Met Asp Arg Ala Ala Gln Phe Ala Val Val Cys
65                  70                  75                  80

Thr Arg Asp Ala Val Ala Asp Ser Gly Leu Glu Phe Glu Gln Val Pro
                85                  90                  95

Pro Glu Arg Ile Gly Val Ser Leu Gly Ser Ala Val Ala Ala Thr
                100                 105                 110

Ser Leu Glu Gln Glu Tyr Leu Val Leu Ser Asp Gly Arg Glu Trp
            115                 120                 125

Gln Val Asp Pro Ala Tyr Leu Ser Ala His Met Phe Asp Tyr Leu Ser
            130                 135                 140

Pro Gly Val Met Pro Ala Glu Val Ala Trp Thr Val Gly Ala Glu Gly
145                 150                 155                 160
```

```
Pro Val Ala Met Val Ser Asp Gly Cys Thr Ser Gly Leu Asp Ser Leu
            165                 170                 175

Ser His Ala Cys Ser Leu Ile Ala Glu Gly Thr Thr Asp Val Met Val
            180                 185                 190

Ala Gly Ala Ala Asp Thr Pro Ile Thr Pro Ile Val Val Ser Cys Phe
            195                 200                 205

Asp Ala Ile Lys Ala Thr Thr Pro Arg Asn Asp Asp Pro Glu His Ala
210                 215                 220

Ser Arg Pro Phe Asp Asn Ser Arg Asn Gly Phe Val Leu Ala Glu Gly
225                 230                 235                 240

Ala Ala Leu Phe Val Leu Glu Glu Leu Glu His Ala Arg Ala Arg Gly
                245                 250                 255

Ala His Val Tyr Ala Glu Ile Ser Gly Cys Ala Thr Arg Leu Asn Ala
            260                 265                 270

Tyr His Met Thr Gly Leu Lys Thr Asp Gly Arg Glu Met Ala Glu Ala
            275                 280                 285

Ile Arg Val Ala Leu Asp Leu Ala Arg Ile Asp Pro Thr Asp Ile Asp
            290                 295                 300

Tyr Ile Asn Ala His Gly Ser Gly Thr Lys Gln Asn Asp Arg His Glu
305                 310                 315                 320

Thr Ala Ala Phe Lys Arg Ser Leu Gly Glu His Ala Tyr Arg Thr Pro
                325                 330                 335

Val Ser Ser Ile Lys Ser Met Val Gly His Ser Leu Gly Ala Ile Gly
            340                 345                 350

Ser Ile Glu Val Ala Ala Cys Ala Leu Ala Ile Glu His Gly Val Val
            355                 360                 365

Pro Pro Thr Ala Asn Leu His Glu Pro Asp Pro Glu Cys Asp Leu Asp
            370                 375                 380

Tyr Val Pro Leu Thr Ala Arg Glu Gln Arg Val Asp Thr Val Leu Ser
385                 390                 395                 400

Val Gly Ser Gly Phe Gly Phe Gln Ser Ala Met Val Leu Arg Arg
                405                 410                 415

Leu Gly Gly Ala Asn Ser
            420
```

<210> SEQ ID NO 13
<211> LENGTH: 424
<212> TYPE: PRT
<213> ORGANISM: Streptomyces coelicolor

<400> SEQUENCE: 13

```
Met Lys Arg Arg Val Val Ile Thr Gly Val Gly Val Arg Ala Pro Gly
1               5                   10                  15

Gly Asn Gly Thr Arg Gln Phe Trp Glu Leu Leu Thr Ser Gly Arg Thr
            20                  25                  30

Ala Thr Arg Arg Ile Ser Phe Asp Pro Ser Pro Tyr Arg Ser Gln
            35                  40                  45

Val Ala Ala Glu Ala Asp Phe Asp Pro Val Ala Glu Gly Phe Gly Pro
        50                  55                  60

Arg Glu Leu Asp Arg Met Asp Arg Ala Ser Gln Phe Ala Val Ala Cys
65                  70                  75                  80

Ala Arg Glu Ala Phe Ala Ala Ser Gly Leu Asp Pro Asp Thr Leu Asp
                85                  90                  95

Pro Ala Arg Val Gly Val Ser Leu Gly Ser Ala Val Ala Ala Ala Thr
            100                 105                 110
```

-continued

Ser Leu Glu Arg Glu Tyr Leu Leu Ser Asp Ser Gly Arg Asp Trp
            115                 120                 125

Glu Val Asp Ala Ala Trp Leu Ser Arg His Met Phe Asp Tyr Leu Val
    130                 135                 140

Pro Ser Val Met Pro Ala Glu Val Ala Trp Ala Val Gly Ala Glu Gly
145                 150                 155                 160

Pro Val Thr Met Val Ser Thr Gly Cys Thr Ser Gly Leu Asp Ser Val
                165                 170                 175

Gly Asn Ala Val Arg Ala Ile Glu Glu Gly Ser Ala Asp Val Met Phe
            180                 185                 190

Ala Gly Ala Ala Asp Thr Pro Ile Thr Pro Ile Val Val Ala Cys Phe
        195                 200                 205

Asp Ala Ile Arg Ala Thr Thr Ala Arg Asn Asp Asp Pro Glu His Ala
    210                 215                 220

Ser Arg Pro Phe Asp Gly Thr Arg Asp Gly Phe Val Leu Ala Glu Gly
225                 230                 235                 240

Ala Ala Met Phe Val Leu Glu Asp Tyr Asp Ser Ala Leu Ala Arg Gly
                245                 250                 255

Ala Arg Ile His Ala Glu Ile Ser Gly Tyr Ala Thr Arg Cys Asn Ala
            260                 265                 270

Tyr His Met Thr Gly Leu Lys Ala Asp Gly Arg Glu Met Ala Glu Thr
        275                 280                 285

Ile Arg Val Ala Leu Asp Glu Ser Arg Thr Asp Ala Thr Asp Ile Asp
    290                 295                 300

Tyr Ile Asn Ala His Gly Ser Gly Thr Arg Gln Asn Asp Arg His Glu
305                 310                 315                 320

Thr Ala Ala Tyr Lys Arg Ala Leu Gly Glu His Ala Arg Arg Thr Pro
                325                 330                 335

Val Ser Ser Ile Lys Ser Met Val Gly His Ser Leu Gly Ala Ile Gly
            340                 345                 350

Ser Leu Glu Ile Ala Ala Cys Val Leu Ala Leu Glu His Gly Val Val
        355                 360                 365

Pro Pro Thr Ala Asn Leu Arg Thr Ser Asp Pro Glu Cys Asp Leu Asp
    370                 375                 380

Tyr Val Pro Leu Glu Ala Arg Glu Arg Lys Leu Arg Ser Val Leu Thr
385                 390                 395                 400

Val Gly Ser Gly Phe Gly Gly Phe Gln Ser Ala Met Val Leu Arg Asp
                405                 410                 415

Ala Glu Thr Ala Gly Ala Ala Ala
            420

<210> SEQ ID NO 14
<211> LENGTH: 420
<212> TYPE: PRT
<213> ORGANISM: Streptomyces cinnamonensis

<400> SEQUENCE: 14

Met Thr Gln Arg Arg Val Ala Ile Thr Gly Ile Glu Val Leu Ala Pro
 1               5                  10                  15

Gly Gly Leu Gly Arg Lys Glu Phe Trp Gln Leu Leu Ser Glu Gly Arg
            20                  25                  30

Thr Ala Thr Arg Gly Ile Thr Phe Phe Asp Pro Ala Pro Phe Arg Ser
        35                  40                  45

Lys Val Ala Ala Glu Ala Asp Phe Cys Gly Leu Glu Asn Gly Leu Ser

```
            50                  55                  60
Pro Gln Glu Val Arg Arg Met Asp Arg Ala Ala Gln Phe Ala Val Val
 65                  70                  75                  80

Thr Ala Arg Ala Val Glu Asp Ser Gly Ala Glu Leu Ala Ala His Pro
                 85                  90                  95

Pro His Arg Ile Gly Val Val Gly Ser Ala Val Gly Ala Thr Met
             100                 105                 110

Gly Leu Asp Asn Glu Tyr Arg Val Ser Asp Gly Arg Leu Asp
         115                 120                 125

Leu Val Asp His Arg Tyr Ala Val Pro His Leu Tyr Asn Tyr Leu Val
130                 135                 140

Pro Ser Ser Phe Ala Ala Glu Val Ala Trp Ala Val Gly Ala Glu Gly
145                 150                 155                 160

Pro Ser Thr Val Val Ser Thr Gly Cys Thr Ser Gly Ile Asp Ala Val
                 165                 170                 175

Gly Ile Ala Val Glu Leu Val Arg Glu Gly Ser Val Asp Val Met Val
                 180                 185                 190

Ala Gly Ala Val Asp Ala Pro Ile Ser Pro Ile Pro Cys Val Leu Asp
                 195                 200                 205

Ala Ile Lys Ala Thr Thr Pro Arg His Asp Ala Pro Ala Thr Ala Ser
210                 215                 220

Arg Pro Phe Asp Ser Thr Arg Asn Gly Phe Val Leu Gly Glu Gly Ala
225                 230                 235                 240

Ala Phe Phe Val Leu Glu Glu Leu His Ser Ala Arg Arg Gly Ala
                 245                 250                 255

His Ile Tyr Ala Glu Ile Ala Gly Tyr Ala Thr Arg Ser Asn Ala Tyr
                 260                 265                 270

His Met Thr Gly Leu Arg Asp Gly Ala Glu Met Ala Glu Ala Ile Arg
                 275                 280                 285

Leu Ala Leu Asp Glu Ala Arg Leu Asn Pro Glu Gln Val Asp Tyr Ile
290                 295                 300

Asn Ala His Gly Ser Gly Thr Lys Gln Asn Asp Arg His Glu Thr Ala
305                 310                 315                 320

Ala Phe Lys Lys Ala Leu Gly Glu His Ala Tyr Arg Thr Pro Val Ser
                 325                 330                 335

Ser Ile Lys Ser Met Val Gly His Ser Leu Gly Ala Ile Gly Ser Ile
                 340                 345                 350

Glu Ile Ala Ala Ser Ala Leu Ala Met Glu Tyr Asp Val Val Pro Pro
                 355                 360                 365

Thr Ala Asn Leu His Thr Pro Asp Pro Glu Cys Asp Leu Asp Tyr Val
370                 375                 380

Pro Leu Thr Ala Arg Asp Gln Arg Val Asp Ser Val Leu Thr Val Gly
385                 390                 395                 400

Ser Gly Phe Gly Phe Gln Ser Ala Met Val Leu Thr Ser Ala Gln
                 405                 410                 415

Arg Ser Thr Val
             420

<210> SEQ ID NO 15
<211> LENGTH: 422
<212> TYPE: PRT
<213> ORGANISM: Streptomyces venezuelae

<400> SEQUENCE: 15
```

-continued

```
Met Thr Ala Arg Arg Val Val Ile Thr Gly Ile Glu Val Leu Ala Pro
  1               5                  10                  15

Gly Gly Thr Gly Ser Lys Ala Phe Trp Asn Leu Leu Ser Glu Gly Arg
                 20                  25                  30

Thr Ala Thr Arg Gly Ile Thr Phe Phe Asp Pro Thr Pro Phe Arg Ser
             35                  40                  45

Arg Val Ala Ala Glu Ile Asp Phe Asp Pro Glu Ala His Gly Leu Ser
         50                  55                  60

Pro Gln Glu Ile Arg Arg Met Asp Arg Ala Ala Gln Phe Ala Val Val
 65                  70                  75                  80

Ala Ala Arg Ala Val Ala Asp Ser Gly Ile Asp Leu Ala Ala His Asp
                 85                  90                  95

Pro Tyr Arg Val Gly Val Thr Val Gly Ser Ala Val Gly Ala Thr Met
            100                 105                 110

Gly Leu Asp Glu Glu Tyr Arg Val Ser Asp Gly Arg Leu Asp
            115                 120                 125

Leu Val Asp His Ala Tyr Ala Val Pro His Leu Tyr Asp Tyr Met Val
        130                 135                 140

Pro Ser Ser Phe Ser Ala Glu Val Ala Trp Ala Val Gly Ala Glu Gly
145                 150                 155                 160

Pro Asn Thr Val Val Ser Thr Gly Cys Thr Ser Gly Leu Asp Ser Val
                165                 170                 175

Gly Tyr Ala Arg Gly Glu Leu Ile Arg Glu Gly Ser Ala Asp Val Met
            180                 185                 190

Ile Ala Gly Ser Ser Asp Ala Pro Ile Ser Pro Ile Thr Met Ala Cys
        195                 200                 205

Phe Asp Ala Ile Lys Ala Thr Thr Asn Arg Tyr Asp Asp Pro Ala His
210                 215                 220

Ala Ser Arg Pro Phe Asp Gly Thr Arg Asn Gly Phe Val Leu Gly Glu
225                 230                 235                 240

Gly Ala Ala Val Phe Val Leu Glu Glu Leu Glu Ser Ala Arg Ala Arg
                245                 250                 255

Gly Ala His Ile Tyr Ala Glu Ile Ala Gly Tyr Ala Thr Arg Ser Asn
            260                 265                 270

Ala Tyr His Met Thr Gly Leu Arg Pro Asp Gly Ala Glu Met Ala Glu
        275                 280                 285

Ala Ile Arg Val Ala Leu Asp Glu Ala Arg Met Asn Pro Thr Glu Ile
290                 295                 300

Asp Tyr Ile Asn Ala His Gly Ser Gly Thr Lys Gln Asn Asp Arg His
305                 310                 315                 320

Glu Thr Ala Ala Phe Lys Lys Ser Leu Gly Asp His Ala Tyr Arg Thr
                325                 330                 335

Pro Val Ser Ser Ile Lys Ser Met Val Gly His Ser Leu Gly Ala Ile
            340                 345                 350

Gly Ser Ile Glu Ile Ala Ala Ser Ala Leu Ala Met Glu His Asn Val
        355                 360                 365

Val Pro Pro Thr Gly Asn Leu His Thr Pro Asp Pro Glu Cys Asp Leu
370                 375                 380

Asp Tyr Val Arg Ser Cys Arg Glu Gln Leu Thr Asp Ser Val Leu Thr
385                 390                 395                 400

Val Gly Ser Gly Phe Gly Gly Phe Gln Ser Ala Met Val Leu Ala Arg
                405                 410                 415

Pro Glu Arg Lys Ile Ala
```

<210> SEQ ID NO 16
<211> LENGTH: 430
<212> TYPE: PRT
<213> ORGANISM: Streptomyces nogalater

<400> SEQUENCE: 16

```
Met Lys Glu Ser Ile Asn Arg Arg Val Val Ile Thr Gly Ile Gly Ile
  1               5                  10                  15
Val Ala Pro Asp Ala Thr Gly Val Lys Pro Phe Trp Asp Leu Leu Thr
             20                  25                  30
Ala Gly Arg Thr Ala Thr Arg Thr Ile Thr Ala Phe Asp Pro Ser Pro
         35                  40                  45
Phe Arg Ser Arg Ile Ala Ala Glu Cys Asp Phe Asp Pro Leu Ala Glu
     50                  55                  60
Gly Leu Thr Pro Gln Gln Ile Arg Arg Met Asp Arg Ala Thr Gln Phe
 65                  70                  75                  80
Ala Val Val Ser Ala Arg Glu Ser Leu Glu Asp Ser Gly Leu Asp Leu
                 85                  90                  95
Gly Ala Leu Asp Ala Ser Arg Thr Gly Val Val Gly Ser Ala Val
            100                 105                 110
Gly Cys Thr Thr Ser Leu Glu Glu Glu Tyr Ala Val Val Ser Asp Ser
        115                 120                 125
Gly Arg Asn Trp Leu Val Asp Asp Gly Tyr Ala Val Pro His Leu Phe
    130                 135                 140
Asp Tyr Phe Val Pro Ser Ser Ile Ala Ala Glu Val Ala His Asp Arg
145                 150                 155                 160
Ile Gly Ala Glu Gly Pro Val Ser Leu Val Ser Thr Gly Cys Thr Ser
                165                 170                 175
Gly Leu Asp Ala Val Gly Arg Ala Ala Asp Leu Ile Ala Glu Gly Ala
            180                 185                 190
Ala Asp Val Met Leu Ala Gly Ala Thr Glu Ala Pro Ile Ser Pro Ile
        195                 200                 205
Thr Val Ala Cys Phe Asp Ala Ile Lys Ala Thr Thr Pro Arg Asn Asp
    210                 215                 220
Thr Pro Ala Glu Ala Ser Arg Pro Phe Asp Arg Thr Arg Asn Gly Phe
225                 230                 235                 240
Val Leu Gly Glu Gly Ala Ala Val Phe Val Leu Glu Glu Phe Glu His
                245                 250                 255
Ala Arg Arg Arg Gly Ala Leu Val Tyr Ala Glu Ile Ala Gly Phe Ala
            260                 265                 270
Thr Arg Cys Asn Ala Phe His Met Thr Gly Leu Arg Pro Asp Gly Arg
        275                 280                 285
Glu Met Ala Glu Ala Ile Gly Val Ala Leu Ala Gln Ala Gly Lys Ala
    290                 295                 300
Pro Ala Asp Val Asp Tyr Val Asn Ala His Gly Ser Gly Thr Arg Gln
305                 310                 315                 320
Asn Asp Arg His Glu Thr Ala Ala Phe Lys Arg Ser Leu Gly Asp His
                325                 330                 335
Ala Tyr Arg Val Pro Val Ser Ser Ile Lys Ser Met Ile Gly His Ser
            340                 345                 350
Leu Gly Ala Ile Gly Ser Leu Glu Ile Ala Ala Ser Val Leu Ala Ile
        355                 360                 365
```

-continued

```
Thr His Asp Val Val Pro Pro Thr Ala Asn Leu His Glu Pro Asp Pro
    370                 375                 380

Glu Cys Asp Leu Asp Tyr Val Pro Leu Arg Ala Arg Ala Cys Pro Val
385                 390                 395                 400

Asp Thr Val Leu Thr Val Gly Ser Gly Phe Gly Gly Phe Gln Ser Ala
                405                 410                 415

Met Val Leu Cys Gly Pro Gly Ser Arg Gly Arg Ser Ala Ala
            420                 425                 430

<210> SEQ ID NO 17
<211> LENGTH: 426
<212> TYPE: PRT
<213> ORGANISM: Streptomyces glaucescens

<400> SEQUENCE: 17

Met Thr Arg His Ala Glu Lys Arg Val Val Ile Thr Gly Ile Gly Val
  1               5                  10                  15

Arg Ala Pro Gly Gly Ala Gly Thr Ala Ala Phe Trp Asp Leu Leu Thr
             20                  25                  30

Ala Gly Arg Thr Ala Thr Arg Thr Ile Ser Leu Phe Asp Ala Ala Pro
         35                  40                  45

Tyr Arg Ser Arg Ile Ala Gly Glu Ile Asp Phe Asp Pro Ile Gly Glu
     50                  55                  60

Gly Leu Ser Pro Arg Gln Ala Ser Thr Tyr Asp Arg Ala Thr Gln Leu
 65                  70                  75                  80

Ala Val Val Cys Ala Arg Glu Ala Leu Lys Asp Ser Gly Leu Asp Pro
                 85                  90                  95

Ala Ala Val Asn Pro Glu Arg Ile Gly Val Ser Ile Gly Thr Ala Val
            100                 105                 110

Gly Cys Thr Thr Gly Leu Asp Arg Glu Tyr Ala Arg Val Ser Glu Gly
        115                 120                 125

Gly Ser Arg Trp Leu Val Asp His Thr Leu Ala Val Glu Gln Leu Phe
    130                 135                 140

Asp Tyr Phe Val Pro Thr Ser Ile Cys Arg Glu Val Ala Trp Glu Ala
145                 150                 155                 160

Gly Ala Glu Gly Pro Val Thr Val Val Ser Thr Gly Cys Thr Ser Gly
                165                 170                 175

Leu Asp Ala Val Gly Tyr Gly Thr Glu Leu Ile Arg Asp Gly Arg Ala
            180                 185                 190

Asp Val Val Val Cys Gly Ala Thr Asp Ala Pro Ile Ser Pro Ile Thr
        195                 200                 205

Val Ala Cys Phe Asp Ala Ile Lys Ala Thr Ser Ala Asn Asn Asp Asp
    210                 215                 220

Pro Ala His Ala Ser Arg Pro Phe Asp Arg Asn Arg Asp Gly Phe Val
225                 230                 235                 240

Leu Gly Glu Gly Ser Ala Val Phe Val Leu Glu Glu Leu Ser Ala Ala
                245                 250                 255

Arg Arg Arg Gly Ala His Ala Tyr Ala Glu Val Arg Gly Phe Ala Thr
            260                 265                 270

Arg Ser Asn Ala Phe His Met Thr Gly Leu Lys Pro Asp Gly Arg Glu
        275                 280                 285

Met Ala Glu Ala Ile Thr Ala Ala Leu Asp Gln Ala Arg Arg Thr Gly
    290                 295                 300

Asp Asp Leu His Tyr Ile Asn Ala His Gly Ser Gly Thr Arg Gln Asn
305                 310                 315                 320
```

-continued

```
Asp Arg His Glu Thr Ala Ala Phe Lys Arg Ser Leu Gly Gln Arg Ala
            325                 330                 335

Tyr Asp Val Pro Val Ser Ser Ile Lys Ser Met Ile Gly His Ser Leu
            340                 345                 350

Gly Ala Ile Gly Ser Leu Glu Leu Ala Ala Cys Ala Leu Ala Ile Glu
            355                 360                 365

His Gly Val Ile Pro Pro Thr Ala Asn Tyr Glu Glu Pro Asp Pro Glu
        370                 375                 380

Cys Asp Leu Asp Tyr Val Pro Asn Val Ala Arg Glu Gln Arg Val Asp
385                 390                 395                 400

Thr Val Leu Ser Val Gly Ser Phe Gly Gly Phe Gln Ser Ala Ala
                405                 410                 415

Val Leu Ala Arg Pro Lys Glu Thr Arg Ser
            420                 425

<210> SEQ ID NO 18
<211> LENGTH: 418
<212> TYPE: PRT
<213> ORGANISM: Streptomyces sp. C5

<400> SEQUENCE: 18

Met Asn Arg Arg Val Val Ile Thr Gly Met Gly Val Val Ala Pro Gly
1               5                   10                  15

Ala Ile Gly Ile Lys Ser Phe Trp Glu Leu Leu Ser Gly Thr Thr
            20                  25                  30

Ala Thr Arg Ala Ile Thr Thr Phe Asp Ala Thr Pro Phe Arg Ser Arg
        35                  40                  45

Ile Ala Ala Glu Cys Asp Phe Asp Pro Val Ala Ala Gly Leu Ser Ala
    50                  55                  60

Glu Gln Ala Arg Arg Leu Asp Arg Ala Gly Gln Phe Ala Leu Val Ala
65                  70                  75                  80

Gly Gln Glu Ala Leu Thr Asp Ser Gly Leu Arg Ile Gly Glu Asp Ser
                85                  90                  95

Ala His Arg Val Gly Val Cys Val Gly Thr Ala Val Gly Cys Thr Gln
            100                 105                 110

Lys Leu Glu Ser Glu Tyr Val Ala Leu Ser Ala Gly Gly Ala Asn Trp
        115                 120                 125

Val Val Asp Pro His Arg Gly Ala Pro Glu Leu Tyr Asp Tyr Phe Val
    130                 135                 140

Pro Ser Ser Leu Ala Ala Glu Val Ala Trp Leu Ala Gly Ala Glu Gly
145                 150                 155                 160

Pro Val Asn Ile Val Ser Ala Gly Cys Thr Ser Gly Ile Asp Ser Ile
                165                 170                 175

Gly Tyr Ala Cys Glu Leu Ile Arg Glu Gly Thr Val Asp Val Met Leu
            180                 185                 190

Ala Gly Gly Val Asp Ala Pro Ile Ala Pro Ile Thr Val Ala Cys Phe
        195                 200                 205

Asp Ala Ile Arg Val Thr Ser Asp His Asn Asp Thr Pro Glu Thr Leu
    210                 215                 220

Ala Pro Phe Ser Arg Ser Arg Asn Gly Phe Val Leu Gly Glu Gly Gly
225                 230                 235                 240

Ala Ile Val Val Leu Glu Glu Ala Glu Ala Val Arg Arg Gly Ala
                245                 250                 255

Arg Ile Tyr Ala Glu Ile Gly Gly Tyr Ala Ser Arg Gly Asn Ala Tyr
```

-continued

```
                260                 265                 270
His Met Thr Gly Leu Arg Ala Asp Gly Ala Glu Met Ala Ala Ile
            275                 280                 285

Thr Ala Ala Leu Asp Glu Ala Arg Arg Asp Pro Ser Asp Val Asp Tyr
            290                 295                 300

Val Asn Ala His Gly Thr Ala Thr Arg Gln Asn Asp Arg His Glu Thr
305                 310                 315                 320

Ser Ala Phe Lys Arg Ser Leu Gly Asp His Ala Tyr Arg Val Pro Ile
                325                 330                 335

Ser Ser Val Lys Ser Met Ile Gly His Ser Leu Gly Ala Ala Gly Ser
                340                 345                 350

Leu Glu Val Ala Ala Thr Ala Leu Ala Val Glu Tyr Gly Ala Ile Pro
                355                 360                 365

Pro Thr Ala Asn Leu His Asp Pro Asp Pro Glu Leu Asp Leu Asp Tyr
                370                 375                 380

Val Pro Leu Thr Ala Arg Glu Lys Arg Val Arg His Ala Leu Thr Val
385                 390                 395                 400

Gly Ser Gly Phe Gly Gly Phe Gln Ser Ala Met Leu Leu Ser Arg Pro
                405                 410                 415

Glu Arg

<210> SEQ ID NO 19
<211> LENGTH: 419
<212> TYPE: PRT
<213> ORGANISM: Streptomyces peucetius

<400> SEQUENCE: 19

Met Asn Arg Arg Ile Val Ile Thr Gly Ile Gly Val Val Ala Pro Gly
1               5                   10                  15

Ala Val Gly Thr Lys Pro Phe Trp Glu Leu Leu Ser Gly Thr Thr
            20                  25                  30

Ala Thr Arg Ala Ile Ser Thr Phe Asp Ala Thr Pro Phe Arg Ser Arg
            35                  40                  45

Ile Ala Ala Glu Cys Asp Phe Asp Pro Val Ala Ala Gly Leu Ser Ala
            50                  55                  60

Glu Gln Ala Arg Arg Leu Asp Arg Ala Gly Gln Phe Ala Leu Val Ala
65                  70                  75                  80

Gly Gln Glu Ala Leu Ala Asp Ser Gly Leu Arg Ile Asp Glu Asp Ser
                85                  90                  95

Ala His Arg Val Gly Val Cys Val Gly Thr Ala Val Gly Cys Thr Gln
                100                 105                 110

Lys Leu Glu Ser Glu Tyr Val Ala Leu Ser Ala Gly Gly Ala His Trp
                115                 120                 125

Val Val Asp Pro Gly Arg Gly Ser Pro Glu Leu Tyr Asp Tyr Phe Val
                130                 135                 140

Pro Ser Ser Leu Ala Ala Glu Val Ala Trp Leu Ala Gly Ala Glu Gly
145                 150                 155                 160

Pro Val Asn Ile Val Ser Ala Gly Cys Thr Ser Gly Ile Asp Ser Ile
                165                 170                 175

Gly Tyr Ala Cys Glu Leu Ile Arg Glu Gly Thr Val Asp Ala Met Val
                180                 185                 190

Ala Gly Gly Val Asp Ala Pro Ile Ala Pro Ile Thr Val Ala Cys Phe
                195                 200                 205

Asp Ala Ile Arg Ala Thr Ser Asp His Asn Asp Thr Pro Glu Thr Ala
```

-continued

```
            210                 215                 220
Ser Arg Pro Phe Ser Arg Ser Arg Asn Gly Phe Val Leu Gly Glu Gly
225                 230                 235                 240

Gly Ala Ile Val Val Leu Glu Glu Ala Glu Ala Ala Val Arg Arg Gly
                245                 250                 255

Ala Arg Ile Tyr Ala Glu Ile Gly Gly Tyr Ala Ser Arg Gly Asn Ala
                260                 265                 270

Tyr His Met Thr Gly Leu Arg Ala Asp Gly Ala Glu Met Ala Ala Ala
            275                 280                 285

Ile Thr Ala Ala Leu Asp Glu Ala Arg Arg Asp Pro Ser Asp Val Asp
290                 295                 300

Tyr Val Asn Ala His Gly Thr Ala Thr Lys Gln Asn Asp Arg His Glu
305                 310                 315                 320

Thr Ser Ala Phe Lys Arg Ser Leu Gly Glu His Ala Tyr Arg Val Pro
                325                 330                 335

Ile Ser Ser Ile Lys Ser Met Ile Gly His Ser Leu Gly Ala Val Gly
                340                 345                 350

Ser Leu Glu Val Ala Ala Thr Ala Leu Ala Val Glu Tyr Gly Val Ile
                355                 360                 365

Pro Pro Thr Ala Asn Leu His Asp Pro Asp Pro Glu Leu Asp Leu Asp
370                 375                 380

Tyr Val Pro Leu Thr Ala Arg Glu Lys Arg Val Arg His Ala Leu Thr
385                 390                 395                 400

Val Gly Ser Gly Phe Gly Gly Phe Gln Ser Ala Met Leu Leu Ser Arg
                405                 410                 415

Leu Glu Arg

<210> SEQ ID NO 20
<211> LENGTH: 423
<212> TYPE: PRT
<213> ORGANISM: Streptomyces coelicolor

<400> SEQUENCE: 20

Met Thr Arg Arg Arg Val Ala Val Thr Gly Ile Gly Val Val Ala Pro
1               5                   10                  15

Gly Gly Ile Gly Thr Pro Gln Phe Trp Arg Leu Leu Ser Glu Gly Arg
                20                  25                  30

Thr Ala Thr Arg Arg Ile Ser Leu Phe Asp Pro Ser Gly Leu Arg Ser
            35                  40                  45

Gln Ile Ala Ala Glu Cys Asp Phe Glu Pro Ser Asp His Gly Leu Gly
    50                  55                  60

Leu Ala Thr Ala Gln Arg Cys Asp Arg Tyr Val Gln Phe Ala Leu Val
65                  70                  75                  80

Ala Ala Ser Glu Ala Val Arg Asp Ala Asn Leu Asp Met Asn Arg Glu
                85                  90                  95

Asp Pro Trp Arg Ala Gly Ala Thr Leu Gly Thr Ala Val Gly Gly Thr
                100                 105                 110

Thr Arg Leu Glu His Asp Tyr Val Leu Val Ser Glu Arg Gly Ser Arg
            115                 120                 125

Trp Asp Val Asp Asp Arg Arg Ser Glu Pro His Leu Glu Arg Ala Phe
    130                 135                 140

Thr Pro Ala Thr Leu Ser Ser Ala Val Ala Glu Glu Phe Gly Val Arg
145                 150                 155                 160

Gly Pro Val Gln Thr Val Ser Thr Gly Cys Thr Ser Gly Leu Asp Ala
```

-continued

```
                    165                 170                 175
Val Gly Tyr Ala Tyr His Ala Val Ala Glu Gly Arg Val Asp Val Cys
            180                 185                 190
Leu Ala Gly Ala Ala Asp Ser Pro Ile Ser Pro Ile Thr Met Ala Cys
            195                 200                 205
Phe Asp Ala Ile Lys Ala Thr Ser Pro Asn Asn Asp Asp Pro Ala His
    210                 215                 220
Ala Ser Arg Pro Phe Asp Ala Asp Arg Asn Gly Phe Val Met Gly Glu
225                 230                 235                 240
Gly Ala Ala Val Leu Val Leu Glu Asp Leu Glu His Ala Arg Ala Arg
                245                 250                 255
Gly Ala Asp Val Tyr Cys Glu Val Ser Gly Tyr Ala Thr Phe Gly Asn
            260                 265                 270
Ala Tyr His Met Thr Gly Leu Thr Lys Glu Gly Leu Glu Met Ala Arg
    275                 280                 285
Ala Ile Asp Thr Ala Leu Asp Met Ala Glu Leu Asp Gly Ser Ala Ile
    290                 295                 300
Asp Tyr Val Asn Ala His Gly Ser Gly Thr Gln Gln Asn Asp Arg His
305                 310                 315                 320
Glu Thr Ala Ala Val Lys Arg Ser Leu Gly Glu His Ala Tyr Ala Thr
                325                 330                 335
Pro Met Ser Ser Ile Lys Ser Met Val Gly His Ser Leu Gly Ala Ile
            340                 345                 350
Gly Ser Ile Glu Leu Ala Ala Cys Val Leu Ala Met Ala His Gln Val
            355                 360                 365
Val Pro Pro Thr Ala Asn Tyr Thr Thr Pro Asp Pro Glu Cys Asp Leu
    370                 375                 380
Asp Tyr Val Pro Arg Glu Ala Arg Glu Arg Thr Leu Arg His Val Leu
385                 390                 395                 400
Ser Val Gly Ser Gly Phe Gly Phe Gln Ser Ala Val Val Leu Ser
                405                 410                 415
Gly Ser Glu Gly Gly Leu Arg
            420

<210> SEQ ID NO 21
<211> LENGTH: 871
<212> TYPE: PRT
<213> ORGANISM: Streptomyces caelestis

<400> SEQUENCE: 21

Met Ala Gly His Gly Asp Ala Thr Ala Gln Lys Ala Gln Asp Ala Glu
1               5                   10                  15
Lys Ser Glu Asp Gly Ser Asp Ala Ile Ala Val Ile Gly Met Ser Cys
                20                  25                  30
Arg Phe Pro Gly Ala Pro Gly Thr Ala Glu Phe Trp Gln Leu Leu Ser
            35                  40                  45
Ser Gly Ala Asp Ala Val Val Thr Ala Ala Asp Gly Arg Arg Arg Gly
    50                  55                  60
Thr Ile Asp Ala Pro Ala Asp Phe Asp Ala Ala Phe Phe Gly Met Ser
65                  70                  75                  80
Pro Arg Glu Ala Ala Ala Thr Asp Pro Gln Gln Arg Leu Val Leu Glu
                85                  90                  95
Leu Gly Trp Glu Ala Leu Glu Asp Ala Gly Ile Val Pro Glu Ser Leu
            100                 105                 110
```

-continued

```
Arg Gly Glu Ala Ala Ser Val Phe Val Gly Ala Met Asn Asp Asp Tyr
        115                 120                 125
Ala Thr Leu Leu His Arg Ala Gly Ala Pro Thr Asp Thr Tyr Thr Ala
    130                 135                 140
Thr Gly Leu Gln His Ser Met Ile Ala Asn Arg Leu Ser Tyr Phe Leu
145                 150                 155                 160
Gly Leu Arg Gly Pro Ser Leu Val Val Asp Thr Gly Gln Ser Ser Ser
                165                 170                 175
Leu Val Ala Val Ala Leu Ala Val Glu Ser Leu Arg Gly Gly Thr Ser
            180                 185                 190
Gly Ile Ala Leu Ala Gly Gly Val Asn Leu Val Leu Ala Glu Glu Gly
        195                 200                 205
Ser Ala Ala Met Glu Arg Val Gly Ala Leu Ser Pro Asp Gly Arg Cys
    210                 215                 220
His Thr Phe Asp Ala Arg Ala Asn Gly Tyr Val Arg Gly Glu Gly Gly
225                 230                 235                 240
Ala Ile Val Val Leu Lys Pro Leu Ala Asp Ala Leu Ala Asp Gly Asp
                245                 250                 255
Arg Val Tyr Cys Val Val Arg Gly Val Ala Thr Gly Asn Asp Gly Gly
            260                 265                 270
Gly Pro Gly Leu Thr Val Pro Asp Arg Ala Gly Gln Glu Ala Val Leu
        275                 280                 285
Arg Ala Ala Cys Asp Gln Ala Gly Val Arg Pro Ala Asp Val Arg Phe
    290                 295                 300
Val Glu Leu His Gly Thr Gly Thr Pro Ala Gly Asp Pro Val Glu Ala
305                 310                 315                 320
Glu Ala Leu Gly Ala Val Tyr Gly Thr Gly Arg Pro Ala Asn Glu Pro
                325                 330                 335
Leu Leu Val Gly Ser Val Lys Thr Asn Ile Gly His Leu Glu Gly Ala
            340                 345                 350
Ala Gly Ile Ala Gly Phe Val Lys Ala Ala Leu Cys Leu His Glu Arg
        355                 360                 365
Ala Leu Pro Ala Ser Leu Asn Phe Glu Thr Pro Asn Pro Ala Ile Pro
    370                 375                 380
Leu Glu Arg Leu Arg Leu Lys Val Gln Thr Ala His Ala Ala Leu Gln
385                 390                 395                 400
Pro Gly Thr Gly Gly Pro Leu Leu Ala Gly Val Ser Ala Phe Gly
                405                 410                 415
Met Gly Gly Thr Asn Cys His Val Val Leu Glu Glu Thr Pro Gly Gly
            420                 425                 430
Arg Gln Pro Ala Glu Thr Gly Gln Ala Asp Ala Cys Leu Phe Ser Ala
        435                 440                 445
Ser Pro Met Leu Leu Leu Ser Ala Arg Ser Glu Gln Ala Leu Arg Ala
    450                 455                 460
Gln Ala Ala Arg Leu Arg Glu His Leu Glu Asp Ser Gly Ala Asp Pro
465                 470                 475                 480
Leu Asp Ile Ala Tyr Ser Leu Ala Thr Thr Arg Thr Arg Phe Glu His
                485                 490                 495
Arg Ala Ala Val Pro Cys Gly Asp Pro Asp Arg Leu Ser Ser Ala Leu
            500                 505                 510
Ala Ala Leu Ala Ala Gly Gln Thr Pro Arg Gly Val Arg Ile Gly Ser
        515                 520                 525
Thr Asp Ala Asp Gly Arg Leu Ala Leu Leu Phe Thr Gly Gln Gly Ala
```

```
                    530                 535                 540
Gln His Pro Gly Met Gly Gln Glu Leu Tyr Thr Thr Asp Pro His Phe
545                 550                 555                 560

Ala Ala Ala Leu Asp Glu Val Cys Glu Leu Gln Arg Cys Gly Thr
                565                 570                 575

Gln Asn Leu Arg Glu Val Met Phe Thr Pro Asp Gln Pro Asp Leu Leu
                580                 585                 590

Asp Arg Thr Glu Tyr Thr Gln Pro Ala Leu Phe Ala Leu Gln Thr Ala
                595                 600                 605

Leu Tyr Arg Thr Leu Thr Ala Arg Gly Thr Gln Ala His Leu Val Leu
610                 615                 620

Gly His Ser Val Gly Glu Ile Thr Ala Ala His Ile Ala Gly Val Leu
625                 630                 635                 640

Asp Leu Pro Asp Ala Ala Arg Leu Ile Thr Ala Arg Ala His Val Met
                645                 650                 655

Gly Gln Leu Pro His Gly Gly Ala Met Leu Ser Val Gln Ala Ala Glu
                660                 665                 670

His Asp Leu Asp Gln Leu Ala His Thr His Gly Val Glu Ile Ala Ala
                675                 680                 685

Val Asn Gly Pro Thr His Cys Val Leu Ser Gly Pro Arg Thr Ala Leu
                690                 695                 700

Glu Glu Thr Ala Gln His Leu Arg Glu Gln Asn Val Arg His Thr Trp
705                 710                 715                 720

Leu Lys Val Ser His Ala Phe His Ser Ala Leu Met Asp Pro Met Leu
                725                 730                 735

Gly Ala Phe Arg Asp Thr Leu Asn Thr Leu Asn Tyr Gln Pro Pro Thr
                740                 745                 750

Ile Pro Leu Ile Ser Asn Leu Thr Gly Gln Ile Ala Asp Pro Asn His
                755                 760                 765

Leu Cys Thr Pro Asp Tyr Trp Ile Asp His Ala Arg His Thr Val Arg
                770                 775                 780

Phe Ala Asp Ala Val Gln Thr Ala His His Gln Gly Thr Thr Thr Tyr
785                 790                 795                 800

Leu Glu Ile Gly Pro His Pro Thr Leu Thr Thr Leu Leu His His Thr
                805                 810                 815

Leu Asp Asn Pro Thr Thr Ile Pro Thr Leu His Arg Glu Arg Pro Glu
                820                 825                 830

Pro Glu Thr Leu Thr Gln Ala Ile Ala Ala Val Gly Val Arg Thr Asp
                835                 840                 845

Gly Ile Asp Trp Ala Val Leu Cys Gly Ala Ser Arg Pro Arg Arg Val
850                 855                 860

Glu Leu Pro Thr Tyr Ala Phe
865                 870

<210> SEQ ID NO 22
<211> LENGTH: 890
<212> TYPE: PRT
<213> ORGANISM: Streptomyces ambofaciens

<400> SEQUENCE: 22

Met Ser Gly Glu Leu Ala Ile Ser Arg Ser Asp Arg Ser Asp Ala
 1               5                  10                  15

Val Ala Val Val Gly Met Ala Cys Arg Phe Pro Gly Ala Pro Gly Ile
                20                  25                  30
```

-continued

```
Ala Glu Phe Trp Lys Leu Leu Thr Asp Gly Arg Asp Ala Ile Gly Arg
         35                  40                  45

Asp Ala Asp Gly Arg Arg Gly Met Ile Glu Ala Pro Gly Asp Phe
 50                  55                  60

Asp Ala Ala Phe Phe Gly Met Ser Pro Arg Glu Ala Glu Thr Asp
 65                  70                  75                  80

Pro Gln Gln Arg Leu Met Leu Glu Leu Gly Trp Glu Ala Leu Glu Asp
                 85                  90                  95

Ala Gly Ile Val Pro Gly Ser Leu Arg Gly Glu Ala Val Gly Val Phe
             100                 105                 110

Val Gly Ala Met His Asp Asp Tyr Ala Thr Leu Leu His Arg Ala Gly
             115                 120                 125

Ala Pro Val Gly Pro His Thr Ala Thr Gly Leu Gln Arg Ala Met Leu
 130                 135                 140

Ala Asn Arg Leu Ser Tyr Val Leu Gly Thr Arg Gly Pro Ser Leu Ala
145                 150                 155                 160

Val Asp Thr Ala Gln Ser Ser Leu Val Ala Val Ala Leu Ala Val
             165                 170                 175

Glu Ser Leu Arg Ala Gly Thr Ser Arg Val Ala Val Ala Gly Gly Val
             180                 185                 190

Asn Leu Val Leu Ala Asp Glu Gly Thr Ala Ala Met Glu Arg Leu Gly
             195                 200                 205

Ala Leu Ser Pro Asp Gly Arg Cys His Thr Phe Asp Ala Arg Ala Asn
             210                 215                 220

Gly Tyr Val Arg Gly Glu Gly Gly Ala Ala Val Val Leu Lys Pro Leu
225                 230                 235                 240

Ala Asp Ala Leu Ala Asp Gly Asp Pro Val Tyr Cys Val Val Arg Gly
             245                 250                 255

Val Ala Val Gly Asn Asp Gly Gly Pro Gly Leu Thr Ala Pro Asp
             260                 265                 270

Arg Glu Gly Gln Glu Ala Val Leu Arg Ala Ala Cys Ala Gln Ala Arg
             275                 280                 285

Val Asp Pro Ala Glu Val Arg Phe Val Glu Leu His Gly Thr Gly Thr
 290                 295                 300

Pro Val Gly Asp Pro Val Glu Ala His Ala Leu Gly Ala Val His Gly
305                 310                 315                 320

Ser Gly Arg Pro Ala Asp Asp Pro Leu Leu Val Gly Ser Val Lys Thr
             325                 330                 335

Asn Ile Gly His Leu Glu Gly Ala Ala Gly Ile Ala Gly Leu Val Lys
             340                 345                 350

Ala Ala Leu Cys Leu Arg Glu Arg Thr Leu Pro Gly Ser Leu Asn Phe
             355                 360                 365

Ala Thr Pro Ser Pro Ala Ile Pro Leu Asp Gln Leu Arg Leu Lys Val
 370                 375                 380

Gln Thr Ala Ala Ala Glu Leu Pro Leu Ala Pro Gly Ala Pro Leu
385                 390                 395                 400

Leu Ala Gly Val Ser Ser Phe Gly Ile Gly Gly Thr Asn Cys His Val
             405                 410                 415

Val Leu Glu His Leu Pro Ser Arg Pro Thr Pro Ala Val Ser Val Ala
             420                 425                 430

Ala Ser Leu Pro Asp Val Pro Pro Leu Leu Ser Ala Arg Ser Glu
             435                 440                 445

Gly Ala Leu Arg Ala Gln Ala Val Arg Leu Gly Glu Thr Val Glu Arg
```

-continued

```
            450                 455                 460
Val Gly Ala Asp Pro Arg Asp Val Ala Tyr Ser Leu Ala Ser Thr Arg
465                 470                 475                 480

Thr Leu Phe Glu His Arg Ala Val Val Pro Cys Gly Arg Gly Gly Glu
                485                 490                 495

Leu Val Ala Ala Leu Gly Gly Phe Ala Ala Gly Arg Val Ser Gly Gly
            500                 505                 510

Val Arg Ser Gly Arg Ala Val Pro Gly Val Gly Val Leu Phe Thr
            515                 520                 525

Gly Gln Gly Ala Gln Trp Val Gly Met Gly Arg Gly Leu Tyr Ala Gly
530                 535                 540

Gly Gly Val Phe Ala Glu Val Leu Asp Glu Val Leu Ser Met Val Gly
545                 550                 555                 560

Glu Val Asp Gly Arg Ser Leu Arg Asp Val Met Phe Gly Asp Val Asp
                565                 570                 575

Val Asp Ala Gly Ala Gly Ala Asp Ala Gly Ala Gly Ala Gly
            580                 585                 590

Val Gly Ser Gly Ser Gly Ser Val Gly Gly Leu Leu Gly Arg Thr Glu
            595                 600                 605

Phe Ala Gln Pro Ala Leu Phe Ala Leu Glu Val Ala Leu Phe Arg Ala
            610                 615                 620

Leu Glu Ala Arg Gly Val Glu Val Ser Val Val Leu Gly His Ser Val
625                 630                 635                 640

Gly Glu Val Ala Ala Ala Thr Val Ala Gly Val Leu Ser Leu Gly Asp
                645                 650                 655

Ala Val Arg Leu Val Val Ala Arg Gly Gly Leu Met Gly Gly Leu Pro
            660                 665                 670

Val Gly Gly Gly Met Trp Ser Val Gly Ala Ser Glu Ser Val Val Arg
            675                 680                 685

Gly Val Val Glu Gly Leu Gly Glu Trp Val Ser Val Ala Ala Val Asn
            690                 695                 700

Gly Pro Arg Ser Val Val Leu Ser Gly Asp Val Gly Val Leu Glu Ser
705                 710                 715                 720

Val Val Ala Ser Leu Met Gly Asp Gly Val Glu Tyr Arg Arg Leu Asp
                725                 730                 735

Val Ser His Gly Phe His Ser Val Leu Met Glu Pro Val Leu Gly Glu
            740                 745                 750

Phe Arg Gly Val Val Glu Ser Leu Glu Phe Gly Arg Val Arg Pro Gly
            755                 760                 765

Val Val Val Ser Gly Val Ser Gly Val Gly Ser Gly Glu
            770                 775                 780

Leu Gly Asp Pro Gly Tyr Trp Val Arg His Ala Arg Glu Ala Val Arg
785                 790                 795                 800

Phe Ala Asp Gly Val Gly Val Val Arg Gly Leu Gly Val Gly Thr Leu
                805                 810                 815

Val Glu Val Gly Pro His Gly Val Leu Thr Gly Met Ala Gly Glu Cys
            820                 825                 830

Leu Gly Ala Gly Asp Asp Val Val Val Pro Ala Met Arg Arg Gly
            835                 840                 845

Arg Ala Glu Arg Glu Val Phe Glu Ala Ala Leu Ala Thr Val Phe Thr
            850                 855                 860

Arg Asp Ala Gly Leu Asp Ala Thr Ala Leu His Thr Gly Ser Thr Gly
865                 870                 875                 880
```

```
Arg Arg Ile Asp Leu Pro Thr Thr Pro Phe
            885                 890

<210> SEQ ID NO 23
<211> LENGTH: 920
<212> TYPE: PRT
<213> ORGANISM: Streptomyces cinnamonensis

<400> SEQUENCE: 23

Met Ala Ala Ser Ala Ser Ala Ser Pro Ser Gly Pro Ser Ala Gly Pro
  1               5                  10                  15

Asp Pro Ile Ala Val Val Gly Met Ala Cys Arg Leu Pro Gly Ala Pro
             20                  25                  30

Asp Pro Asp Ala Phe Trp Arg Leu Leu Ser Glu Gly Arg Ser Ala Val
         35                  40                  45

Ser Thr Ala Pro Pro Glu Arg Arg Ala Asp Ser Gly Leu His Gly
     50                  55                  60

Pro Gly Gly Tyr Leu Asp Arg Ile Asp Gly Phe Asp Ala Asp Phe Phe
 65                  70                  75                  80

His Ile Ser Pro Arg Glu Ala Val Ala Met Asp Pro Gln Gln Arg Leu
                 85                  90                  95

Leu Leu Glu Leu Ser Trp Glu Ala Leu Glu Asp Ala Gly Ile Arg Pro
            100                 105                 110

Pro Thr Leu Ala Arg Ser Arg Thr Gly Val Phe Val Gly Ala Phe Trp
        115                 120                 125

Asp Asp Tyr Thr Asp Val Leu Asn Leu Arg Ala Pro Gly Ala Val Thr
    130                 135                 140

Arg His Thr Met Thr Gly Val His Arg Ser Ile Leu Ala Asn Arg Ile
145                 150                 155                 160

Ser Tyr Ala Tyr His Leu Ala Gly Pro Ser Leu Thr Val Asp Thr Ala
                165                 170                 175

Gln Ser Ser Ser Leu Val Ala Val His Leu Ala Cys Glu Ser Ile Arg
            180                 185                 190

Ser Gly Asp Ser Asp Ile Ala Phe Ala Gly Gly Val Asn Leu Ile Cys
        195                 200                 205

Ser Pro Arg Thr Thr Glu Leu Ala Ala Ala Arg Phe Gly Gly Leu Ser
    210                 215                 220

Ala Ala Gly Arg Cys His Thr Phe Asp Ala Arg Ala Asp Gly Phe Val
225                 230                 235                 240

Arg Gly Glu Gly Gly Gly Leu Val Val Leu Lys Pro Leu Ala Ala Ala
                245                 250                 255

Arg Arg Asp Gly Asp Thr Val Tyr Cys Val Ile Arg Gly Ser Ala Val
            260                 265                 270

Asn Ser Asp Gly Thr Thr Asp Gly Ile Thr Leu Pro Ser Gly Gln Ala
        275                 280                 285

Gln Gln Asp Val Val Arg Leu Ala Cys Arg Arg Ala Arg Ile Thr Pro
    290                 295                 300

Asp Gln Val Gln Tyr Val Glu Leu His Gly Thr Gly Thr Pro Val Gly
305                 310                 315                 320

Asp Pro Ile Glu Ala Ala Ala Leu Gly Ala Ala Leu Gly Gln Asp Ala
                325                 330                 335

Ala Arg Ala Val Pro Leu Ala Val Gly Ser Ala Lys Thr Asn Val Gly
            340                 345                 350

His Leu Glu Ala Ala Ala Gly Ile Val Gly Leu Leu Lys Thr Ala Leu
```

-continued

```
            355                 360                 365
Ser Ile His His Arg Arg Leu Ala Pro Ser Leu Asn Phe Thr Thr Pro
    370                 375                 380
Asn Pro Ala Ile Pro Leu Ala Asp Leu Gly Leu Thr Val Gln Gln Asp
385                 390                 395                 400
Leu Ala Asp Trp Pro Arg Pro Glu Gln Pro Leu Ile Ala Gly Val Ser
                405                 410                 415
Ser Phe Gly Met Gly Gly Thr Asn Gly His Val Val Ala Ala Ala
                420              425                 430
Pro Asp Ser Val Ala Val Pro Glu Pro Val Gly Val Pro Glu Arg Val
            435                 440                 445
Glu Val Pro Glu Pro Val Val Ser Glu Pro Val Val Pro Thr
450                 455                 460
Pro Trp Pro Val Ser Ala His Ser Ala Ser Ala Leu Arg Ala Gln Ala
465                 470                 475                 480
Gly Arg Leu Arg Thr His Leu Ala Ala His Arg Pro Thr Pro Asp Ala
                485                 490                 495
Ala Arg Val Gly His Ala Leu Ala Thr Thr Arg Ala Pro Leu Ala His
            500                 505                 510
Arg Ala Val Leu Leu Gly Gly Asp Thr Ala Glu Leu Leu Gly Ser Leu
            515                 520                 525
Asp Ala Leu Ala Glu Gly Ala Glu Thr Ala Ser Ile Val Arg Gly Glu
            530                 535                 540
Ala Tyr Thr Glu Gly Arg Thr Ala Phe Leu Phe Ser Gly Gln Gly Ala
545                 550                 555                 560
Gln Arg Leu Gly Met Gly Arg Glu Leu Tyr Ala Val Phe Pro Val Phe
                565                 570                 575
Ala Asp Ala Leu Asp Glu Ala Phe Ala Ala Leu Asp Val His Leu Asp
                580                 585                 590
Arg Pro Leu Arg Glu Ile Val Leu Gly Glu Thr Asp Ser Gly Gly Asn
            595                 600                 605
Val Ser Gly Glu Asn Val Ile Gly Glu Gly Ala Asp His Gln Ala Leu
            610                 615                 620
Leu Asp Gln Thr Ala Tyr Thr Gln Pro Ala Leu Phe Ala Ile Glu Thr
625                 630                 635                 640
Ser Leu Tyr Arg Leu Ala Ala Ser Phe Gly Leu Lys Pro Asp Tyr Val
                645                 650                 655
Leu Gly His Ser Val Gly Glu Ile Ala Ala Ala His Val Ala Gly Val
                660                 665                 670
Leu Ser Leu Pro Asp Ala Ser Ala Leu Val Ala Thr Arg Gly Arg Leu
                675                 680                 685
Met Gln Ala Val Arg Ala Pro Gly Ala Met Ala Ala Trp Gln Ala Thr
            690                 695                 700
Ala Asp Glu Ala Ala Glu Gln Leu Ala Gly His Glu Arg His Val Thr
705                 710                 715                 720
Val Ala Ala Val Asn Gly Pro Asp Ser Val Val Ser Gly Asp Arg
                725                 730                 735
Ala Thr Val Asp Glu Leu Thr Ala Ala Trp Arg Gly Arg Gly Arg Lys
                740                 745                 750
Ala His His Leu Lys Val Ser His Ala Phe His Ser Pro His Met Asp
            755                 760                 765
Pro Ile Leu Asp Glu Leu Arg Ala Val Ala Ala Gly Leu Thr Phe His
770                 775                 780
```

```
Glu Pro Val Ile Pro Val Val Ser Asn Val Thr Gly Glu Leu Val Thr
785                 790                 795                 800

Ala Thr Ala Thr Gly Ser Gly Ala Gly Gln Ala Asp Pro Glu Tyr Trp
            805                 810                 815

Ala Arg His Ala Arg Glu Pro Val Arg Phe Leu Ser Gly Val Arg Gly
        820                 825                 830

Leu Cys Glu Arg Gly Val Thr Thr Phe Val Glu Leu Gly Pro Asp Ala
    835                 840                 845

Pro Leu Ser Ala Met Ala Arg Asp Cys Phe Pro Ala Pro Ala Asp Arg
850                 855                 860

Ser Arg Pro Arg Pro Ala Ala Ile Ala Thr Cys Arg Arg Gly Arg Asp
865                 870                 875                 880

Glu Val Ala Thr Phe Leu Arg Ser Leu Ala Gln Ala Tyr Val Arg Gly
                885                 890                 895

Ala Asp Val Asp Phe Thr Arg Ala Tyr Gly Ala Thr Ala Thr Arg Arg
            900                 905                 910

Phe Pro Leu Pro Thr Tyr Pro Phe
            915                 920

<210> SEQ ID NO 24
<211> LENGTH: 928
<212> TYPE: PRT
<213> ORGANISM: Streptomyces antibioticus

<400> SEQUENCE: 24

Met His Val Pro Gly Glu Glu Asn Gly His Ser Ile Ala Ile Val Gly
  1               5                  10                  15

Ile Ala Cys Arg Leu Pro Gly Ser Ala Thr Pro Gln Glu Phe Trp Arg
             20                  25                  30

Leu Leu Ala Asp Ser Ala Asp Ala Leu Asp Glu Pro Pro Ala Gly Arg
         35                  40                  45

Phe Pro Thr Gly Ser Leu Ser Ser Pro Pro Ala Pro Arg Gly Gly Phe
     50                  55                  60

Leu Asp Ser Ile Asp Thr Phe Asp Ala Asp Phe Phe Asn Ile Ser Pro
 65                  70                  75                  80

Arg Glu Ala Gly Val Leu Asp Pro Gln Gln Arg Leu Ala Leu Glu Leu
                 85                  90                  95

Gly Trp Glu Ala Leu Glu Asp Ala Gly Ile Val Pro Arg His Leu Arg
            100                 105                 110

Gly Thr Arg Thr Ser Val Phe Met Gly Ala Met Trp Asp Asp Tyr Ala
        115                 120                 125

His Leu Ala His Ala Arg Gly Glu Ala Ala Leu Thr Arg His Ser Leu
    130                 135                 140

Thr Gly Thr His Arg Gly Met Ile Ala Asn Arg Leu Ser Tyr Ala Leu
145                 150                 155                 160

Gly Leu Gln Gly Pro Ser Leu Thr Val Asp Thr Gly Gln Ser Ser Ser
                165                 170                 175

Leu Ala Ala Val His Met Ala Cys Glu Ser Leu Ala Arg Gly Glu Ser
            180                 185                 190

Asp Leu Ala Leu Val Gly Gly Val Asn Leu Val Leu Asp Pro Ala Gly
        195                 200                 205

Thr Thr Gly Val Glu Arg Phe Gly Ala Leu Ser Pro Asp Gly Arg Cys
    210                 215                 220

Tyr Thr Phe Asp Ser Arg Ala Asn Gly Tyr Ala Arg Gly Glu Gly Gly
```

-continued

```
              225                 230                 235                 240
        Val Val Val Val Leu Lys Pro Thr His Arg Ala Leu Ala Asp Gly Asp
                        245                 250                 255

Thr Val Tyr Cys Glu Ile Leu Gly Ser Ala Leu Asn Asn Asp Gly Ala
                        260                 265                 270

Thr Glu Gly Leu Thr Val Pro Ser Ala Arg Ala Gln Ala Asp Val Leu
                        275                 280                 285

Arg Gln Ala Trp Glu Arg Ala Arg Val Ala Pro Thr Asp Val Gln Tyr
                290                 295                 300

Val Glu Leu His Gly Thr Gly Thr Pro Ala Gly Asp Pro Val Glu Ala
        305                 310                 315                 320

Glu Gly Leu Gly Thr Ala Leu Gly Thr Ala Arg Pro Ala Glu Ala Pro
                        325                 330                 335

Leu Leu Val Gly Ser Val Lys Thr Asn Ile Gly His Leu Glu Gly Ala
                        340                 345                 350

Ala Gly Ile Ala Gly Leu Leu Lys Thr Val Leu Ser Ile Lys Asn Arg
                        355                 360                 365

His Leu Pro Ala Ser Leu Asn Phe Thr Ser Pro Asn Pro Arg Ile Asp
                370                 375                 380

Leu Asp Ala Leu Arg Leu Arg Val His Thr Ala Tyr Gly Pro Trp Pro
        385                 390                 395                 400

Ser Pro Asp Arg Pro Leu Val Ala Gly Val Ser Ser Phe Gly Met Gly
                        405                 410                 415

Gly Thr Asn Cys His Val Val Leu Ser Glu Leu Arg Asn Ala Gly Gly
                        420                 425                 430

Asp Gly Ala Gly Lys Gly Pro Tyr Thr Gly Thr Glu Asp Arg Leu Gly
                        435                 440                 445

Ala Thr Glu Ala Glu Lys Arg Pro Asp Pro Ala Thr Gly Asn Gly Pro
                450                 455                 460

Asp Pro Ala Gln Asp Thr His Arg Tyr Pro Ala Leu Ile Leu Ser Ala
        465                 470                 475                 480

Arg Ser Asp Ala Ala Leu Arg Ala Gln Ala Glu Arg Leu Arg His His
                        485                 490                 495

Leu Glu His Ser Pro Gly Gln Arg Leu Arg Asp Thr Ala Tyr Ser Leu
                        500                 505                 510

Ala Thr Arg Arg Gln Val Phe Glu Arg His Ala Val Thr Gly His
                        515                 520                 525

Asp Arg Glu Asp Leu Leu Asn Gly Leu Arg Asp Leu Glu Asn Gly Leu
                530                 535                 540

Pro Ala Pro Gln Val Leu Leu Gly Arg Thr Pro Thr Glu Pro Gly
        545                 550                 555                 560

Gly Leu Ala Phe Leu Phe Ser Gly Gln Gly Ser Gln Pro Gly Met
                        565                 570                 575

Gly Lys Arg Leu His Gln Val Phe Pro Gly Phe Arg Asp Ala Leu Asp
                        580                 585                 590

Glu Val Cys Ala Glu Leu Asp Thr His Leu Gly Arg Leu Leu Gly Pro
                        595                 600                 605

Glu Ala Gly Pro Pro Leu Arg Asp Val Met Phe Ala Glu Arg Gly Thr
                        610                 615                 620

Ala His Ser Ala Leu Leu Ser Glu Thr His Tyr Thr Gln Ala Ala Leu
        625                 630                 635                 640

Phe Ala Leu Glu Thr Ala Leu Phe Arg Leu Leu Val Gln Trp Gly Leu
                        645                 650                 655
```

```
Lys Pro Asp His Leu Ala Gly His Ser Val Gly Glu Ile Ala Ala Ala
            660                 665                 670

His Ala Ala Gly Ile Leu Asp Leu Ser Asp Ala Ala Glu Leu Val Ala
            675                 680                 685

Thr Arg Gly Ala Leu Met Arg Ser Leu Pro Gly Gly Gly Val Met Leu
            690                 695                 700

Ser Val Gln Ala Pro Glu Ser Glu Val Ala Pro Leu Leu Leu Gly Arg
705                 710                 715                 720

Glu Ala His Val Gly Leu Ala Ala Val Asn Gly Pro Asp Ala Val Val
                    725                 730                 735

Val Ser Gly Glu Arg Gly His Val Ala Ala Ile Glu Gln Ile Leu Arg
            740                 745                 750

Asp Arg Gly Arg Lys Ser Arg Tyr Leu Arg Val Ser His Ala Phe His
            755                 760                 765

Ser Pro Leu Met Glu Pro Val Leu Glu Glu Phe Ala Glu Ala Val Ala
            770                 775                 780

Gly Leu Thr Phe Arg Ala Pro Thr Thr Pro Leu Val Ser Asn Leu Thr
785                 790                 795                 800

Gly Ala Pro Val Asp Asp Arg Thr Met Ala Thr Pro Ala Tyr Trp Val
                    805                 810                 815

Arg His Val Arg Glu Ala Val Arg Phe Gly Asp Gly Ile Arg Ala Leu
            820                 825                 830

Gly Lys Leu Gly Thr Gly Ser Phe Leu Glu Val Gly Pro Asp Gly Val
            835                 840                 845

Leu Thr Ala Met Ala Arg Ala Cys Val Thr Ala Ala Pro Glu Pro Gly
            850                 855                 860

His Arg Gly Glu Gln Gly Ala Asp Ala Asp Ala His Thr Ala Leu Leu
865                 870                 875                 880

Leu Pro Ala Leu Arg Arg Gly Arg Asp Glu Ala Arg Ser Leu Thr Glu
                    885                 890                 895

Ala Val Ala Arg Leu His Leu His Gly Val Pro Met Asp Trp Thr Ser
            900                 905                 910

Val Leu Gly Gly Asp Val Ser Arg Val Pro Leu Pro Thr Tyr Ala Phe
            915                 920                 925

<210> SEQ ID NO 25
<211> LENGTH: 922
<212> TYPE: PRT
<213> ORGANISM: Streptomyces fradiae

<400> SEQUENCE: 25

Met Ser Ser Ala Leu Arg Arg Ala Val Gln Ser Asn Cys Gly Tyr Gly
  1               5                  10                  15

Asp Leu Met Thr Ser Asn Thr Ala Ala Gln Asn Thr Gly Asp Gln Glu
                 20                  25                  30

Asp Val Asp Gly Pro Asp Ser Thr His Gly Gly Glu Ile Ala Val Val
             35                  40                  45

Gly Met Ser Cys Arg Leu Pro Gly Ala Ala Gly Val Glu Glu Phe Trp
         50                  55                  60

Glu Leu Leu Arg Ser Gly Arg Gly Met Pro Thr Arg Gln Asp Asp Gly
 65                  70                  75                  80

Thr Trp Arg Ala Ala Leu Glu Asp His Ala Gly Phe Asp Ala Gly Phe
                 85                  90                  95

Phe Gly Met Asn Ala Arg Gln Ala Ala Ala Thr Asp Pro Gln His Arg
```

```
                    100                 105                 110
Leu Met Leu Glu Leu Gly Trp Glu Ala Leu Glu Asp Ala Gly Ile Val
        115                 120                 125

Pro Gly Asp Leu Thr Gly Thr Asp Thr Gly Val Phe Ala Gly Val Ala
130                 135                 140

Ser Asp Asp Tyr Ala Val Leu Thr Arg Arg Ser Ala Val Ser Ala Gly
145                 150                 155                 160

Gly Tyr Thr Ala Thr Gly Leu His Arg Ala Leu Ala Asn Arg Leu
                165                 170                 175

Ser His Phe Leu Gly Leu Arg Gly Pro Ser Leu Val Val Asp Ser Ala
            180                 185                 190

Gln Ser Ala Ser Leu Val Ala Val Gln Leu Ala Cys Glu Ser Leu Arg
        195                 200                 205

Arg Gly Glu Thr Ser Leu Ala Val Ala Gly Val Asn Leu Ile Leu
        210                 215                 220

Thr Glu Glu Ser Thr Thr Val Met Glu Arg Met Gly Ala Leu Ser Pro
225                 230                 235                 240

Asp Gly Arg Cys His Thr Phe Asp Ala Arg Ala Asn Gly Tyr Val Arg
                245                 250                 255

Gly Glu Gly Gly Gly Ala Val Val Leu Lys Pro Leu Asp Ala Ala Leu
                260                 265                 270

Ala Asp Gly Asp Arg Val Tyr Cys Val Ile Lys Gly Ala Val Asn
        275                 280                 285

Asn Asp Gly Gly Gly Ala Ser Leu Thr Thr Pro Asp Arg Glu Ala Gln
        290                 295                 300

Glu Ala Val Leu Arg Gln Ala Tyr Arg Arg Ala Gly Val Ser Thr Gly
305                 310                 315                 320

Ala Val Arg Tyr Val Glu Leu His Gly Thr Gly Thr Arg Ala Gly Asp
                325                 330                 335

Pro Val Glu Ala Ala Ala Leu Gly Ala Val Leu Gly Ala Gly Ala Asp
            340                 345                 350

Ser Gly Arg Ser Thr Pro Leu Ala Val Gly Ser Val Lys Thr Asn Val
        355                 360                 365

Gly His Leu Glu Gly Ala Ala Gly Ile Val Gly Leu Ile Lys Ala Thr
    370                 375                 380

Leu Cys Val Arg Lys Gly Glu Leu Val Pro Ser Leu Asn Phe Ser Thr
385                 390                 395                 400

Pro Asn Pro Asp Ile Pro Leu Asp Asp Leu Arg Leu Arg Val Gln Thr
                405                 410                 415

Glu Arg Gln Glu Trp Asn Glu Glu Asp Asp Arg Pro Arg Val Ala Gly
            420                 425                 430

Val Ser Ser Phe Gly Met Gly Gly Thr Asn Val His Leu Val Ile Ala
        435                 440                 445

Glu Ala Pro Ala Ala Gly Ser Ser Gly Ala Gly Ser Gly Ala
        450                 455                 460

Gly Ser Gly Ala Gly Ile Ser Ala Val Ser Gly Val Val Pro Val Val
465                 470                 475                 480

Val Ser Gly Arg Ser Arg Val Val Arg Glu Ala Ala Gly Arg Leu
            485                 490                 495

Ala Glu Val Val Glu Ala Gly Gly Val Gly Leu Ala Asp Val Ala Val
            500                 505                 510

Thr Met Ala Asp Arg Ser Arg Phe Gly Tyr Arg Ala Val Val Leu Ala
    515                 520                 525
```

-continued

```
Arg Gly Glu Ala Glu Leu Ala Gly Arg Leu Arg Ala Leu Ala Gly Gly
    530                 535                 540

Asp Pro Asp Ala Gly Val Val Thr Gly Ala Val Leu Asp Gly Gly Val
545                 550                 555                 560

Val Val Gly Ala Ala Pro Gly Gly Ala Gly Ala Gly Gly Ala Gly
                565                 570                 575

Ala Ala Gly Gly Ala Gly Gly Gly Val Val Leu Val Phe Pro Gly
        580                 585                 590

Gln Gly Thr Gln Trp Val Gly Met Gly Ala Gly Leu Leu Gly Ser Ser
        595                 600                 605

Glu Val Phe Ala Ala Ser Met Arg Glu Cys Ala Arg Ala Leu Ser Val
    610                 615                 620

His Val Gly Trp Asp Leu Leu Glu Val Val Ser Gly Gly Ala Gly Leu
625                 630                 635                 640

Glu Arg Val Asp Val Val Gln Pro Val Thr Trp Ala Val Met Val Ser
                645                 650                 655

Leu Ala Arg Tyr Trp Gln Ala Met Gly Val Asp Val Ala Ala Val
                660                 665                 670

Gly His Ser Gln Gly Glu Ile Ala Ala Ala Thr Val Ala Gly Ala Leu
        675                 680                 685

Ser Leu Glu Asp Ala Ala Ala Val Val Ala Leu Arg Ala Gly Leu Ile
        690                 695                 700

Gly Arg Tyr Leu Ala Gly Arg Gly Ala Met Ala Ala Val Pro Leu Pro
705                 710                 715                 720

Ala Gly Glu Val Glu Ala Gly Leu Ala Lys Trp Pro Gly Val Glu Val
                725                 730                 735

Ala Ala Val Asn Gly Pro Ala Ser Thr Val Val Ser Gly Asp Arg Arg
            740                 745                 750

Ala Val Ala Gly Tyr Val Ala Val Cys Gln Ala Glu Gly Val Gln Ala
        755                 760                 765

Arg Leu Ile Pro Val Asp Tyr Ala Ser His Ser Arg His Val Glu Asp
770                 775                 780

Leu Lys Gly Glu Leu Glu Arg Val Leu Ser Gly Ile Arg Pro Arg Ser
785                 790                 795                 800

Pro Arg Val Pro Val Cys Ser Thr Val Ala Gly Glu Gln Pro Gly Glu
                805                 810                 815

Pro Val Phe Asp Ala Gly Tyr Trp Phe Arg Asn Leu Arg Asn Arg Val
            820                 825                 830

Glu Phe Ser Ala Val Val Gly Gly Leu Leu Glu Glu Gly His Arg Arg
        835                 840                 845

Phe Ile Glu Val Ser Ala His Pro Val Leu Val His Ala Ile Glu Gln
850                 855                 860

Thr Ala Glu Ala Ala Asp Arg Ser Val His Ala Thr Gly Thr Leu Arg
865                 870                 875                 880

Arg Gln Asp Asp Ser Pro His Arg Leu Leu Thr Ser Thr Ala Glu Ala
                885                 890                 895

Trp Ala His Gly Ala Thr Leu Thr Trp Asp Pro Ala Leu Pro Pro Gly
            900                 905                 910

His Leu Thr Thr Leu Pro Thr Tyr Pro Phe
        915                 920
```

<210> SEQ ID NO 26
<211> LENGTH: 122

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
ctaggccggg ccggactggt agatctgcct acgtatcctt tccagggcaa gcggttctgg      60
ctgcagccgg accgcactag tcctcgtgac gagggagatg catcgagcct gagggaccgg     120
tt                                                                   122

<210> SEQ ID NO 27
<211> LENGTH: 118
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
aaccggtccc tcaggctcga tgcatctccc tcgtcacgag gactagtgcg gtccggctgc      60
agccagaacc gcttgccctg gaaggatac gtaggcagat ctaccagtcc ggcccggc       118

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
ccatatggcc gcatccgcgt cagcgt                                          26

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
ggctagcggg tcctcgtccg tgccgaggtc a                                    31

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
aattcacatc accatcacca tcactagtag gaggtctggc catctaga                  48

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
```

```
agcttctaga tggccagacc tcctactagt gatggtgatg gtgatgtg                        48
```

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 32

```
tggaccgccg ccaattgcct aggcgggccg aacccggct                                 39
```

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33

```
cctgcaggcc atcgcgacga ccgcgaccgg ttcgcc                                    36
```

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 34

```
ccacatatgc atgtccccgg cgaggaa                                              27
```

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 35

```
ccctgtccgg agaagaggaa ggcgaggccg                                           30
```

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 36

```
ccatatgtct ggagaactcg cgatttcccg cagt                                      34
```

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 37

```
ggctagcggg tcgtcgtcgt cccggctg                                             28
```

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 38
tacctaggcc gggccggact ggtcgacctg ccgggtt                              37

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 39
atgttaaccg gtcgcgcagg ctctccgtct                                     30

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
atgttaacgg gtctgccgcg tgccgagcgg ac                                  32

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 41
cttctagact atgaattccc tccgcccagc                                     30

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 42
taagatcttc cgacgtacgc gttccagc                                       28

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 43
atgctagcca ctgcgccgac gaatcaccgg tgg                                 33

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 44
tacctgaggg accggctagc gggtctgccg cgtg                               34

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 45
atgctagccg ttgtgccggc tcgccggtcg gtcc                               34

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 46
cgttcctgag gtcgctggcc caggcgta                                     28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 47
cgaagcttga caccgcggcg cggcgcgg                                     28

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 48
gcgcgccaat tgcgtgcaca tctcgat                                      27

<210> SEQ ID NO 49
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 49
cctgcaggcc atcgcgacga ccgcgaccgg ttcgccg                           37

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 50
gtctcaagct tcggcatcag cggcaccaa                                    29

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 51
cgtgcgatat ccctgctcgg cgagcgca                                     28

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 52
gatggcctgc aggctgcccg gcggtgtgag ca                                32

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 53
gccgaagctt gagaccccccg cccggcgcgg tcgc                             34

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 54
ccatatgacc tcgaacaccg ctgcacagaa                                   30

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 55
ggctagcggc tcctgggctt cgaagctctt ct                                32